(12) United States Patent
Strachan et al.

(10) Patent No.: US 12,360,111 B2
(45) Date of Patent: Jul. 15, 2025

(54) G PROTEIN-COUPLED RECEPTOR SCREENING SYSTEMS

(71) Applicant: The University of North Carolina at Chapel Hill, Chapel Hill, NC (US)

(72) Inventors: Ryan Strachan, Chapel Hill, NC (US); Reid Olsen, Oxford (GB); Bryan Leo Roth, Durham, NC (US); Justin Gregory English, Chapel Hill, NC (US); Jeffrey Frederick Diberto, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1077 days.

(21) Appl. No.: 17/296,818

(22) PCT Filed: Dec. 3, 2019

(86) PCT No.: PCT/US2019/064159
§ 371 (c)(1),
(2) Date: May 25, 2021

(87) PCT Pub. No.: WO2020/117752
PCT Pub. Date: Jun. 11, 2020

(65) Prior Publication Data
US 2022/0002357 A1      Jan. 6, 2022

Related U.S. Application Data

(60) Provisional application No. 62/886,452, filed on Aug. 14, 2019, provisional application No. 62/775,045, filed on Dec. 4, 2018.

(51) Int. Cl.
*G01N 33/566* (2006.01)
*C12N 15/62* (2006.01)

(52) U.S. Cl.
CPC .......... *G01N 33/566* (2013.01); *C12N 15/62* (2013.01); *G01N 2500/04* (2013.01)

(58) Field of Classification Search
CPC .................................................... G01N 33/566
See application file for complete search history.

(56) References Cited

U.S. PATENT DOCUMENTS

2017/0234870 A1* 8/2017 Bouvier ............... C12N 9/0069
435/8

* cited by examiner

*Primary Examiner* — Albert M Navarro
(74) *Attorney, Agent, or Firm* — Thomas | Horstemeyer, LLP

(57) ABSTRACT

Disclosed herein is a G protein-coupled receptor (GPCR) assay platform comprised of two complementary systems that equate dynamic intermolecular interactions between a receptor and transducer with more complex stimulus-response cascades in living cells. In the disclosed in vitro ADSoRB method, the forced dissociation of transducers like G protein heterotrimers from receptors alters receptor conformations and ligand interactions to simulate pathway activation in a cell. In the disclosed TRUPATH method, measuring the extent of engineered G protein heterotrimer complex dissociation provides single transducer resolution in a cell.

17 Claims, 71 Drawing Sheets

Specification includes a Sequence Listing.

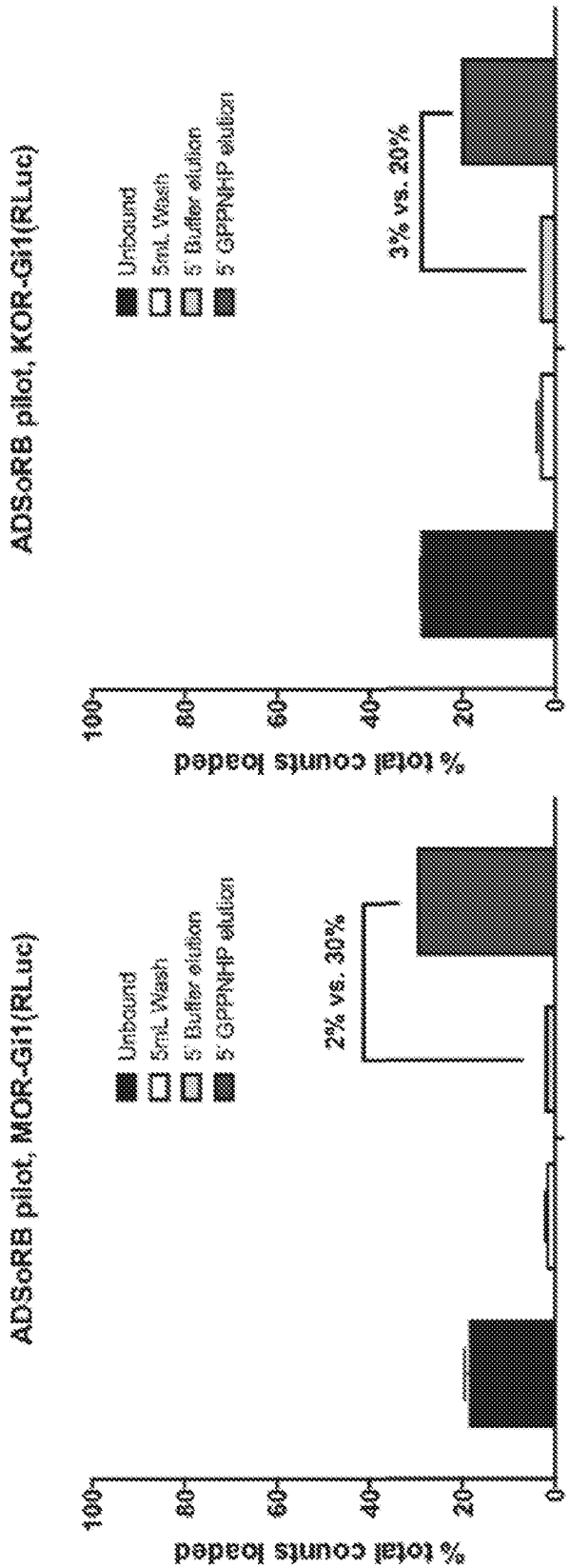

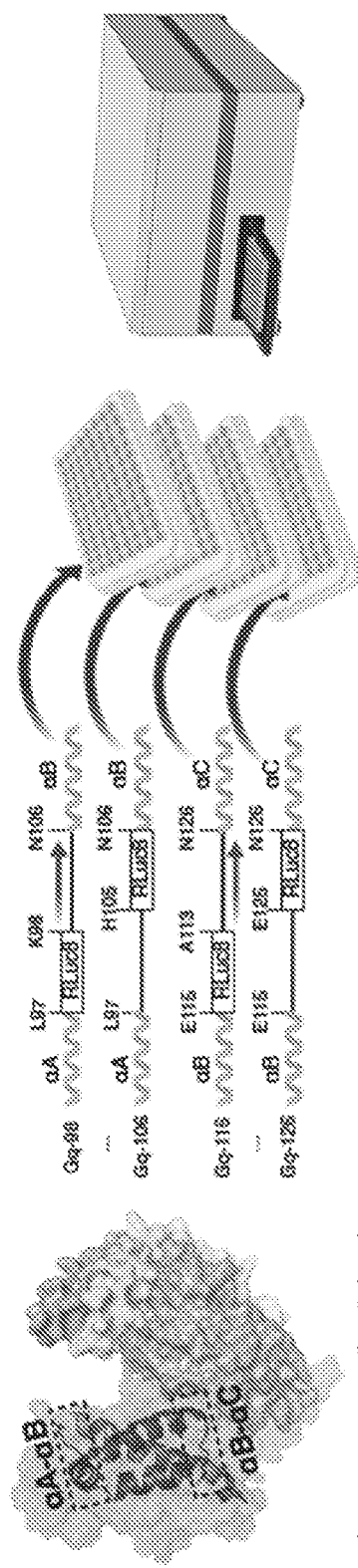

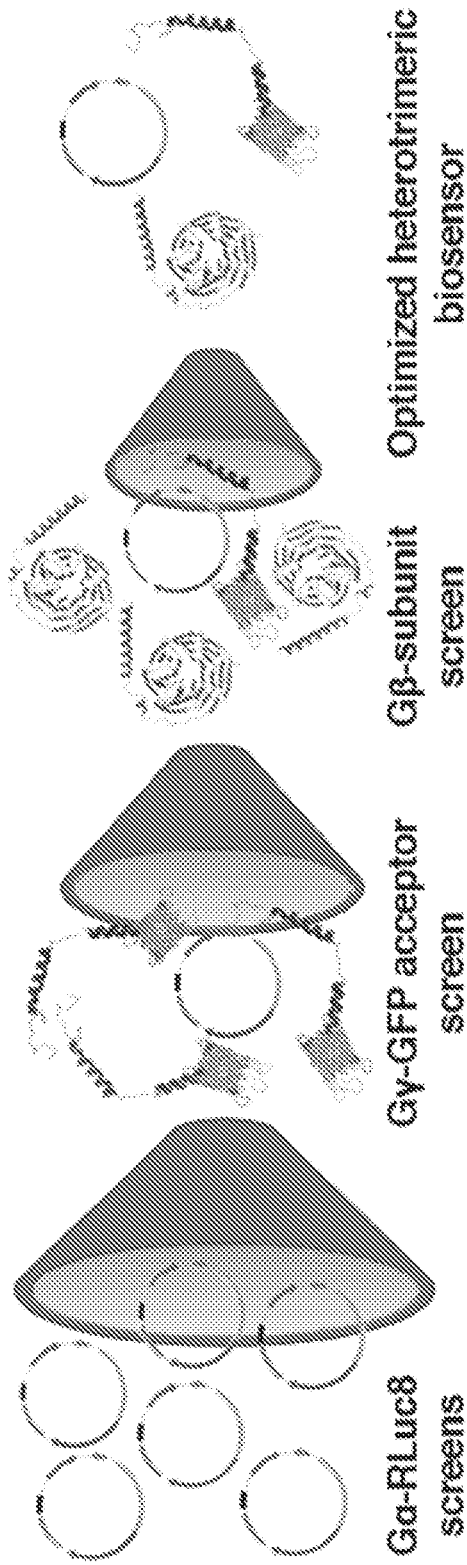

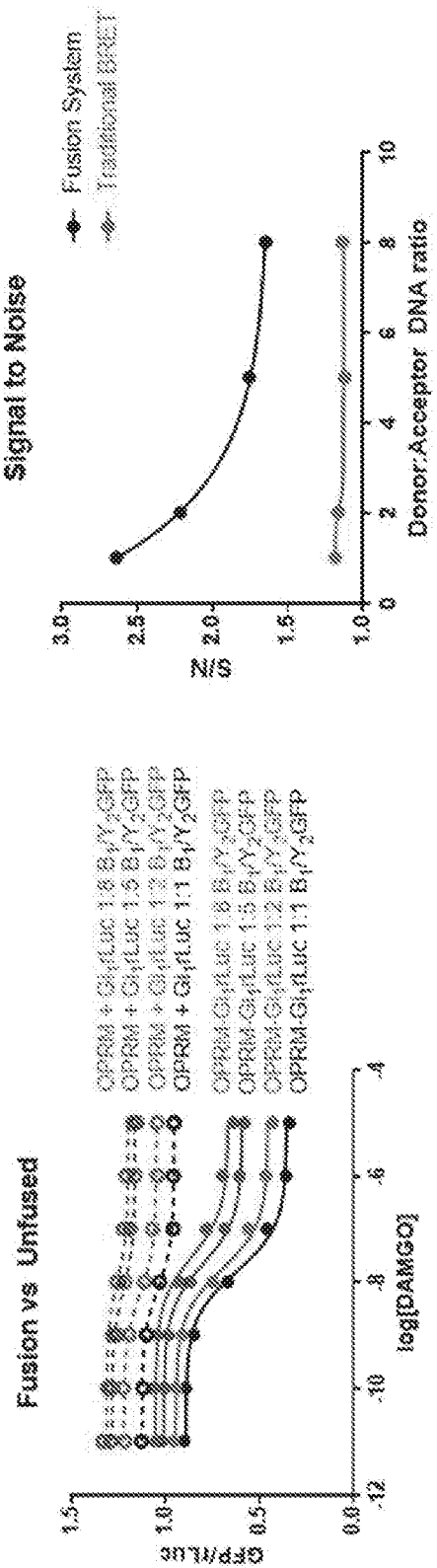
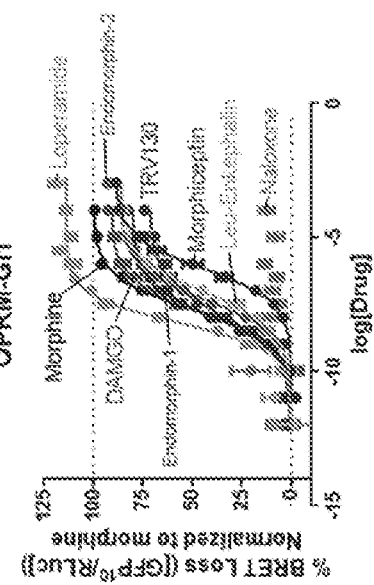
FIG. 4A
FIG. 4B
FIG. 4C

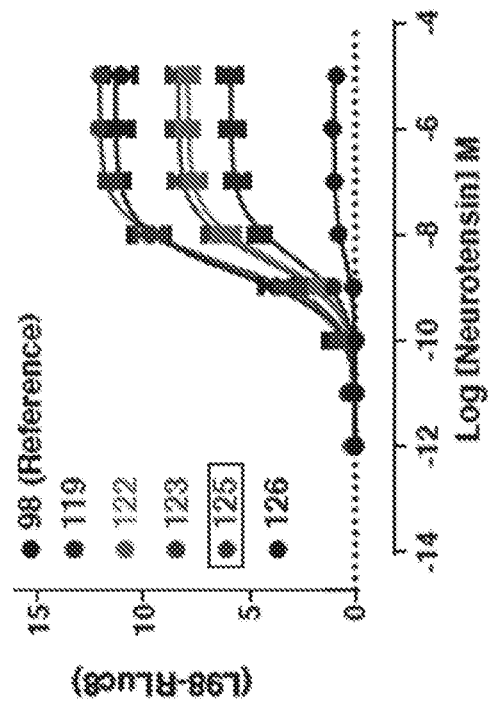
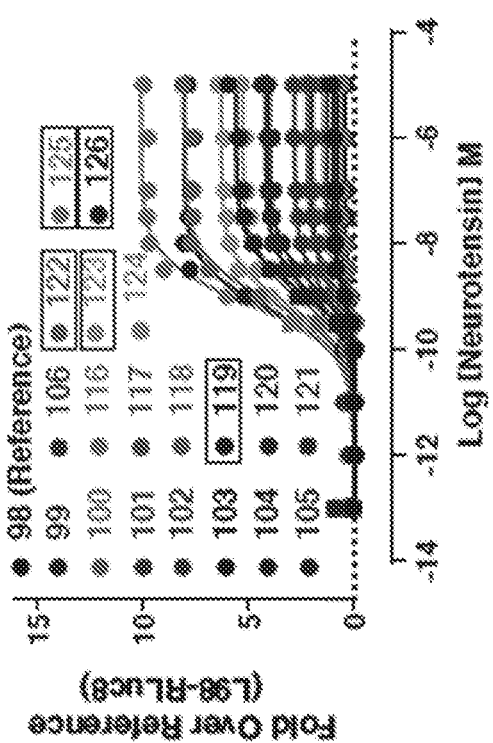
FIG. 7B
FIG. 7C

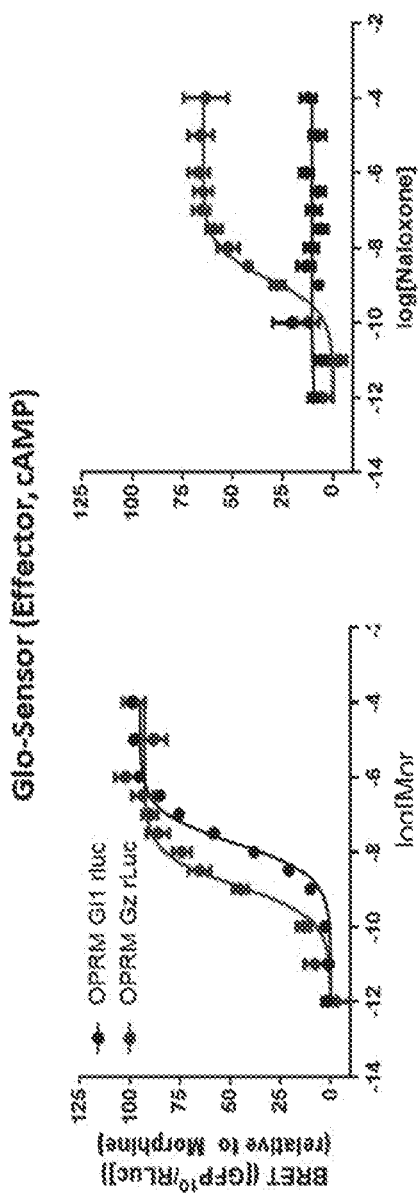
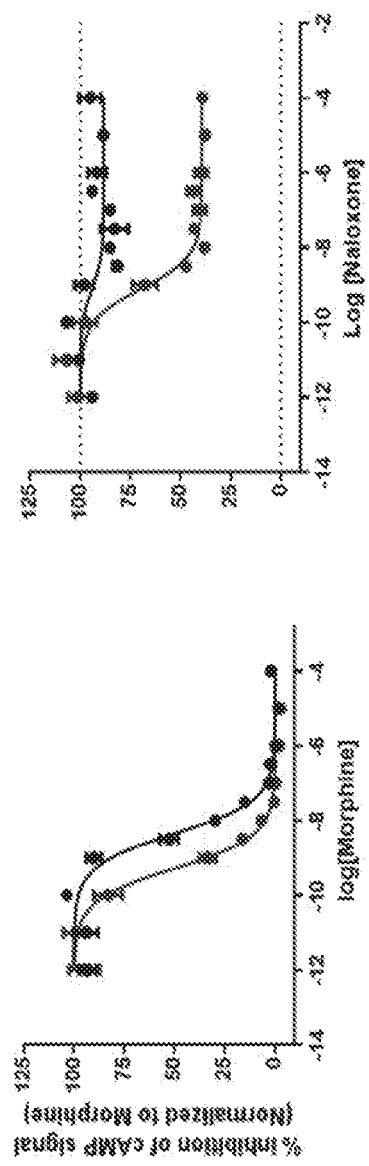
FIG. 12A
FIG. 12B
FIG. 12C
FIG. 12D

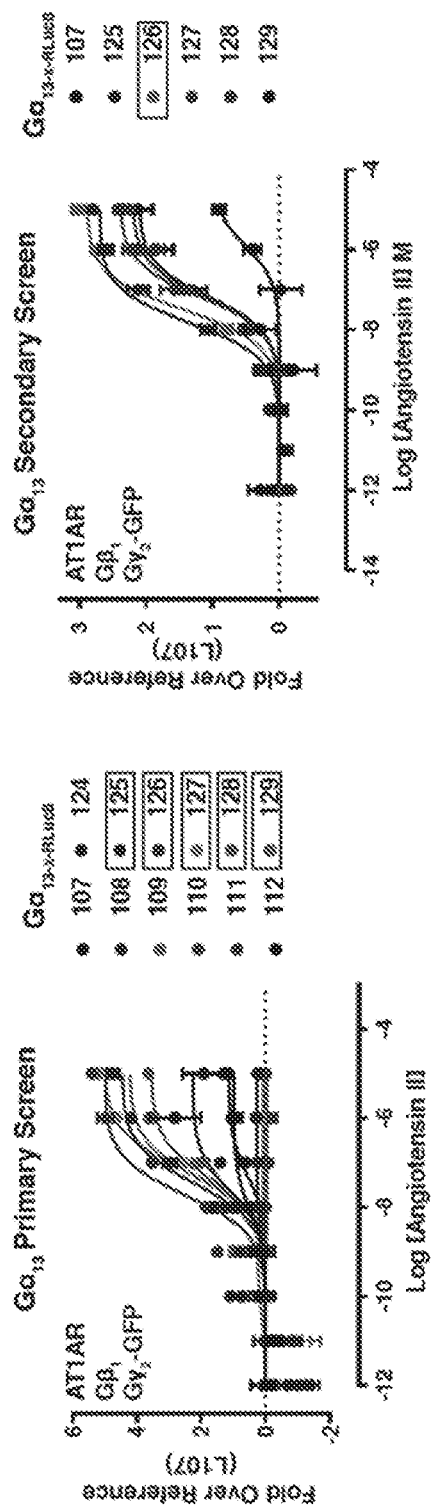
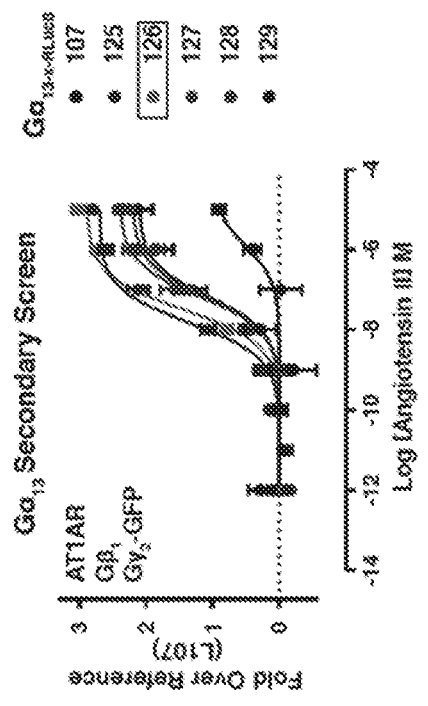
FIG. 25B
FIG. 25A

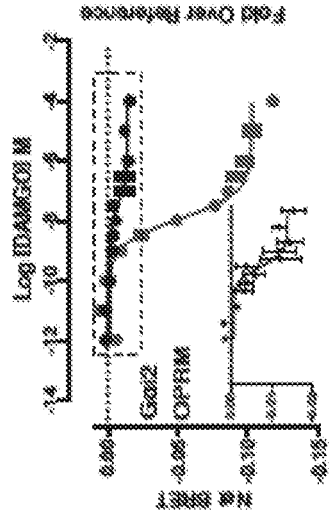
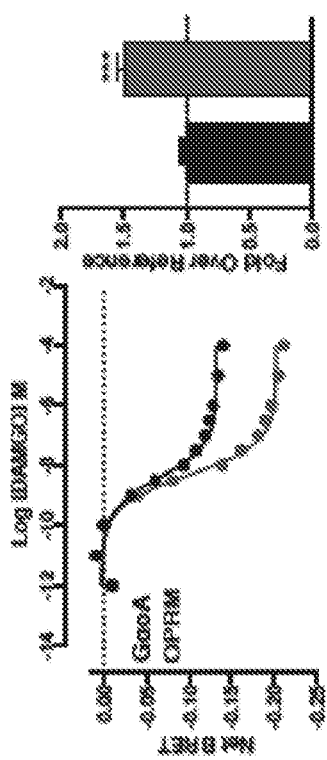
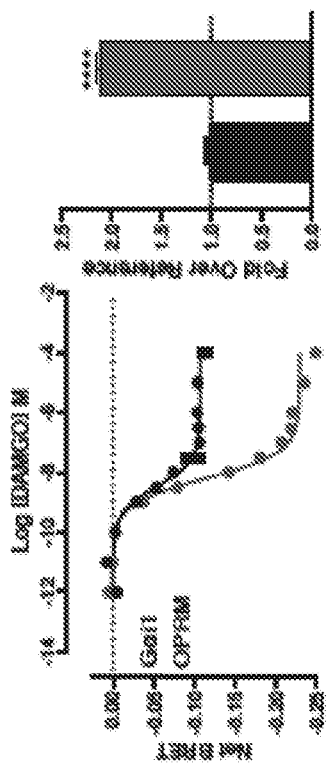
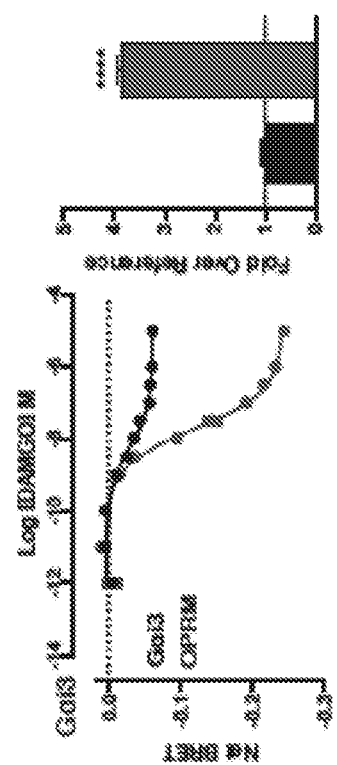
FIG. 29A
FIG. 29B
FIG. 29C
FIG. 29D

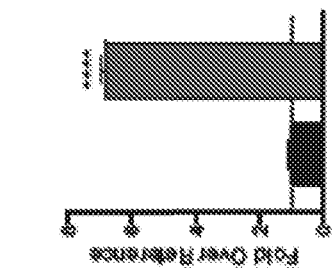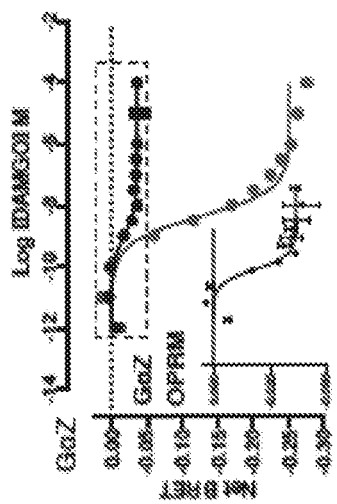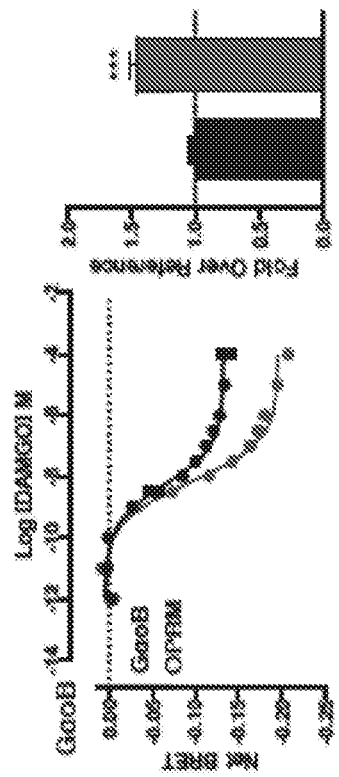
FIG. 29E
FIG. 29F
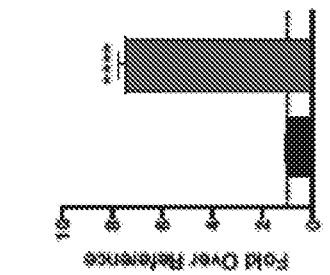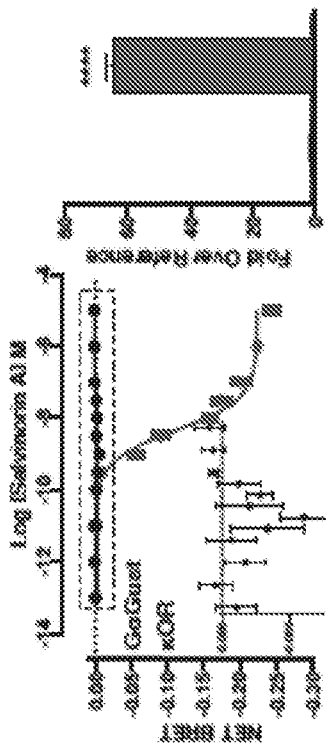
FIG. 29G
FIG. 29H

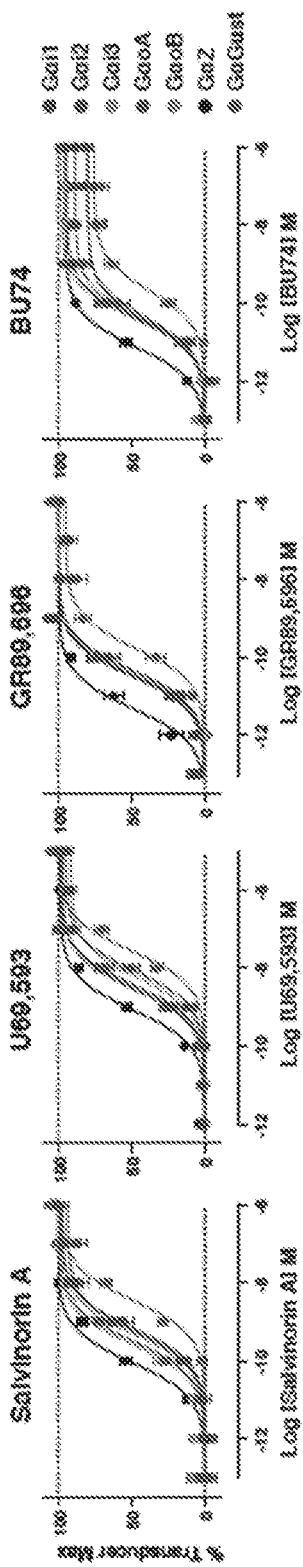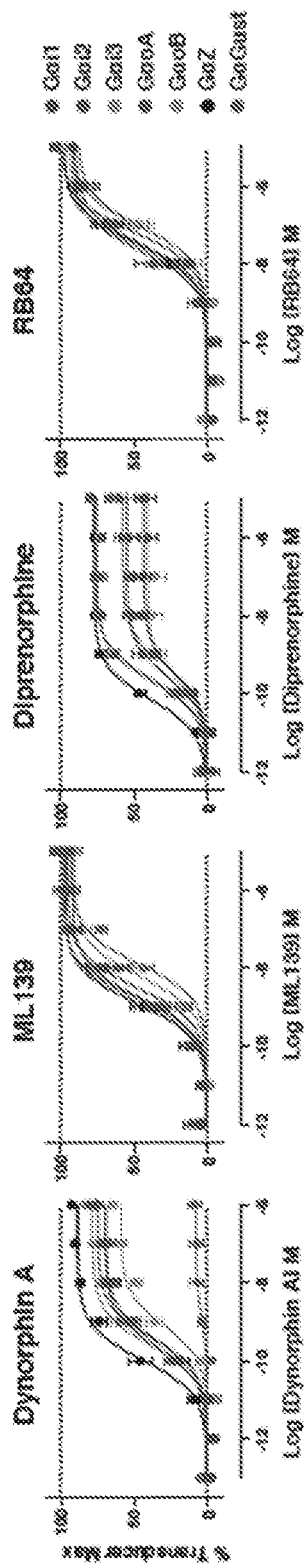

G PROTEIN-COUPLED RECEPTOR SCREENING SYSTEMS

CROSS-REFERENCE TO RELATED APPLICATIONS

This application is a National Stage of International Application No. PCT/US2019/064159, filed Dec. 3, 2019, which claims benefit of U.S. Provisional Application No. 62/775,045, filed Dec. 4, 2018, and U.S. Provisional Application No. 62/886,452, filed Aug. 14, 2019, which are hereby incorporated herein by reference in their entireties.

STATEMENT REGARDING FEDERALLY SPONSORED RESEARCH OR DEVELOPMENT

This invention was made with government support under Grant Numbers MH109943, NS093917, MH104974, MH112205, and DA045657 awarded by the National Institutes of Health. The government has certain rights in the invent.

SEQUENCE LISTING

This application contains a sequence listing filed in electronic form as an ASCII.txt file entitled "921404-2050 Sequence Listing_ST25" created on Nov. 25, 2019. The content of the sequence listing is incorporated herein in its entirety.

BACKGROUND

G protein-coupled receptors (GPCRs) are modulated by 34% of FDA-approved drugs (Hauser A S, et al. Nat Rev Drug Discov. 2017 16(12):829-842), making them the most highly targeted receptors in the clinic. Current GPCR drugs have a rather broad mechanism of action-they activate (agonist), block (antagonist), or allosterically modulate numerous signaling pathways downstream of their target receptor. Driving much of the recent progress in GPCR molecular pharmacology has been the notion that selective modulation of distinct GPCR pathways (i.e., those associated ONLY with therapeutic effects) will yield safer and more efficacious next-generation biased therapeutics (Kenakin T. Mol Pharmacol. 2015 88(6):1055-61). However, GPCR signal transduction is immensely complex (~350 druggable GPCRs activate any number of 16 different canonical G protein signaling pathways and an untold number of non-canonical pathways), which complicates efforts to 1) understand the individual contributions of each pathway in normal and diseased states and 2) identify and design biased agonists. As a result, drugs with engineered biased signaling profiles have yet to hit the market, although several are in the (pre)clinical pipeline (Hodavance S Y, et al. J Cardiovasc Pharmacol. 2016 67(3):193-202).

Current drug discovery campaigns are limited when it comes to discovering biased agonists for several reasons. First, most screening strategies exploit cell-based assays that are highly amplified, inefficient, and have low fidelity to the actual pathway under study. Second, good assays exist for only a small fraction of the 16 non-visual G protein signaling pathways in humans, thereby limiting therapeutic intervention to only the best studied pathways. Third, little is known about which pathways to target for a desired therapeutic effect (Michel M C, et al. Mol Pharmacol. 2018 93(4):259-265). Fourth, current physical screening approaches are unable to isolate ligands with a desired pharmacology from chemically diverse and complex ligand mixtures (e.g. mixtures of $>1 \times 10^9$ unique small molecules or peptides). Clearly, GPCR drug discovery needs alternate screening approaches. Disclosed herein is a complete drug discovery platform for i) isolating new chemical matter with predefined pharmacology from complex libraries and ii) comprehensive profiling of signaling pathways to uncover biased signaling.

SUMMARY

Disclosed herein is a G protein-coupled receptor (GPCR) assay platform comprised of two complementary systems that equate dynamic intermolecular interactions between a receptor and transducer with more complex stimulus-response cascades in living cells. In the disclosed in vitro ADSoRB method, the forced dissociation of transducers like G protein heterotrimers alters receptor conformations and ligand interactions to simulate pathway activation in a cell. This conceptual framework enables isolation of ligands with a defined pharmacology from complex library mixtures in vitro. In the disclosed TRUPATH method, measuring the extent of engineered G protein heterotrimer complex dissociation provides single transducer resolution in a cell. Transducers can exist unfused or fused to the GPCR and can include engineered heterotrimeric G proteins (Gα(Rluc)/Gβγ-GFP), an engineered Gα(Rluc) subunit, native heterotrimeric G protein, native Gα subunit, arrestin, a signaling associated protein, or a protein or protein fragment that through reversible coupling induces active or inactive structural changes in the receptor (e.g., antibodies or nanobodies or similar proteins and peptides). In cases where complex stability and extreme specificity are required, the GPCR and transducer are connected directly or by a flexible linker (see ADSoRB method below). By fusing transducers to the receptor, the system constitutes a biologically relevant complex, has a 1:1 local stoichiometry, maintains appropriate membrane trafficking, and has fidelity to the fused transducer pathway. The two screening systems are disclosed below.

The first in vitro screening system using the disclosed modulation of receptor-transducer interactions, referred to herein as ADSoRB (Affinity-Directed Selection of Receptor Binders), leverages the differential affinity that ligands display toward distinct receptor conformational states (known as molecular efficacy; Strachan R T et al. J Biol Chem. 2014; 289(20):14211-24) to enable rapid isolation of GPCR ligands with a defined pharmacology (FIG. 1). In terms of G protein transducers, signaling complex formation involves intermolecular interactions between the receptor and G protein that after receptor and transducer conformations, which is accompanied by increased binding affinity of activating ligands (i.e. agonists; De Lean A et al. J Biol Chem. 1980 Aug. 10; 255(15):7108-17). Upon signaling complex uncoupling or dissociation concomitant with transducer activation, receptor-transducer allosteric interactions are broken, thus converting the receptor to a low affinity conformational state that binds agonists with low affinity. By virtue of lowering ligand affinity and thus increasing the dissociation rate, ligands with significant molecular efficacy (e.g. agonists with a large preference for the activated state relative to the inactive state) are specifically eluted (FIG. 1). This elution strategy is considered a 'functional elution' as the ligands that are eluted should predominantly be agonists or positive allosteric modulators. Other methodologies use unliganded receptors, static complexes, stabilized receptor conformations, and/or non-specific elution strategies that provide little control over ligand pharmacology. Unlike in these other methodologies, antagonists and other non-specifically bound molecules remain bound in the ADSoRB method as their affinity is not modulated by transducer-mediated allosteric effects. Consequently, the ADSoRB method provides a cleaner elution of target molecules and requires less downstream validation and removal of false positives. If anything, molecules like inverse agonists would be bound tighter as the receptor ensemble shifts towards predominantly inactive states. Such molecules could be eluted subsequent to agonists. As described herein, quickly switching between high and low affinity states for the same target receptor enables the binding and recovery of different ligand classes (e.g. agonists vs. antagonists). Notably, this in vitro strategy (i.e. switching affinity states) simulates cellular signaling processes at the level of ternary complex interactions to enable 1) screening of ligands in vitro with the same outcome as screening in cells, 2) efficient screening for ligands with a pre-defined pharmacology, 3) expansion of chemical space for new chemotypes by screening high complexity libraries, and 4) efficient and targeted screening for biased agonists. Therefore, disclosed herein is a method that relies on the real time switching between active and inactive receptor states as a correlate of cellular signaling to confer function to in vitro screens to screen extremely large and complex libraries.

Therefore, disclosed herein is a system comprising a G protein coupled receptor (GPCR) fused to a transducer (GPCR-transducer fusion) and incorporated into a membrane or nanodisk/lipodisc-type environment. Broadly, ADSoRB is a scalable platform involving fusions between any GPCR and any transducer (i.e. at the very least it applies to any GPCR and known transducer combination, totaling >12,800 biological complexes), which are then expressed in membranes (e.g., the active complex, FIG. 1A). In addition to known signal transducers, ADSoRB also includes yet-to-be discovered signal transducers as well as signaling mimetic proteins or engineered receptors that reversibly alter the receptor conformational ensemble, as described herein. In its most common embodiment, the ADSoRB GPCR-transducer fusion contains the optimal GPCR-Gα (Rluc) construct determined from TRUPATH screening below. The system can also contain Gβ and Gγ protein subunits as described further herein. Since each unique GPCR-transducer fusion target represents conformational ensembles that activate different signal transduction pathways in the cell, the pharmacology of each screen can be directed by simply changing the type of fused transducer. This provides unprecedented control over both the receptor target and the intended ligand function (i.e. activation of a given transducer signaling pathway).

Also disclosed is a method for identifying ligands with differential affinities toward different transducer complexes, wherein the GPCR and the transducer are initially coupled in an active GPCR-transducer complex. The method can then involve contacting the system with a composition comprising a plurality of candidate agents (FIG. 1B). Those agents with affinity for the GPCR-transducer complex will bind strongly as a ternary complex (ligand-GPCR-transducer), while the rest of the candidate agents can be washed away (FIG. 1C).

The method then involves uncoupling the transducer from the GPCR in real time (i.e. ternary complex dissociation; this also extends to any method that enables quick reversal of receptor conformational stabilization)—a major distinguishing step absent from previous static methodologies that use unliganded receptors, static complexes, irreversible mutant stabilized receptor conformations (e.g. thermostabilization), and/or generic elution strategies (e.g. heat, solvents, or pH). This can be accomplished, for example in the case of receptor-G protein ternary complexes, using an effective amount of non-hydrolyzable guanine nucleotide (GPPNHP, FIG. 1D) or other agents as listed below.

The method then involves eluting bound candidate agents from the system. The eluted candidate agents represent ligands with differential affinity for the GPCR in an active-like vs. inactive-like state (i.e. they bind tightly to transducer-coupled but not the uncoupled GPCR), and thus can activate the same transducer in live cells according to classic receptor theory (Kent et al. Mol Pharmacol 1980 17(1)14-23). Proof-of-concept is shown in FIG. 2A-D with full agonists of different opioid receptors (ORs). Of note, the data in FIGS. 2E and 2F show the ability to bind and elute an agonist (DAMGO) that signals efficaciously through the mu-opioid receptor, whereas the antagonist (naloxone) fails to bind and elute from the complex.

The method can further involve repeating the above steps using the eluted candidate agents to enrich for high efficacy ligands (applies equally to agonists, allosteric modulators, and inverse agonists; thus, it includes activators and inactivators of receptor pathways). Wash stringency can be adjusted to select for agents with varying binding affinities as well as increase the ability to direct agent pharmacology. Elution times can also be adjusted to enrich for agents with differing pharmacological effects. For example, full agonists or full inverse agonists should elute quickly, whereas ligands with modest efficacy and high affinity for the uncoupled receptor will elute more slowly. The combined use of switching receptor affinity states and applying a competitive ligand increases ADSoRB functional elution (FIG. 2G). Modifying the stabilization strategy and elution conditions can also yield dominant negative ligands that stabilize the receptor-transducer complex and inhibit signaling.

ADSoRB is a selection strategy that relies on the differential affinity of ligands to recognize or interact with different receptor states (e.g. native/unliganded, liganded, active, inactive, mutant, transducer or signaling mimetic-stabilized). In some embodiments, the candidate agent can be an agonist, antagonist, inverse agonist, or allosteric modulator. The candidate agent can be any molecule, such as a small-molecule, biologic (e.g. peptide, protein, antibody, nanobody, nucleic acid, aptamer), or a derivative or combination thereof, with the potential to differentially bind the GPCR depending on the receptor state. In some embodiments, the composition is a phage displaying the candidate agents, e.g. peptide candidate agents. The candidate agent can be from a library (e.g., peptide phage display, macrocycle libraries, DNA-encoded libraries, pooled small molecules, pooled peptides, tissue extracts, natural product extracts, yeast display, or other preparations, FIGS. 1 and 2).

In some embodiments, each candidate agent is tagged with an identifier, such as a nucleic acid barcode, to identify which of the plurality of candidate agents are present in the eluted fraction. In other embodiments, each agent can be identified using procedures such as small molecule mass spectrometry and peptide mass spectrometry.

The GPCR-transducer fusion is preferably integrated into a membrane or similar environment, such as a lipid bilayer. In the simplest embodiment, the GPCR-transducer fusion is incorporated into the membrane of a cell (microsomes from mammalian, insect, or other systems like virus-like particles, VLPs) in which it was expressed. Microsomes can be prepared using standard differential centrifugation techniques, with the potential to control the orientation of the GPCR-transducer fusion as 'right-side-out' or 'inside-out' for orientation-specific screening. In some embodiments, the GPCR-transducer fusion is incorporated into a detergent micelle, the membrane of a liposome, or a lipid nanoparticle. For example, the liposome can comprise a molecule such as dimyristoylphosphatidylcholine (DMPC). In others, the GPCR-transducer fusion is incorporated into lipid nanoparticles stabilized by apolipoproteins or copolymers.

In some embodiments, the GPCR-transducer fusion protein in a membrane or similar environment is immobilized on a bead (e.g. agarose or magnetic beads). In others, the GPCR-transducer protein can be recovered using centrifugation, filters, or surface immobilization such as on a surface plasmon resonance (SPR) sensor chip or array.

GPCRs have already been targeted by small molecules, proteins, endogenous and exogenous peptides, macrocycle ligands, aptamers, and antibodies; therefore, libraries of these types can yield ligands with novel chemotypes and pharmacology. Because GPCR ligands with large efficacies favor binding to active signaling complexes over the free receptor by several orders of magnitude, library molecules recovered by this system are likely to have considerable 'molecular efficacy' and maximally activate (or inactivate) distinct cellular pathways. The disclosed ADSoRB strategy allows for isolation of orthosteric and allosteric ligands from a much greater chemical space, with the potential to discover new chemotypes and thus new biology and therapy. Notably, given the allosteric basis for ADSoRB (i.e. the positive cooperativity between a ligand and given transducer), transducers could also include proteins or their fragments or other engineering methods that reversibly stabilize active and inactive receptor states. In terms of stabilizing inactive states, this could enable preferential isolation of inverse agonists or negative allosteric modulators using the same methodology (i.e. inverse agonists and negative allosteric modulators favor inactive states, just as agonists or positive allosteric modulators favor active states). For this to function as a typical ADSoRB assay, it could involve the engineering of domains into the inactive state stabilizers that are sensitive to small molecules or other agents that would alter protein conformation or induce other changes to promote dissociation from the receptor. The rather high affinity of inverse agonists for the low affinity uncoupled receptor would likely require additional agents like competitors to enhance dissociation (shown for an agonist in FIG. 2G). Alternatively, an engineering method that would allow the receptor to switch from inactive to active states (e.g. an engineered receptor that could be forced to adopt states with high constitutive activity) would similarly elute inverse agonists by way of negative cooperativity. By mimicking cellular signaling in vitro to provide control over ligand pharmacology (i.e. it overcomes the problem of in vitro assays lacking biological function), this technology delivers on multiple levels including: 1) the development of new ligands with diverse chemotypes and signaling properties for GPCRs, with the potential to aid computational efforts; 2) the development of biased drug-like molecules; 3) the identification of biased tool molecules that can be used to isolate and study signaling pathways downstream of GPCRs in vivo; 4) the discovery of tool molecules to activate orphan GPCRs to reveal their (patho)physiology; and 5) the discovery of novel allosteric modulators with tailored effects.

The second in vitro screening system using the disclosed modulation of GPCR-transducer complexes, referred to herein as TRUPATH (for TRansdUcerome Profile Analysis of g protein paTHways), can be used to measure G protein pathway activation by an agent. The initiating steps for G protein stimulus-response cascades are receptor-mediated guanine nucleotide exchange at the $G\alpha$-subunit of the $G\alpha/G\beta\gamma$ heterotrimer and subsequent dissociation or rearrangement of the heterotrimeric complex (see ADSoRB FIG. 2A). This leads to effector activation (Gether, U. and Kobilka, B. K. J. Biol. Chem. 1998 273, 17979-1798). A change in the resonance energy transfer between fluorescently (FRET) or luminescently (BRET) labeled G protein subunits correlates with this activation event and has been used as a proxy for direct measurements of ligand-receptor-transducer coupling (Janetopoulos, C et al. 2001 Science 291, 2408-2411)(Sauliére, A. et al. 2012 Nat. Chem. Biol. 8, 622-630)(Mastop, M. et al. 2018 PLOS ONE) (FIG. 3A). Because optimal FRET and BRET probe pairs depend upon both the proximity of the donor and acceptor proteins as well as the orientation of their transition dipole moments (FIG. 3B), the de novo design of high performing $G\alpha/G\beta\gamma$ sensors is challenging and non-obvious. As described herein, we designed new high-performing $G\alpha/G\beta\gamma$ BRET pairs (Tables 1 and 2, FIG. 29) using a purely empirical approach.

In these embodiments, the transducer is the $G\alpha$ subunit tagged with a luminescent donor or fluorescent acceptor (FIG. 3A). In these embodiments, if the $G\alpha$ protein subunit is tagged with a luminescent donor, then either the $G\beta$ protein subunit or the $G\gamma$ protein subunit is tagged with a fluorescent acceptor; and if the $G\alpha$ protein subunit is tagged with a fluorescent acceptor, then either the $G\beta$ protein subunit or the $G\gamma$ protein subunit is tagged with a luminescent donor. The positional insertion sites or chimeric fusions for each donor/acceptor pair are empirically optimized de novo by iterative testing of all combinations such that the composition of the biosensor has been experimentally determined (e.g. multiple points of insertion of the luminescent donor or fluorescent acceptor paneled against all possible $\beta\gamma$ dimer complexes with a fluorescent or luminescent donor to identify novel optimal constructs) (FIG. 3C-3I). The disclosed method can further involve measuring bioluminescence resonance energy transfer in a fused or unfused system (baseline BRET), contacting the system with the agent, and then measuring a second bioluminescence resonance energy transfer in the system. The difference between the first bioluminescence resonance energy transfer and the second bioluminescence resonance energy transfer can then be used to calculate G protein pathway activation (NET BRET).

In some embodiments, the disclosed TRUPATH system uses the receptor-transducer fusion used in the ADSoRB system for the same advantages conferred (e.g. stoichiometry to establish reliable measurements of pathway bias, trafficking and in some cases folding concerns, and avoiding off-target activation of the sensor by endogenous receptors or systems). In other embodiments such as during heterotrimer optimization (FIGS. 3, 7, 13-25), the receptor and transducer are unfused and can be used separately. Notably, the fusion system allows for a clear measurement of basal activity of the receptor and ensures that all active receptors have available to them a functional sensor. As shown in FIGS. 4A and 4B, the fusion approach increases the dynamic range and reliability of the measurement over the unfused scenario but is not necessary for the improvements described in the TRUPATH biosensor compositions (FIG. 29).

In some embodiments, the method involves repeating the above steps for the agent(s) at a plurality of doses and calculating a dose-response curve (FIGS. 4C, 7, 13-25, 32C-32J, and 33C-33D). Standard logistic regression fitting of dose-response curves enables estimates of common pharmacological parameters such as potency (EC50) and efficacy (Emax), including inverse agonism (FIG. 5A). In contrast to conventional functional assays, the minimized amplification and receptor reserve inherent to TRUPATH assays produce accurate parameter estimates without the need for data post-processing (FIG. 5B-5D).

In some embodiments, the method involves repeating the above steps for the agent at a plurality of kinetic conditions (FIG. 6).

In some embodiments, the method involves repeating the above steps for the agent using a plurality of Gα/Gβ/Gγ transducer combinations (FIG. 3F-3I, 7, 13-25).

In some cases, the agent used in the TRUPATH method was first identified by the ADSoRB method. The advantage to using ADSoRB and TRUPATH together as a single platform allows for the initial screening of large libraries and validation of signaling properties using the same engineered complexes (e.g. GPCR-Gα(Rluc), fused or unfused). Additionally, the properties determined from TRUPATH can be compared to non-tagged "native" transducers (unfused) in other standard signaling assays and is therefore cross-platform compatible (FIG. 12). Therefore, in some embodiments, the system comprises a pre-determined GPCR-Gα (Rluc) fusion used in the ADSoRB method to identify the agent being tested. In other cases, the GPCR-Gα(Rluc) fusion composition used in the ADSoRB method was first identified by the TRUPATH method. This interplay between disclosed systems enables identification of pathway preferences that can then be used to guide the ADSoRB screen and target agents with the desired transducer bias. Such agents can then be tool molecules or lead compounds in therapeutic strategies.

In some cases where no chemical matter or information on potential transducer pathways is available (e.g. understudied and orphan GPCRs), TRUPATH can be used to identify potential pathway coupling by evaluating receptor constitutive activity across all pathways. Given the multi-state model of GPCR function and the assumption that basal active states couple to many signal transducers, variability in baseline BRET responses (i.e. constitutive activity) should be apparent across different G proteins for GPCRs. As shown in FIG. 5A, TRUPATH assays report constitutive activity and are sensitive to inverse agonists. When tested across all transducers it is indeed apparent that TRUPATH sensors can identify potential coupling mechanisms in the absence of ligand as demonstrated via the dopamine receptors (FIG. 8). Another option would be to use known regulators of basal signaling (e.g. sodium ions). Basal activity of GPCRs like mu-opioid receptors are negatively regulated by sodium (FIG. 9). Altering the sodium concentration of a buffer or drug solution can therefore alter the basal activity and produce an effect on the basal BRET response at different concentrations. Using the disclosed fusion approach is optimal, but not required, as it can eliminate potential effects of endogenous receptor systems on the TRUPATH biosensor. Thus, changes in basal BRET can be attributed to the fused system by eliminating otherwise interfering partners. The unfused format can increase throughput at the potential expense of some of this specificity.

In some cases, it is necessary to standardize receptor expression in membranes or similar environments (e.g. lipo- or nanodiscs) in the ADSoRB approach. Because not all receptors have useful probes for determining expression of functional protein, use of a GPCR-Gα(Rluc) chimera is key. Specifically, the GPCR-Gα(Rluc) chimera from TRUPATH can be incubated with the luminescent substrate to assess relative expression. Comparing luminescence from dilutions of material against luminescence of material which has had expression already determined via a conventional method such as radioligand binding, the amount of previously undetectable receptor (and therefore receptor/transducer complex) can be interpolated (FIG. 10).

In some cases, the GPCR-Gα(Rluc) donor chimera can be used to assess interacting partners via isolation (e.g. immunoprecipitation) and mass spectrometry, and then validated by using a fluorescent acceptor tagged to identified partners. The ability for these interacting partners to modulate affinity of the complex can be probed using the ADSoRB approach.

The details of one or more embodiments of the invention are set forth in the accompanying drawings and the description below. Other features, objects, and advantages of the invention will be apparent from the description and drawings, and from the claims.

DESCRIPTION OF DRAWINGS

As shown in FIG. 2E, the antagonist [H]Naloxone binds poorly to both the MOR and MOR-Gαi1 membranes (black segment), and as a result very little antagonist is eluted from both membranes (small red segments) when treated with GPPNHP. By contrast, the agonist [³H]DAMGO in FIG. 2F binds more strongly to the MOR-Gαi1 complex (note smaller unbound fraction in black) and elutes to a greater extent when treated with GPPNHP (larger red segment for MOR-Gαi1 vs. MOR).

FIG. 3A shows Bioluminescence Resonance Energy Transfer (BRET) between chimeric Gα-RLuc8 donor proteins and Gγ-GFP2 acceptor proteins can differentiate between inactive (intact, high BRET) and active (dissociated, low BRET) Gαβγ heterotrimers. Receptor-mediated rearrangement or dissociation of the Gαβγ heterotrimer represents the proximal step in signal transduction (black arrow). FIG. 3C details that to develop next-generation Gα-RLuc8/Gβγ-GFP2 BRET biosensors, we first combined information from atomic-level protein structures, previous data, and computer-generated models to identify candidate regions of the Gα-subunit amenable to luciferase insertion. FIG. 3D outlines that luciferase chimeras were generated at each position within these defined regions (Gαq insertional sites listed as examples). FIG. 3E shows how the performance of each Gα-RLuc8 chimera was assessed as the first step in an exhaustive optimization scheme to select optimal Gα-RLuc8/Gβγ-GFP2 biosensors. Specifically, in FIG. 3F first-pass screens of different Gα-Rluc8 chimers using a standard Gβγ-GFP2 acceptor (e.g., Gβ1γ2-GFP2) and model GPCR identified the construct with the greatest dynamic range. The top five constructs were confirmed in secondary screens. In a second step FIG. 3G, the top-performing Gα-Rluc8 construct was screened against each of 12 Gγ-GFP2 constructs to identify the optimal acceptor fusion protein. Lastly in FIG. 3H, optimal Gα-Rluc8 donor/Gγ-GFP2 acceptor pairs were screened against each of four major Gβ subunits to determine the final composition of the Gα-RLuc8/Gβγ-GFP2 heterotrimer (FIG. 3I). At all stages of optimization, the construct with the greatest mean amplitude (NET BRET or Baseline-Emax) was selected and advanced forward. All concentration-response curves were fit to a three-parameter logistic equation.

FIGS. 4A to 4C compares traditional unfused BRET assays (FIG. 4A) and new Receptor-G protein RLuc8 fusion (FIG. 4B) at different stoichiometries of donor:acceptor DNA. FIG. 4C shows that fusion BRET system (MOR-Gαi1) can detect partial and superagonists relative to morphine (100%).

FIG. 6C shows that TRUPATH provides potential leverage for difficult targets like the serotonin-5A receptor (HTR5A) that does not work reproducibly in GloSensor cAMP assays. In addition to kinetic effects, the HTR5A-Gαi1 RLuc fusion gives a reliable and substantial serotonin response in BRET.

FIG. 8A shows relative basal activity (% Basal BRET-Emax of control) at DRD1-5 across all TRUPATH sensors. Raw BRET values for Gi1 (FIG. 8B), Gustducin (FIG. 8C), G13 (FIG. 8D), and GsS (FIG. 8E) showing variation in the basal BRET values between transducers.

FIG. 11A (right graph) illustrates a fusion approach where the 5-HT2A receptor fused to Gq (red cartoon) is expressed in cells to confer responsiveness to 5-HT agonists. This provides an important stoichiometry between the receptor and its immediate effector (i.e., selectivity) and showcases the function of GPCR-transducer fusions. Responses to agonists are nearly identical to what is observed in the non-fused scenario (i.e. when only the 5HT receptor is introduced, inset).

FIGS. 12A to 12D show Mu opioid receptor (OPRM) signaling at Gi1 and Gz (both Gi class transducers) appears significantly different. FIG. 12A to 12B show the findings of enhanced efficacy at Gz for morphine (classic agonist) and surprisingly for naloxone (classic antagonist). FIGS. 12C and 12D show partial agonism of naloxone confirmed in a second messenger assay (inhibition of cAMP).

FIG. 13A shows results of primary screen of experimental Gαi1-RLuc8 fusion constructs (two technical replicates). Top-5 performing chimeras (91, 93, 95, 98, 99, boxes) were evaluated in a secondary screen (FIG. 13B, three biological replicates), where AA position 91 (box) was selected as the optimal biosensor construct. A screen of Gγ-GFP2 constructs (FIG. 13C, three biological replicates) identified Gγ9-GFP2 and Gγ13-GFP2 (boxes) as top performing GFP-acceptor proteins. A screen of these two Gγ-GFP2 constructs comparing the performance of Gβs 1-4 (FIG. 13D, three biological replicates) identified Gβ3/Gγ9-GFP (box) as the optimal acceptor dimer composition for the Gα1 TRUPATH sensor. Data are presented as mean t SEM.

FIG. 14A shows results of primary screen (two technical replicates), FIG. 14B shows top-5 performing chimeras (boxed), FIG. 14C shows screen of Gγ-GFP2 constructs, FIG. 14D shows results of screen against Gβs 1-4. Top performing biosensor compositions are shown in Table 1. Data are presented as mean±SEM.

FIG. 15A shows results of primary screen (two technical replicates), FIG. 15B shows top-5 performing chimeras (boxed), FIG. 15C shows screen of Gγ-GFP2 constructs, FIG. 15D shows results of screen against Gβs 1-4. Top performing biosensor compositions are shown in Table 1. Data are presented as mean±SEM.

FIG. 16A shows results of primary screen (two technical replicates), FIG. 16B shows top-5 performing chimeras (boxed), FIG. 16C shows screen of Gγ-GFP2 constructs, FIG. 16D shows results of screen against Gβs 1-4. Top performing biosensor compositions are shown in Table 1. Data are presented as mean±SEM.

FIG. 17A shows results of primary screen (two technical replicates), FIG. 17B shows top-5 performing chimeras (boxed), FIG. 17C shows screen of Gγ-GFP2 constructs, FIG. 17D shows results of screen against Gβs 1-4. Top performing biosensor compositions are shown in Table 1. Data are presented as mean t SEM.

FIG. 18A shows results of primary screen (two technical replicates), FIG. 18B shows top-5 performing chimeras (boxed), FIG. 18C shows screen of Gγ-GFP2 constructs, FIG. 18D shows results of screen against Gβs 1-4. Top performing biosensor compositions are shown in Table 1. Data are presented as mean±SEM.

FIG. 19A shows results of primary screen (two technical replicates), FIG. 19B shows top-5 performing chimeras (boxed), FIG. 19C shows screen of Gγ-GFP2 constructs, FIG. 19D shows results of screen against Gβs 1-4. Top performing biosensor compositions are shown in Table 1. Data are presented as mean t SEM.

FIG. 20A shows results of primary screen (two technical replicates), FIG. 20B shows top-5 performing chimeras (boxed), FIG. 20C shows screen of Gγ-GFP2 constructs, FIG. 20D shows results of screen against Gβs 1-4. Top performing biosensor compositions are shown in Table 1. Data are presented as mean±SEM.

FIG. 21A shows results of primary screen (two technical replicates), FIG. 21B shows top-5 performing chimeras (boxed), FIG. 21C shows screen of Gγ-GFP2 constructs, FIG. 21D shows results of screen against Gβs 1-4. Top performing biosensor compositions are shown in Table 1. Data are presented as mean±SEM.

FIG. 22A shows results of primary screen (two technical replicates), FIG. 22B shows top-5 performing chimeras (boxed), FIG. 22C shows screen of Gγ-GFP2 constructs, FIG. 22D shows results of screen against Gβs 1-4. Top performing biosensor compositions are shown in Table 1. Data are presented as mean±SEM.

FIG. 23A shows results of primary screen (two technical replicates), FIG. 23B shows top-5 performing chimeras (boxed), FIG. 23C shows screen of Gγ-GFP2 constructs, FIG. 23D shows results of screen against Gβs 1-4. Top performing biosensor compositions are shown in Table 1. Data are presented as mean t SEM.

FIG. 24A shows results of primary screen (two technical replicates), FIG. 24B shows top-5 performing chimeras (boxed), FIG. 24C shows screen of Gγ-GFP2 constructs, FIG. 24D shows results of screen against Gβs 1-4. Top performing biosensor compositions are shown in Table 1. Data are presented as mean±SEM.

FIGS. 25A to 25D show workflow and data supporting successful optimization of Gα13 BRET biosensor. Format follows that of FIG. 13. Briefly, FIG. 25A shows results of primary screen (two technical replicates), FIG. 25B shows top-5 performing chimeras (boxed), FIG. 25C shows screen of Gγ-GFP2 constructs, FIG. 25D shows results of screen against Gβs 1-4. Top performing biosensor compositions are shown in Table 1. Data are presented as mean t SEM.

FIG. 26A shows that for difficult to engineer Gα transducers (e.g., Gα11), a new site for RLuc8 insertion was identified between the α4-strand and the α3 helix of the Ras-like domain (Switch III, dashed box). The closest residue in the Gα11 model (a glutamic acid at position 241, FIG. 26A inset) was first targeted to assess the performance of RLuc8 chimeras generated within this region. FIG. 26B delineates the Switch III region within Gα11 for RLuc8 insertion.

FIG. 26C compares an optimized alpha helical Gq biosensor and a Switch III version of Gq; note ~50% enhancement in signal for Switch III. High performance of luciferase insertions within Switch III should extend to all sensors in Table 1.

FIGS. 29A to 29N show direct head-to-head comparisons of the reference constructs (black) to the final TRUPATH suite of biosensors (purple). Fold difference in amplitude was analyzed as a two-tailed t-test between reference and TRUPATH biosensors (Table 2). Different model receptor systems were used for the comparisons. Performance of GαRLuc8/Gβγ-GFP2 BRET sensors were as follows: FIG. 29A (Reference) Gαi1-92-Rluc8/Gβ1γ2-GFP2<(TRUPATH) Gαi1-91-Rluc8/Gβ3γ9-GFP2, p<0.0001. FIG. 29B (Reference) Gαi2-92-Rluc8/Gβ1γ2-GFP2<(TRUPATH) Gαi2-91-Rluc8/Gβ3γ8-GFP2, p<0.0001. FIG. 29C (Reference) Gαi3-92-Rluc8/Gβ1γ2-GFP2<(TRUPATH) Gαi3-99-Rluc8/Gβ3γ9-GFP2, p<0.0001. FIG. 29D (Reference) GαoA-92-Rluc8/Gβ1γ2-GFP2<(TRUPATH) GαoA-92-Rluc8/Gβ3γ8-GFP2, p=0.0007. FIG. 29E (Reference) GαoB-92-Rluc8/Gβ1γ2-GFP2<(TRUPATH) GαoB-92-Rluc8/Gβγ8-GFP2, p=0.0003. FIG. 29F (Reference) GαZ-92-Rluc8/Gβ1γ2-GFP2<(TRUPATH) GαZ-114-Rluc8/Gβ3γ1-GFP2, p<0.0001. FIG. 29G (Reference) GαGustducin-92-Rluc8/Gβ1γ2-GFP2<(TRUPATH) GαGustducin-117-Rluc8/Gβ3γ1-GFP2, p<0.0001. FIG. 29H (Reference) GαsS-100-Rluc8/Gβ3γ9-GFP2<(TRUPATH) GαsS-123-Rluc8/Gβ3γ9-GFP2, p<0.0001. FIG. 29N (Reference) Gα13-107-Rluc8/Gβ1γ2-GFP2<(TRUPATH) Gα13-126-Rluc8/Gβ3γ9-GFP2, p<0.0001.

FIG. 30C details the functionality and enhanced response of the Gαi3-99-Rluc8/Gβ13γ2-GFP2 triple plasmid vs. the same components transfected as separate plasmids. Shown are concentration-response curves for the MOR activated by DAMGO.

FIG. 3I shows that the robust signal of TRUPATH biosensors enables miniaturization to 384-well plates. Head-to-head comparison of GαZ-114-Rluc8/Gβ3γ1-GFP2 biosensor for 96-well (top) and 384-well (bottom) plate formats. Shown are concentration-response curves for the neurotensin receptor activated by neurotensin peptide (8-13). The NET BRET response at GαZ was 0.495 for the 96-well plate and 0.625 for the 384-well plate. Neurotensin potency was 1.85 nM and 1.68 nM for 96- and 384-well plates, respectively.

FIGS. 32A to 32J demonstrate how a panel of KOR agonists engage Gαi/o-class TRUPATH sensors with varying potency (FIG. 32A heatmap) and efficacy (FIG. 32B heatmap). Responses were not detected at other G proteins. Concentration-response curves for Salvinorin A (FIG. 32C), U69,593 (FIG. 32D), GR89,696 (FIG. 32E), BU74 (FIG. 32F), dynorphin A (FIG. 32G), ML139 (FIG. 32H), diprenorphine (FIG. 32I), and RB64 (FIG. 32J) reveal ligand-dependent shifts in transducer activity. Most ligands exhibit enhanced (GαZ) and diminished (GαGustducin) potencies relative to other G protein transducers. While many ligands activated all transducers with equal efficacy (Salvinorin A, U69,593, GR89,696, ML139, and RB64), others exhibited efficacy bias (BU74, dynorphin A, and diprenorphine). Data presented as mean values±SEM. Heatmap colors represent mean Log EC50 and efficacy values.

FIG. 33A shows efficacy values (% control) for dopamine concentration-response curves for DRD1-5 across the full TRUPATH platform. FIG. 33B shows potency values (log EC50) for dopamine concentration-response curves for DRD1-5 across the full TRUPATH platform. FIG. 33C shows dopamine concentration-response curves for DRD1-5 at Gz. FIG. 33D shows transducer concentration-response curves for dopamine responses at DRD5.

DETAILED DESCRIPTION

Figure 1:
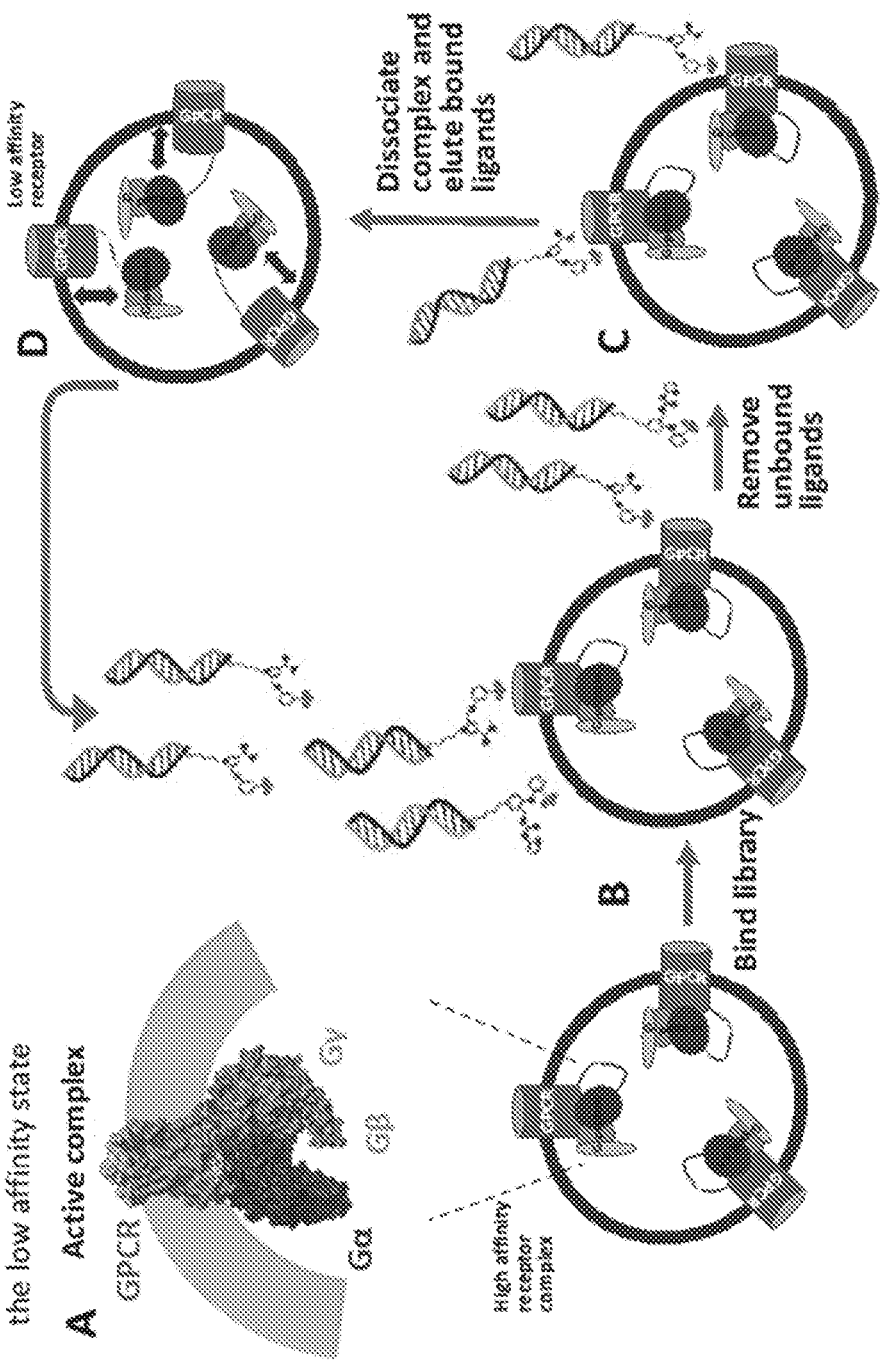
FIG. 1 is a schematic of an example embodiment of the disclosed ADSoRB (Affinity-Directed Selection of Receptor Binders) screening system. Various agent libraries can be substituted in place of the nucleic acid-encoded library shown here. Steps including purification and immobilization of the GPCR-transducer complex (A), library binding (B), washing (C), and elution (D) are subject to modification as described herein. A major differentiation here is the functional elution step, which consists of dissociating the signaling complex in real time (arrows in D) and effectively shifts the receptor from high to low affinity states. Ligands that prefer the high affinity state of the receptor (e.g. in complex with a transducer) will dissociate faster from the low affinity receptor. Agonists have a large preference for binding the active receptor state that is equivalent to the magnitude of their signaling in cells.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The process of ligand-mediated formation and subsequent dissociation of GPCR-Transducer signaling complexes correlates with receptor activation and downstream responses in cells. These complexes can consist of native transducer proteins and/or those consisting of a "fusion" or "chimeric" transducer which contains or is fused to a BRET-like donor enzyme (e.g. *Renilla* luciferase, RLuc) or a BRET or FRET acceptor (e.g. GFP2). The disclosed system is distinguished in part by the implementation of real time signaling complex formation and dissociation as a way to recapitulate signaling outside of a cellular context (i.e. in vitro) and measure activation of single pathways within a cell without the requirement for second messenger detection. The dynamic signaling complexes claimed may exist unfused or fused. This conceptual framework provides significant advantages detailed herein.

The invention is further separated into two components: ADSORB ("Affinity Directed Selection of Receptor Binders") primarily for large-scale, ultra-high throughput in vitro drug screening and TRUPATH (for TRansdUcerome Profile Analysis of g protein paTHways) for cellular drug screening and signaling assays.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

It must be noted that, as used in the specification and the appended claims, the singular forms "a," "an," and "the" include plural referents unless the context clearly dictates otherwise.

The term "polynucleotide barcode" or "barcode" or "polynucleotide tag" are used interchangeably and, according to the present disclosure, as used herein refer to a sequence of nucleotides, i.e., an oligonucleotide, an oligomer, or an oligo. According to the present disclosure a barcode is attached to a subject molecule. An attached polynucleotide barcode finds use in tagging or labeling a single macromolecule, e.g., a polynucleotide, a polypeptide, a ribonucleoprotein, a carbohydrate, a lipid, a complex, and the like. A single polynucleotide barcode also finds use in tagging or labeling a plurality of macromolecules, e.g., a group of related polynucleotides, a group of related polypeptides, a group of related ribonucleoproteins, a group of related carbohydrates, a group of related lipids, a group of related complexes, and the like. Unique barcodes are used to individually differentiate members of a group from one another, e.g., unique barcodes attached to individual ribonucleoproteins serves to individually differentiate each ribonucleoprotein from every other ribonudeoprotein. Unique barcodes are also used to differentiate groups of related members, e.g., derived from the same species, derived from the same individual, derived from the same library, derived from the same experiment, derived from the same sample, etc., from other groups. For example, the same unique barcode is attached to a first plurality of related ribonucleoproteins and a second unique barcode is attached to a second plurality of related ribonucleoproteins such that when the first and second pluralities of related ribonucleoproteins are mixed the barcodes serve to indicate the group to which each ribonucleoprotein belongs. A polynucleotide barcode may be of any useful length, e.g., about 1-100 nucleotides, about 5-10 nucleotides, about 10-15 nucleotides, about 10-18 nucleotides, about 18-25 nucleotides, or about 25-50 nucleotides, depending on the particular contexts in which the barcode is being used and how many individual members or individual groups are preferably differentiated. In certain instances the barcode is between about 17 to about 22 nucleotides in length, e.g., about 17 nucleotides, about 18 nucleotides, about 19, nucleotides about 20 nucleotides, about 21 nucleotides, or about 22 nucleotides. For example, the use of a barcode about 1 nucleotide in length differentiates 4 individual members or groups, about 2 nucleotides in length differentiates 16 individual members or groups, about 3 nucleotides in length differentiates 64 individual members or groups, about 4 nucleotides in length differentiates 256 individual members or groups, about 5 nucleotides in length differentiates 1024 individual members or groups, and so on. Thus the use of a barcode over about 9 nucleotides in length differentiates over 1 million unique individual members or groups and a barcode over about 14 nucleotides in length differentiates over 1 billion unique individual members or groups.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

A "spacer" or "linker" as used herein refers to a peptide that joins the proteins comprising a fusion protein. Generally, a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule. Additionally, linkers may be selected which comport some new functionality to the fusion (e.g. a phosphorylatable region).

Luciferase here is used as a generic stand-in for any enzyme or protein which can, through chemical or enzymatic reaction, produce light (e.g. luminescence).

For the purposes of the mechanism employed in TRUPATH, a luminescent enzyme can be replaced with a fluorescent protein to convert the technique from BRET to FRET.

The location of the "donor" protein and "acceptor" protein is interchangeable between the subunits of the heterotrimer but is discussed in terms of the donor being fused to the Gα and the acceptor on the Gγ for purposes of simplicity.

Figure 11A:
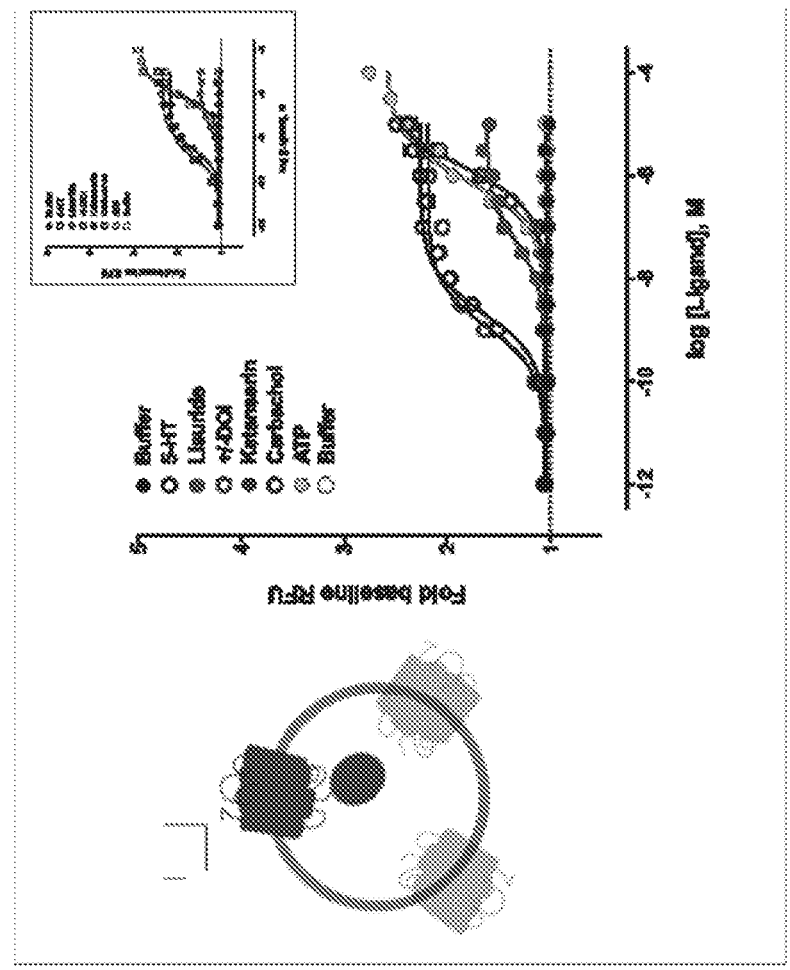
FIG. 11A (left panel) illustrates that GPCR-transducer fusion proteins are functional for a variety of receptors and pathways and faithful to known GPCR coupling preferences. Here are HEK293 cells that endogenously express Gq-coupled purinergic (ATP-activated) and muscarinic (Carbachol-activated) receptors, but not serotonin (5-HT) receptors. Thus 5-HT receptor agonists (5-HT, DOI, Lisuride) do not cause calcium release in these cells (left graph).
Figure 11A:
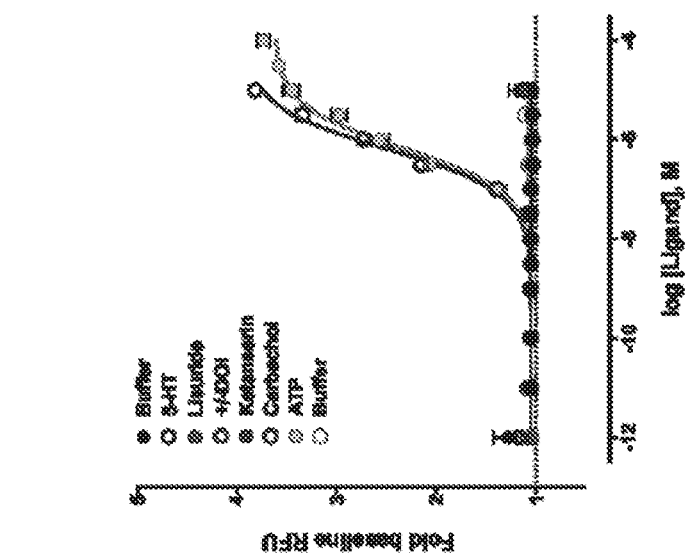

Disclosed herein is a screening platform that in some embodiments involves fusion proteins comprised of G protein coupled receptors (GPCRs) fused to a transducer, such as a native or engineered G protein α subunit (Gα), arrestin, or a signaling associated protein (e.g. a scaffolding protein, complex, or a protein or protein fragment that induces inactive or active structural changes in the receptor). In some cases, the GPCR and transducer are connected by a flexible linker. By fusing the transducer to the receptor, the system has a 1:1 local stoichiometry, maintains appropriate membrane trafficking, and has increased fidelity to the expressed receptor/transducer pathway (FIG. 11A,B). For ADSoRB, fusion proteins ensure a stable complex due to high local concentration of tethered transducer.

All eukaryotes use G proteins for signaling, resulting in a large diversity of G proteins. For example, the human genome encodes roughly 800 GPCRs, 18 different Gα proteins, 4 major Gβ proteins, and 12 Gγ proteins (FIG.

11C). It is understood that the disclosed platform can involve any available combination of these or other mammalian GPCR and suitable transducers from the same or different species. Nucleic acid and amino acid sequences for GPCRs and transducer are known and available for use in the disclosed systems.

For use in the disclosed TRUPATH and ADSoRB methods, the Gα subunit of the disclosed fusion protein can also be tagged with a fluorescent/luminescent donor or acceptor. In these embodiments, if the Gα protein subunit is tagged with a fluorescent/luminescent donor, then either a Gβ protein subunit or a Gγ protein subunit is tagged with a fluorescent acceptor, and if the Gα protein subunit is tagged with a fluorescent acceptor, then either a Gβ protein subunit or a Gγ protein subunit is tagged with a fluorescent/luminescent donor.

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics. Chimeric mutant proteins occur naturally when a large-scale mutation, typically a chromosomal translocation, creates a novel coding sequence containing parts of the coding sequences from two different genes.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a functional fusion protein or chimera. Function of the GPCR-transducer fusion proteins and select G protein-RLuc8 chimeras disclosed herein is shown in FIGS. 4, 11, 12, 27, and 28.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. Synthesis of the fused cDNA sequence can also yield a recombinant fusion protein. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected (see below). Especially in the case where the linkers enable protein purification, linkers in protein or peptide fusions are sometimes engineered with cleavage sites for proteases or chemical agents which enable the liberation of the two separate proteins. This technique is often used for identification and purification of proteins, by fusing a GST protein, FLAG peptide, or a hexa-his peptide (aka: a 6×his-tag) which can be isolated using nickel or cobalt resins (affinity chromatography). Chimeric proteins can also be manufactured with toxins or anti-bodies attached to them in order to study disease development.

Linkers are any flexible amino-acid sequence including but not limited to the following examples:

```
TANGO Linker:
                                       (SEQ ID NO: 2)
DTGGRTPPSLGPQDESCTTASSSLAKDTSSTGENLYFQL;

Small Linker:
                                       (SEQ ID NO: 3)
SGGGS;

Medium Linker:
                                       (SEQ ID NO: 4)
GGGGSADIAAAKAGGGGS;
and Long Linker
                                       (SEQ ID NO: 5)
GGGGSADIAAAKAGGGGSGGGGSADIAAAKAGGGGS.
```

Alternatively, internal ribosome entry sites (IRES) elements can be used to create multigene or polycistronic messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Samow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (U.S. Pat. Nos. 5,925,565 and 5,935,819; PCT/US99/05781). IRES sequences are known in the art and include those from encephalomycarditis virus (EMCV) (Ghattas, I. R. et al., Mol. Cell. Biol., 11:5848-5849 (1991); BiP protein (Macejak and Samow, Nature, 353:91 (1991)); the Antennapedia gene of drosophilia (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)).

ADSoRB is a screening strategy that relies on the differential abilities of ligand classes (e.g. agonists, antagonists, inverse agonists, allosteric modulators) to recognize or interact with different receptor states (e.g. native/unliganded, liganded, active, inactive, mutant, transducer or signaling mimetic-stabilized) (FIG. 1). Ligands here may consist of small-molecules, biologics (e.g. proteins, peptides, antibodies, nanobodies, nucleic acids, aptamers, and derivatives) or chimeras thereof. Ligands may or may not be "tagged" by identifiers (barcodes) such as nucleic acids or known protein sequences for subsequent identification (e.g. via deep-sequencing, protein or small molecule mass spectroscopy, phage titering, protein microarrays, etc). By exploiting the magnitude of ligand preferences for different transducer-induced affinity states, ligand classes can be identified and segregated. Specifically, the pharmacological output of the screen can be established through the differential affinities (i.e. preferences) for these active and inactive target states through the standard concepts of allostery and biased agonism. The ADSoRB method differs from current in vitro and cell-based screening approaches that are limited to only identifying ligands that physically bind static or irreversibly conformationally constrained target proteins. Not to be exhaustive, these include static approaches that screen complex library mixtures using i) non-specific elution strategies and unliganded or stabilized receptors, ii) cell sorting to separate ligand classes, and iii) biophysical methods. These static approaches (i.e. the same target receptor does not change affinity states as part of the method) do not differentiate between receptor conformational states that, when modulated in real time as in ADSoRB, permit the isolation of ligands with a pre-defined pharmacology. Thus, unlike current technologies, ADSoRB is a dynamic method that switches between the transducer-coupled receptor and the inactive/transducer-uncoupled receptor to control the pharmacology of the screened ligands. Modulating receptor or target conformational states by dynamic association with different transducers enables the first rational method to specifically target biased agonists in vitro. Given that allostery is a fundamental aspect of protein function, it is conceivable that ADSoRB could be applied to other proteins (e.g. kinases or transcription factors) to find new ligands with predetermined functional effects. Moreover, the utilization of allostery here includes other reversible receptor stabilization approaches that enable on-demand switching of conformational states. The general process of ADSoRB as it relates to GPCRs is described below:

Target screening complexes (GPCR-transducer fusion proteins) are produced in a biological or in vitro system. The target can be prepared by a membrane preparation (e.g. released, separated, or sequestered in microsomes) or by a purification and isolation strategy (e.g. immuno or chemical purification methods, nano- or lipodisc, detergent micelle, liposomal, or lipidomimetic environment, with or without the use of further purification or isolation methods). The target preparation may or may not be oriented to expose different receptor surfaces for screening.

Figure 10:
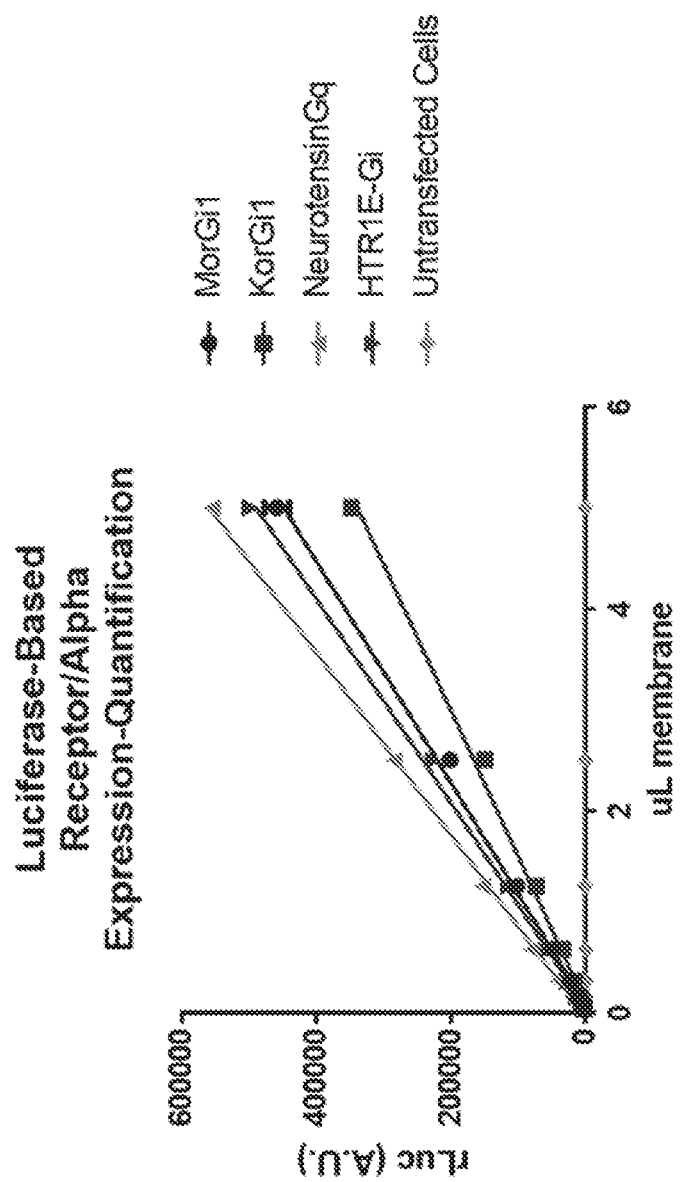
FIG. 10 shows how receptor-transducer(RLuc) fusions in membranes/microsomes can be used quantify receptor density for ADSoRB. Presented are receptor-Galpha(RLuc8) fusions with known radiolabeled probes that can be used to quantify their expression and then be used as standard curves for receptors with no probes. As shown here, plots of receptor density (e.g. via radiolabeled saturation binding) vs. luciferase activity can quantify the expression levels of understudied receptor-transducer fusion proteins. For "orphan" receptors or other receptors lacking radioligands, luminescence values from the receptor-transducer-Rluc preparation can be compared to a standard curve and the receptor-density extrapolated due to the 1:1 receptor/G-alpha-transducer stoichiometry. This ensures equal receptor density for screening in the ADSoRB approach.

The target complexes may or may not be (depending on requirements of assay) immobilized (e.g. bound to affinity bead resin, magnetic resin, column, plate, flow-cells, SPR chips, arrays) or used in the "raw" or crude form (e.g. collected by standard methods of centrifugation or filtration). The tethered transducer may consist of the "tagged" (e.g. *Renilla* luciferase) or native form and need not be a G protein (transducer here also refers to other proteins and methods to reversibly stabilize receptor states). The "tagged" form may be used to quantify expression or target yield against known standards as some targets lack tools or methods to quantify their expression or yield. This may be done as follows (but is not exclusive to the following method). A known tagged-receptor-transducer fusion is expressed and quantified by methods such as radioligand saturation binding. Via titration, this standard is diluted and probed with a substrate for the tagged luciferase to determine the relationship between luminescence and unit of target determined by standard methods. The "unknown" tagged target is similarly titrated in the luciferase assay to determine the relative concentration or yield by interpolation of the standard curve derived from the known standard (FIG. 10).

Targets are exposed to (i.e. treated or screened with) ligand libraries (collections curated or otherwise, natural product extracts or tissue preparations)—this may consist of incubations of varying duration, washing or otherwise flowing ligands across or through the target preparation. The flow-through/un-bound fraction of the library can be collected for further analysis or subsequent screening (e.g. as a negative selection tool). The "treated" target may or may not be washed to identify "stronger" or more selective interacting ligands or to create a more stringent selection strategy— all flow-through from wash-stages may be captured for analysis as in the initial eluate.

In an important distinguishing step that has not been disclosed in other screening methods and that provides control over ligand pharmacology (i.e. to isolate in a targeted fashion agonists, biased agonists, positive allosteric modulators, and others) bound or interacting ligands are functionally eluted by incubating complexes with inhibitors of GPCR-transducer interactions (e.g. guanine nucleotides and other chemical derivatives for G-proteins; inhibitors of arrestin association like arrestin loop peptides; antibodies or other biomimetics that compete for binding surfaces, G protein peptide fragments, or engineered domains that change protein structure) (FIG. 2). Heat, chemical denaturants such as acids, bases, urea, methanol, or detergents (nonspecific agents) or competing small molecules can elute all remaining binders, an important consideration for elution of conformational state-insensitive ligands (e.g. antagonists). Differentiating ADSoRB from current static methods (i.e. when the target is maintained in a single affinity or conformational state/ensemble, such as when thermostabilized), the functional elution strategy of ADSoRB modulates target conformational states in real time to facilitate target ligand dissociation and detection. A major distinction is that conformational state modulation mimics receptor-mediated activation of the tethered transducer in cells, thus recapitulating a cellular activation event in a precisely controlled in vitro environment and solving the problem of in vitro assays lacking function. Such a novel method dismisses and overcomes the notion that functional screening can only be done in cells. As demonstrated in FIG. 2, the ADSoRB method works because GPCRs are allosteric machines that switch between high affinity transducer-coupled states (active) and low affinity uncoupled states (inactive). Balanced and biased signaling is encoded within these state transitions (Strachan R T et al. J Biol Chem. 2014; 289(20):14211-24) (FIG. 28), thus ligands that elute from different GPCR-transducer complexes will exhibit general or biased activation of those different pathways in cells. Ligands that are insensitive to modulation of receptor states can be eluted using nonspecific or biospecific (i.e. a competing ligand) elution techniques after functional elution. Notably, as shown in FIG. 2G, functional elution with GPPNHP can be enhanced by the addition of sub-saturating concentrations of a competitive ligand. Thus, functional elution could also include the combined use of state modulation and competitive inhibition.

Functional analysis of the elution may consist of bulk-screening eluates in signaling assays (e.g. TRUPATH defined in later section, TANGO assay, GTPyS, Promega Glosensor cAMP, FLIPR calcium mobilization assays, radio-labeled inositol trisphosphate accumulation, cAMP accumulation, Ras/Rac/Rho assays, transcriptional reporters, etc.). The specific contents of the eluates may also be identified by deep sequencing of nucleic acid barcodes, protein microarrays, small molecule or protein mass spectroscopy, phage tittering, clonal isolation, or other deconvolution methods. Contents of eluates can also be amplified to subsequently enrich future ligand libraries for subsequent and iterative screening. This multi-round selection strategy is an iterative process to enrich for ligands with preferences for the desired receptor affinity state. Mufti-round selection can also be used as mentioned above for negative selection. The determined selected components of the library can be compiled into a database for other purposes (e.g. computational analysis and deconvolution, subsequent structure activity relationship analysis, artificial intelligence/machine learning for in silico drug discovery and computational sorting and design, or for further iterative screening purposes involving medicinal chemistry). This selection strategy may be used iteratively as needed for as many rounds as required. The information set for each transducer-tethered target can be used to identify differential affinities of the same or different ligands for the different states (hereafter referred to as signaling bias).

Figure 28:
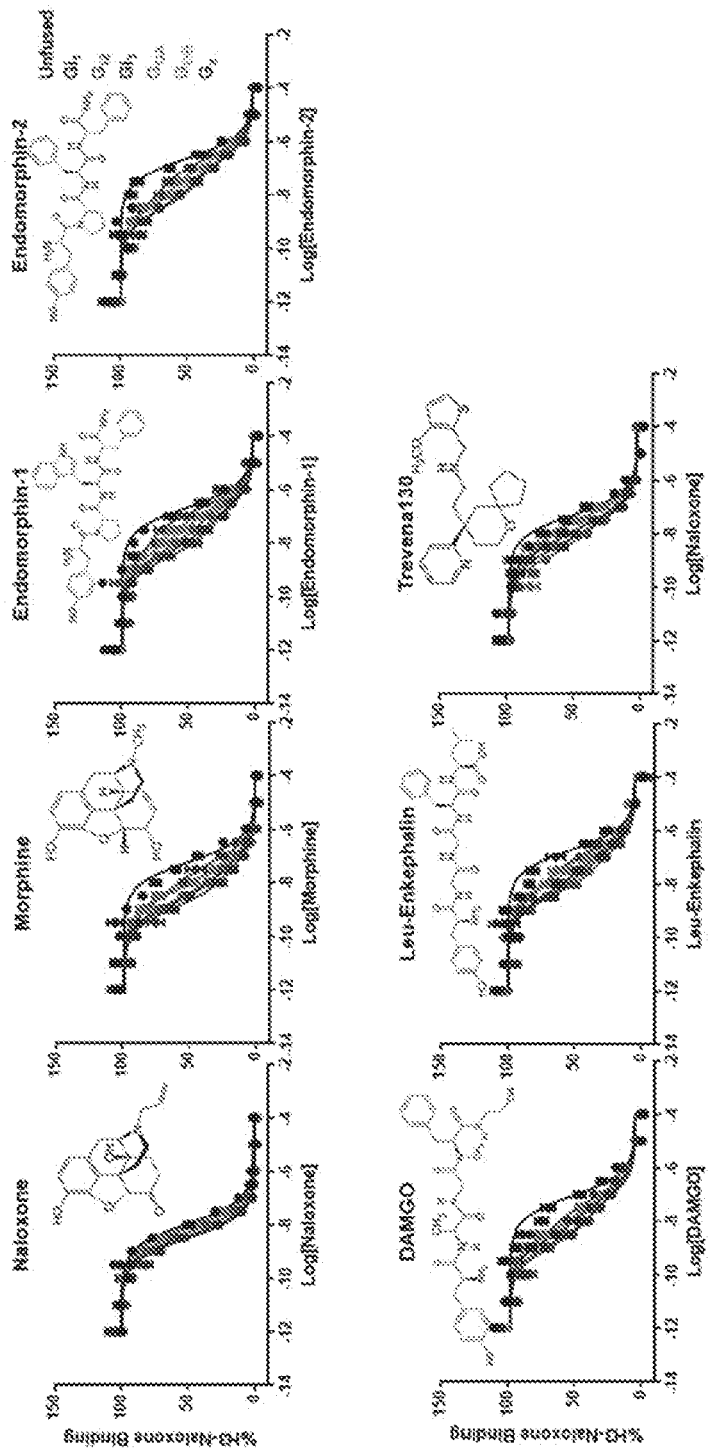
FIG. 28 shows seven ligands screened at six Gα proteins fused to the µ-opioid receptor (MOR). Consistent with classical pharmacology, standard in vitro competition radioligand binding assays report affinity shifts for ligands that correlate with their abilities to activate these pathways in cells, thus supporting the functionality of the fusions. The antagonist naloxone does not experience significant affinity shifts, whereas full agonists (morphine, endomorphins, DAMGO, and Leu-enkephalin) and a partial agonist (TRV130) shift compared to unfused MOR. Differences in shifts (i.e. molecular efficacy) suggest biased responses at these pathways (Strachan R T et al. J Biol Chem. 2014; 289(20):14211-24). The magnitudes of affinity shifts are consistent with ligand activation of pathways in cells (e.g. Gi/o), supporting the biological relevance of GPCR-Gα fusions (i.e. pharmacology is conserved even when Gα is fused to the GPCR). Such differences in ligand preferences for low and high affinity states underlies the theoretical framework of ADSoRB.
Figure 29I:
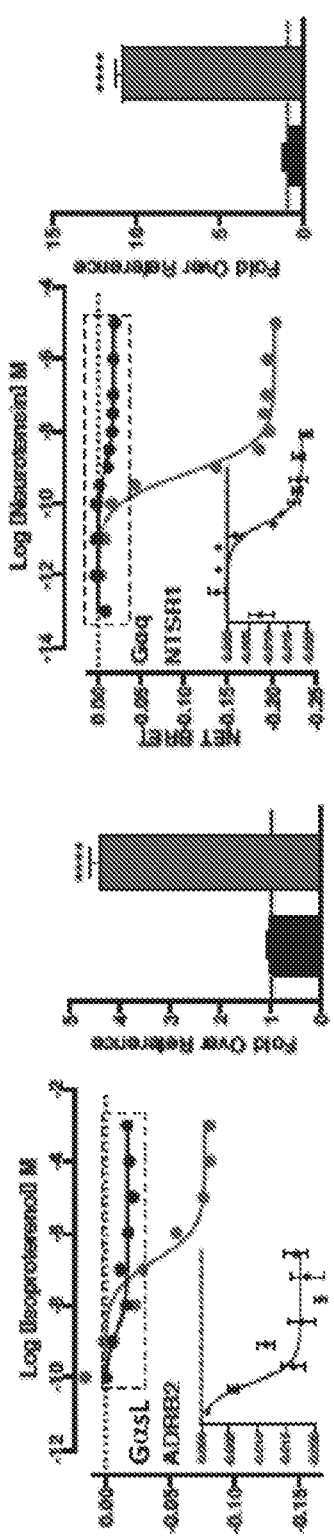
FIG. 29I (Reference) GαsL-114-Rluc8/Gβ1γ1-GFP2<(TRUPATH) GαsL-137-Rluc8/Gβ1γ1-GFP2, p<0.0001.
Figure 29J:
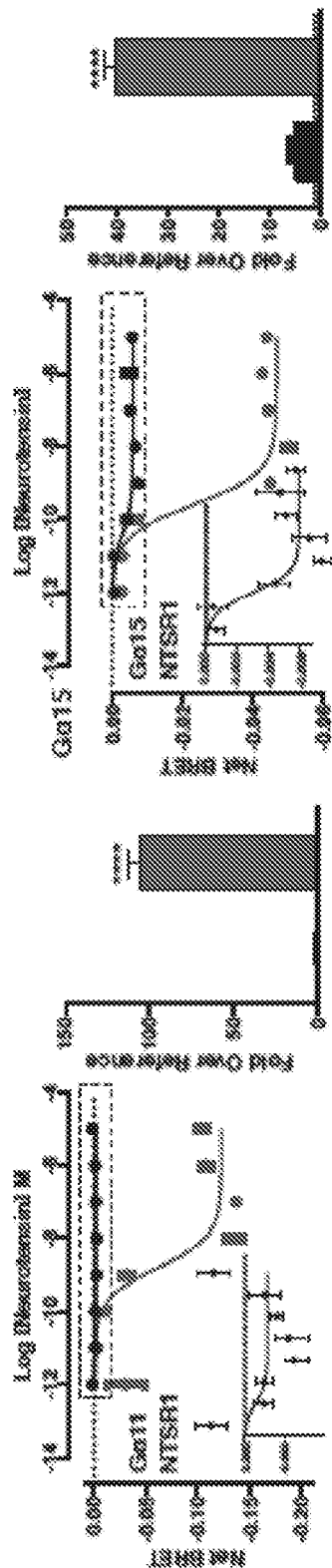
FIG. 29J (Reference) Gαq-98-Rluc8/Gβ1γ1-GFP2<(TRUPATH) Gαq-125-Rluc8/Gβ3γ9-GFP2, p<0.0001.
Figure 29K:
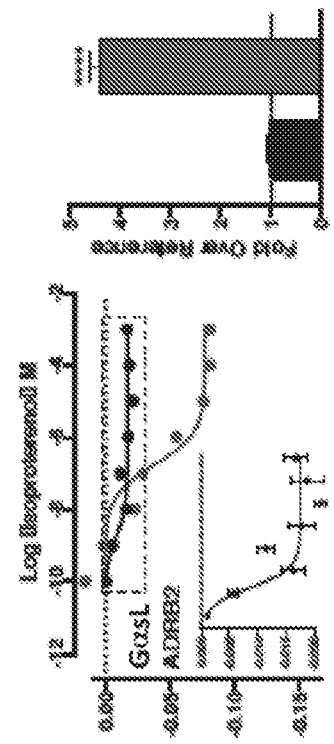
FIG. 29K (Reference) Gα11-98-Rluc8/Gβ1γ1-GFP2<(TRUPATH) Gα11-246-Rluc8/Gβ3γ13-GFP2, p<0.0001.
Figure 29L:
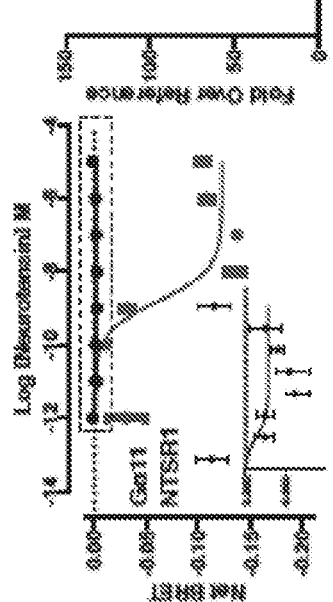
FIG. 29L (Reference) Gα15-101-Rluc8/Gβ1γ2-GFP2<(TRUPATH) Gα15-245-Rluc8/Gβγ13-GFP2, p<0.0001.
Figure 29N:
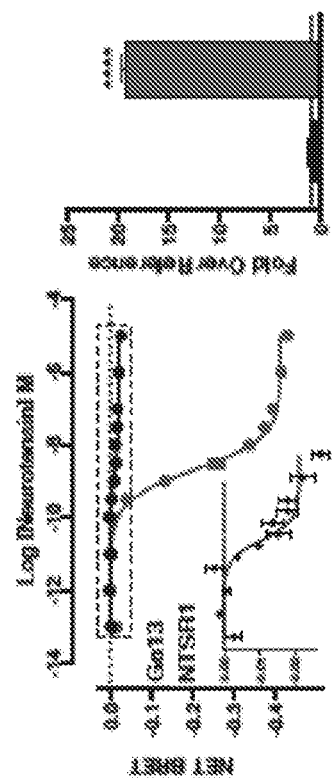
Figure 29M:
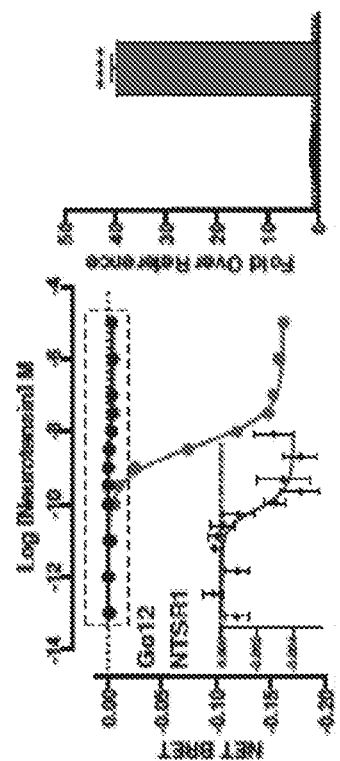
FIG. 29M (Reference) Gα12-115-Rluc8/Gβ1γ2-GFP2<(TRUPATH) Gα12-134-Rluc8/Gβγ9-GFP2, p<0.0001.

As depicted in FIG. 1 and shown in FIG. 2, the differential affinity of agonists for active signaling complexes versus the uncoupled, inactive receptor can be exploited for the isolation of pathway-specific agents (e.g. biased agonists). A fundamental property of G protein-coupled receptor (GPCR) agonists is that they bind 10 to 100× more tightly to active receptors in complex with a transducer through which they can signal compared to the free receptor (FIG. 28). This extends to biased agonists that show a preference for binding to different transducer-coupled receptor states. Following complex dissociation (i.e. uncoupling of the tethered transducer from the GPCR), agonists will bind less tightly to the low affinity state of the receptor which involves an increase in ligand dissociation rate (i.e. it functionally elutes). As shown in panel 1B, under experimental conditions in which an active complex is intact (e.g. immobilized cell membranes expressing a GPCR-G protein fusion), library agents (in this case nucleic acid-tagged small molecules) will bind tightly to the complex and resist washing (FIG. 1C). Upon complex dissociation (i.e. addition of non-hydrolyzable guanine nucleotide, GPPNHP), only library agents that now sense this receptor as being in a low affinity state will dissociate and be collected in the eluate (FIGS. 1D and 2B, 2C, 2E). When appropriate (e.g. for phage, mRNA-peptide, or yeast display libraries), subsequent amplification and rounds of selection will enrich for active complex-specific agonists. An initial cloning platform of over 300 druggable GPCRs and 16 different human G proteins covers known therapeutically-relevant receptor signaling complexes. GPCR-transducer fusions could extend to the remainder of GPCRs and other transducers that are understudied or orphaned (e.g. olfactory and taste receptors), thereby providing complete coverage of GPCR-mediated processes in healthy and diseased humans. GPCRs are also found in other organisms and could be used as targets for other purposes including, for example, agricultural pest control and control of disease vectors (e.g. mosquitoes), and so this approach can extend across species and biological systems and encompass genetic variants to identify selective ligands due to differences in their allostery.

One-shot screening (i.e. using only one round of ADSoRB) of libraries could be achieved using very stringent wash protocols or using microfluidics such as those common to surface plasmon resonance (SPR) machines or those using magnetic beads. Automated immobilization of target complexes, library incubation, washing, functional elution, and recovery of eluted library agents would greatly increase the selectivity and efficiency of ADSoRB screens.

Figure 3A:
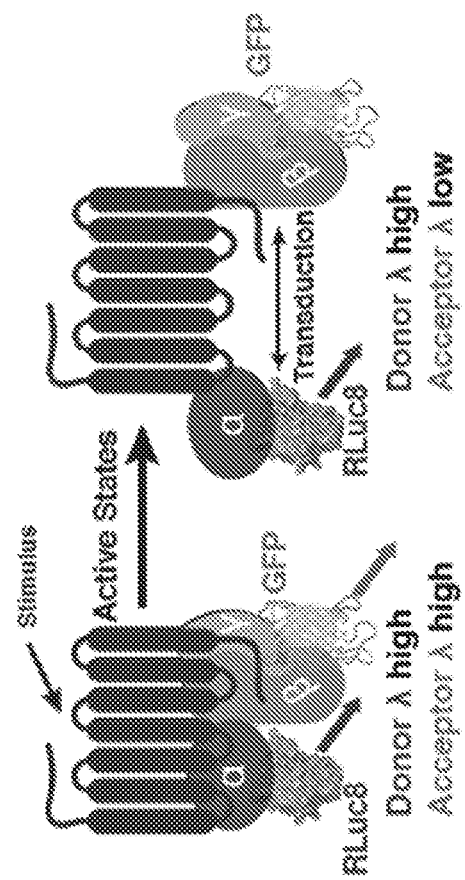
FIG. 3A shows TRUPATH biosensor construction and optimization.
Figure 11B:
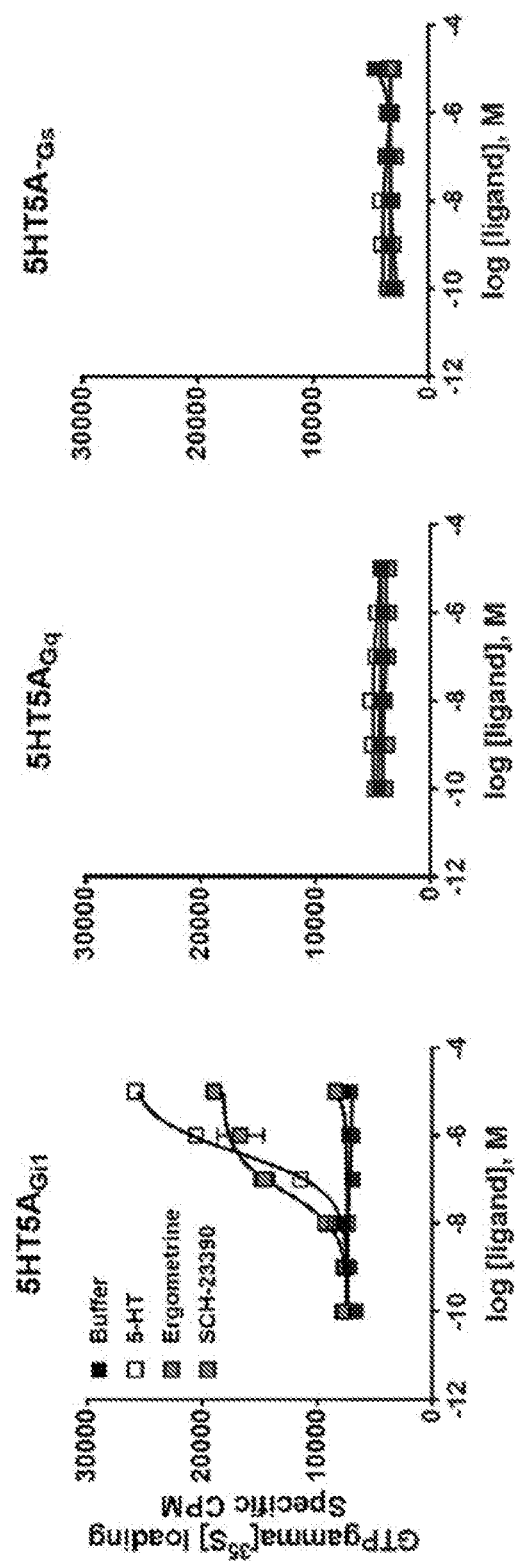
FIG. 11B shows that GPCR-transducer fusions achieve specificity of G protein activation for screening different pathways (Gi vs. Gq vs. Gs, etc.). Here, a radiolabeled non-hydrolyzable GTP analogue ($[^{35}]$GTPyS) is loaded into fused G proteins upon receptor activation by experimental full (5-HT) and partial (Ergometrine) agonists. The nature of the assay is unidirectional as the receptor-mediated incorporation of $[^{35}]$GTPyS is irreversible. As shown for the Gi-coupled 5-HT5A receptor, G protein activation ($[^{35}]$GTPyS loading) is only seen at the Gi fusion, and not at Gq and Gs fusions. These data verify the functionality of the GPCR-Gα fusions used herein and show their fidelity to reported pharmacology of unfused native GPCRs.
Figure 11C:
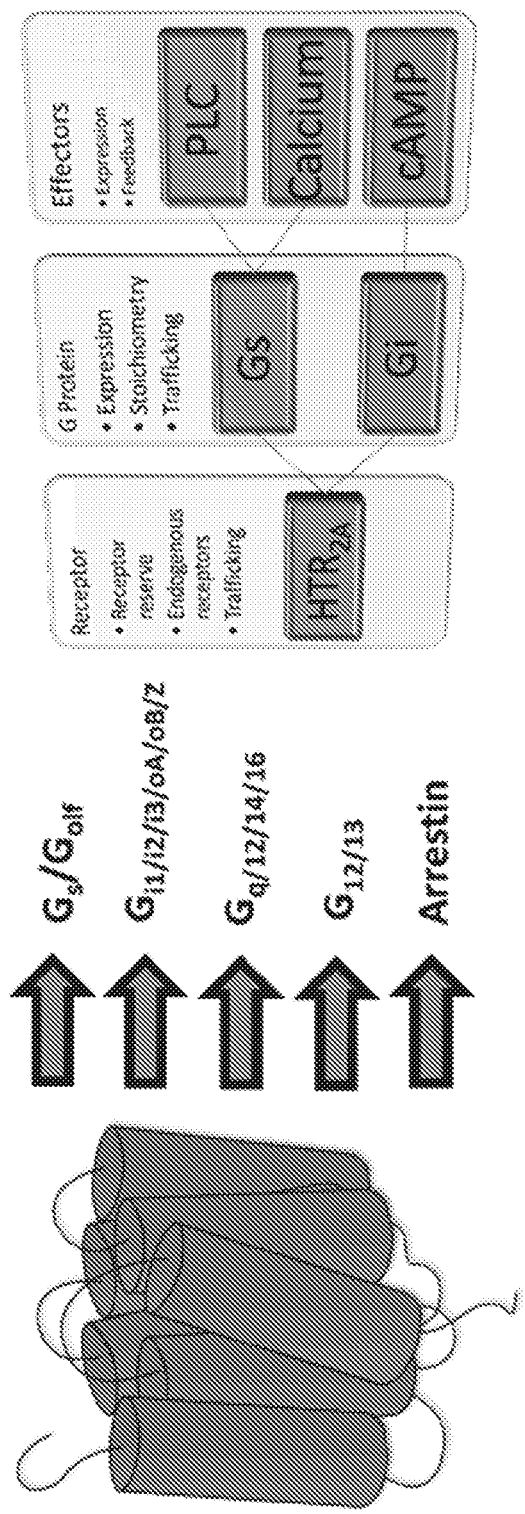
FIG. 11C illustrates that GPCRs signal through multiple potential transducer pathways (e.g. 16 non-visual G proteins and arrestins, not exhaustive). While classically divided into four effector families (e.g. Gi family inhibits adenylyl cyclase production, Gs family stimulates adenylyl cyclase, Gq family stimulates PLC, and G12/13 regulates Rho GEFs), many functional assays of effector activation rely on the expression of intermediary downstream signaling pathway components. The full complement of these signaling components may not be present in every cell type and reconstituting these pathways would require significant a priori knowledge of both the physiology of the cell model as well as the details of the G protein/second-messenger pathway. The disclosed TRUPATH platform covers 14 pathways and is proximal to receptor activation, thus circumventing the limitations of standard assays described above.
Figures 13A, 13B:
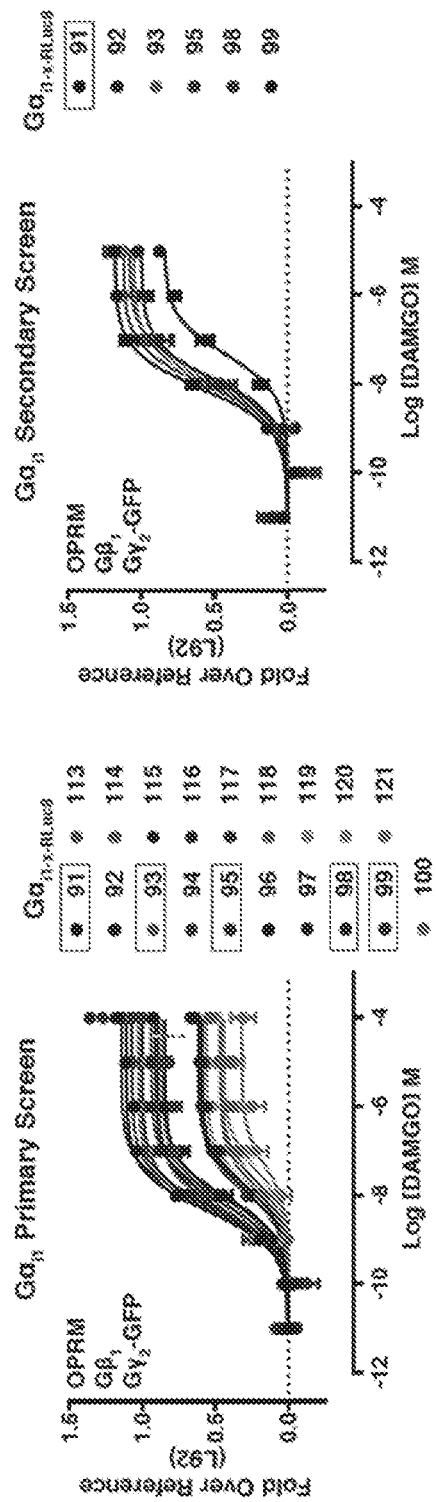
FIGS. 13A to 13D show workflow and data supporting successful optimization of Gαi1 BRET biosensor.
Figures 13C, 13D:
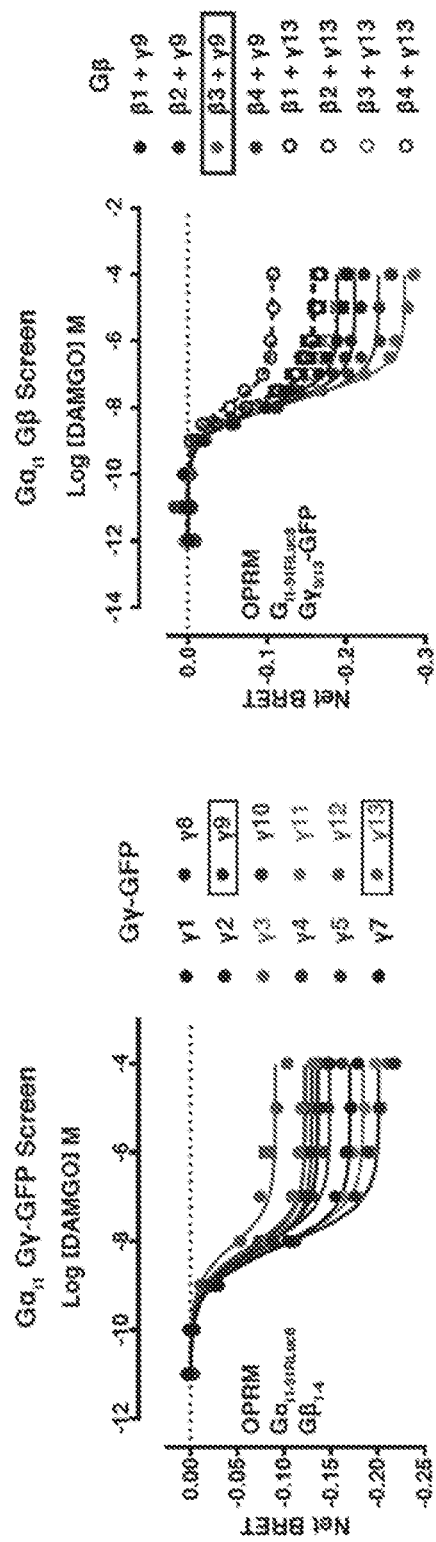
Figures 14A, 14B:
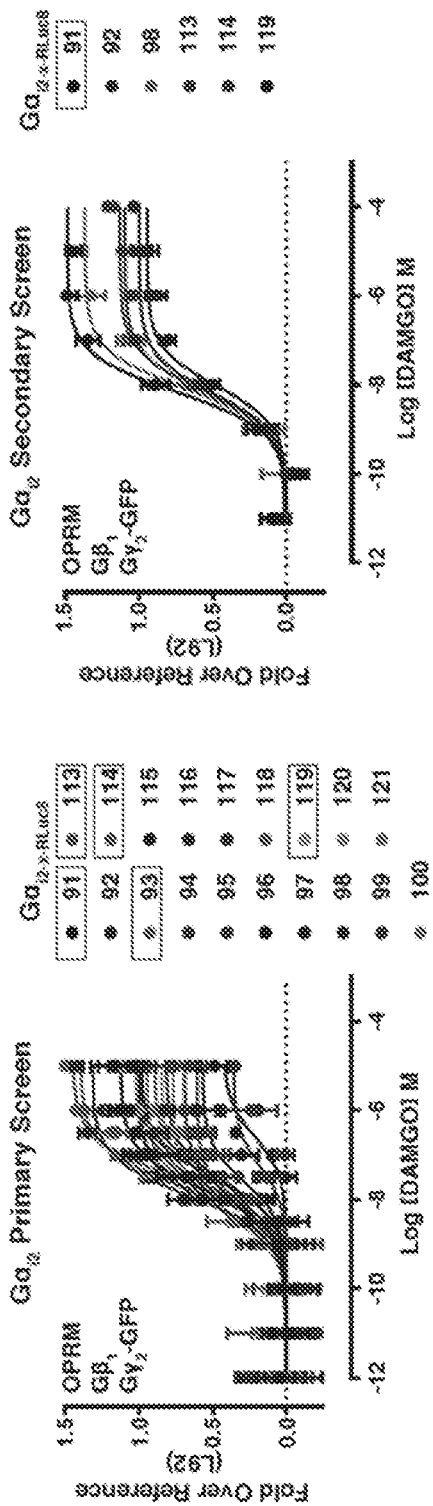
FIGS. 14A to 14D show workflow and data supporting successful optimization of Gαi2 BRET biosensor. Format follows that of FIG. 13. Briefly.
Figures 14C, 14D:
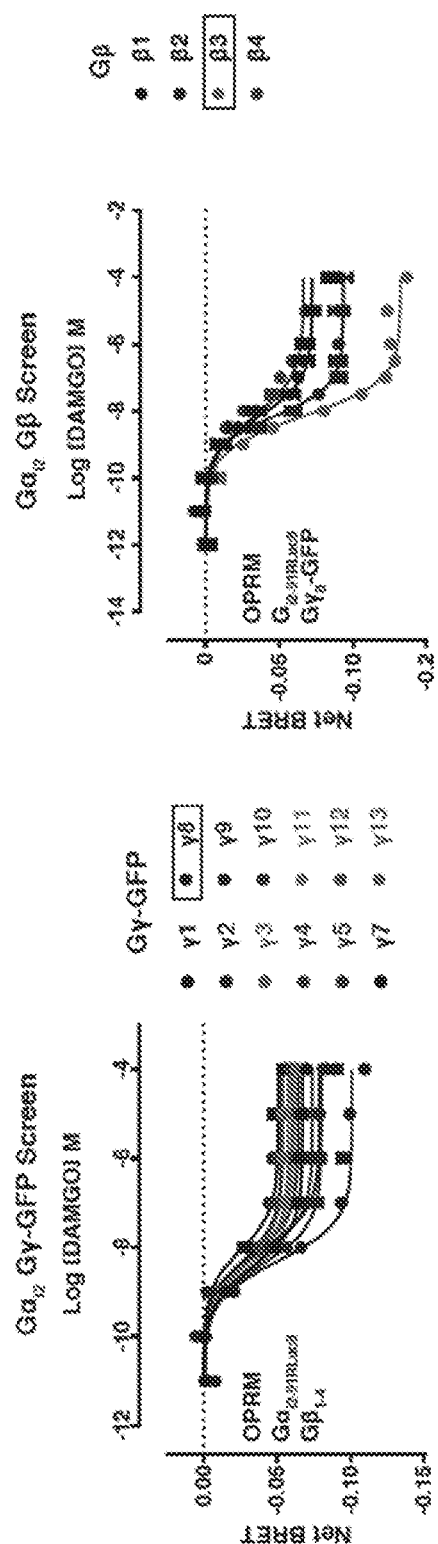
Figure 15B:
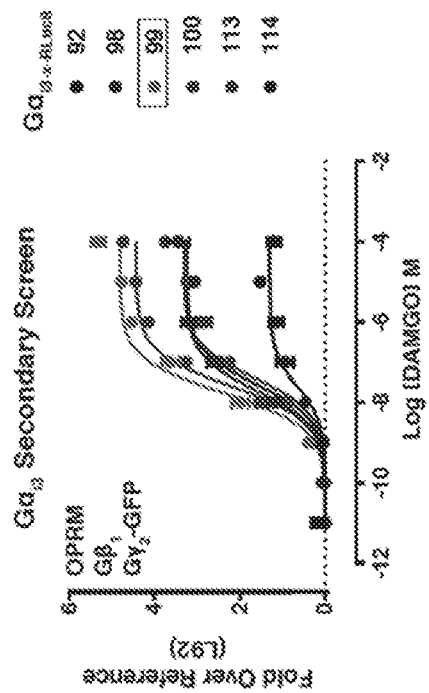
FIGS. 15A to 15D show workflow and data supporting successful optimization of Gαi3 BRET biosensor. Format follows that of FIG. 13. Briefly.
Figure 15A:
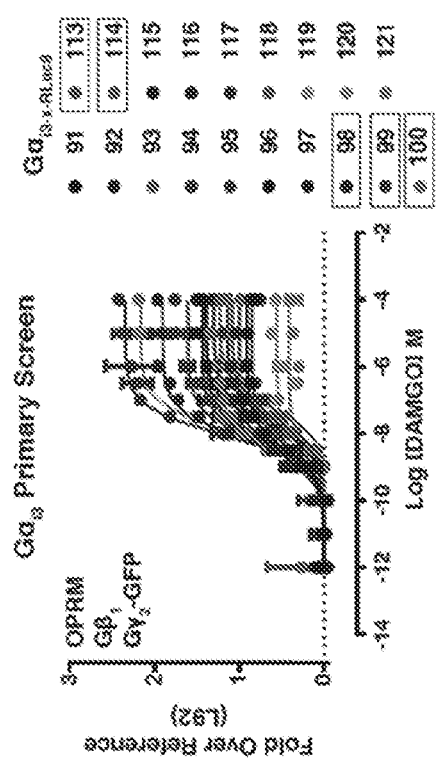
Figures 15C, 15D:
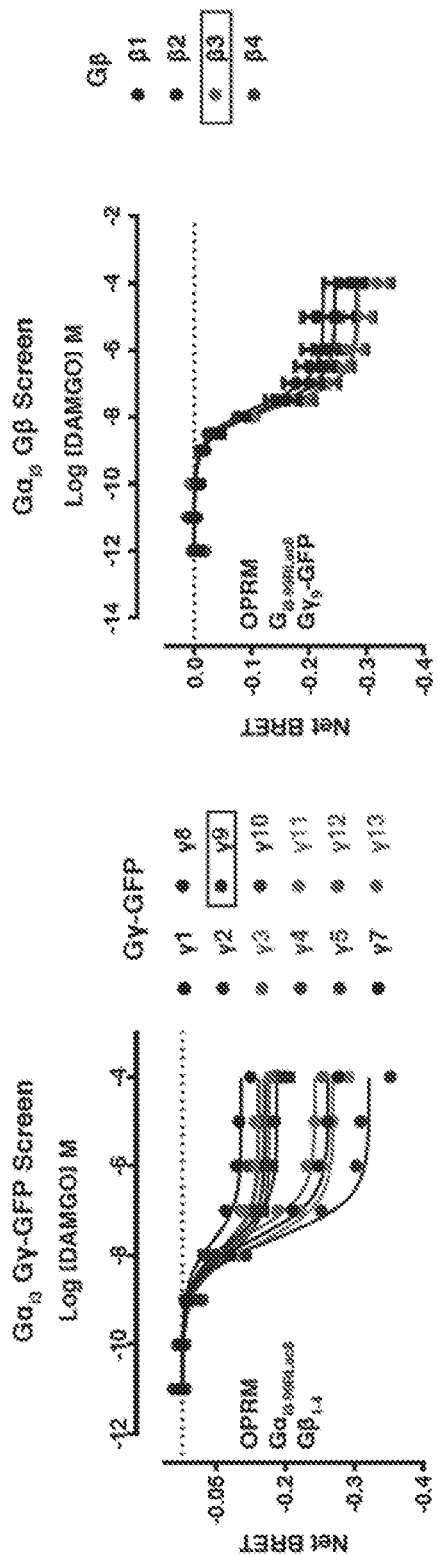
Figures 16A, 16B:
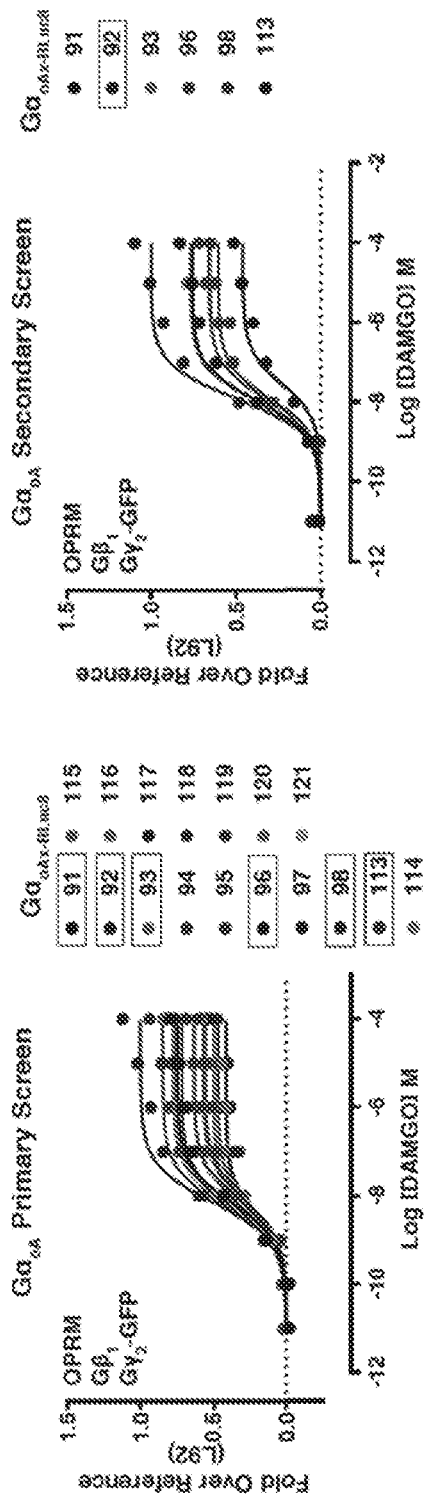
FIGS. 16A to 16D show workflow and data supporting successful optimization of GαoA BRET biosensor. Format follows that of FIG. 13. Briefly.
Figures 16C, 16D:
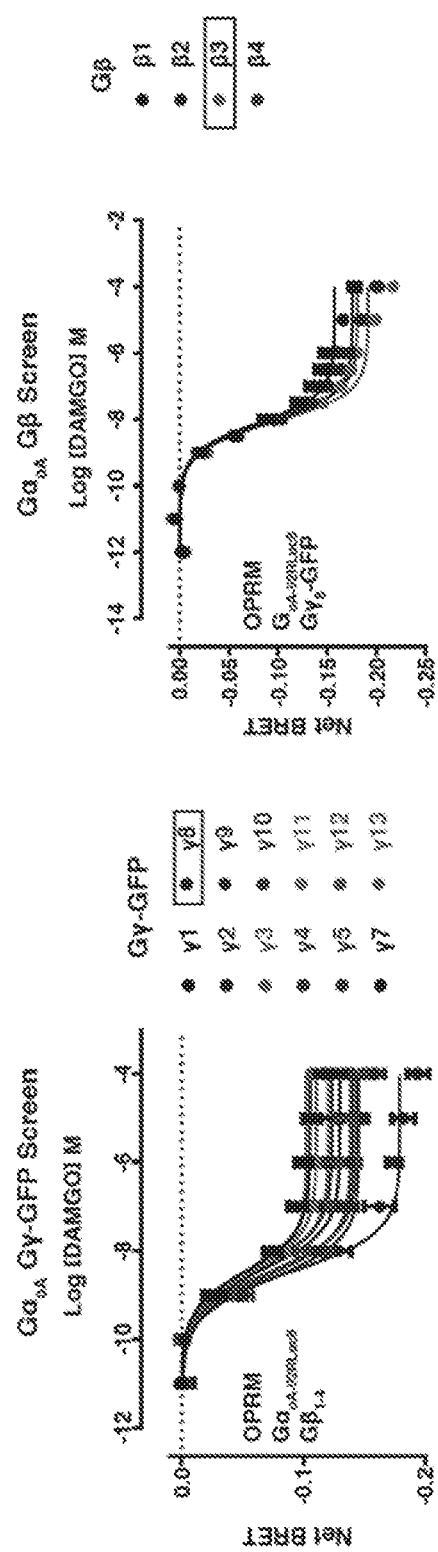
Figure 17B:
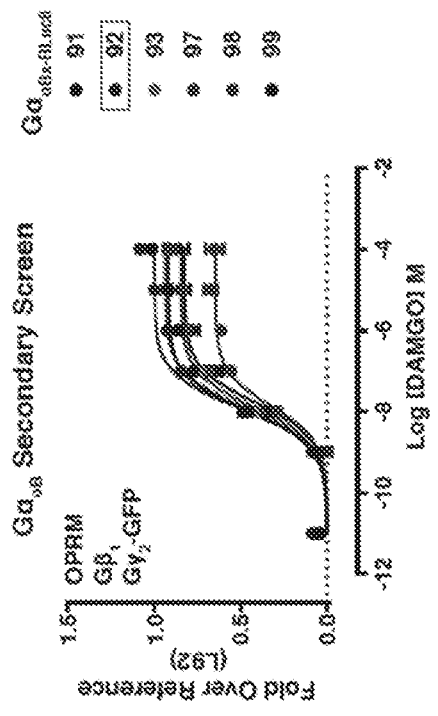
FIGS. 17A to 17D show workflow and data supporting successful optimization of GαoB BRET biosensor. Format follows that of FIG. 13. Briefly.
Figure 17A:
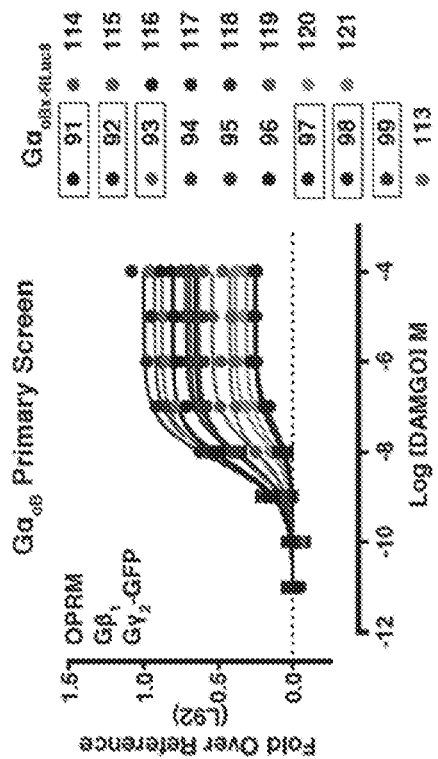
Figure 17D:
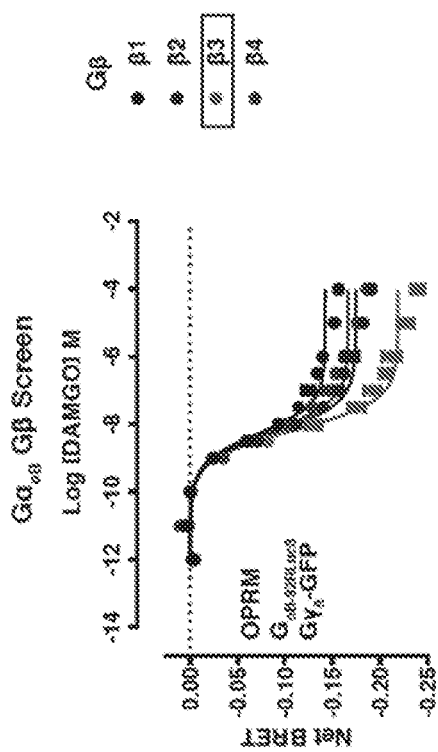
Figure 17C:
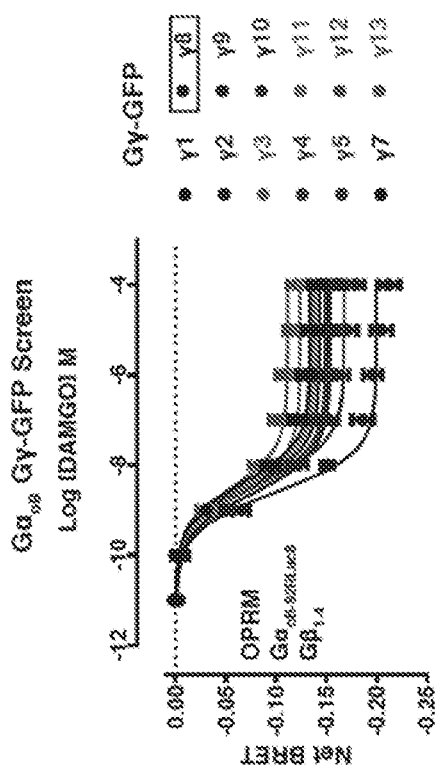
Figures 18A, 18B:
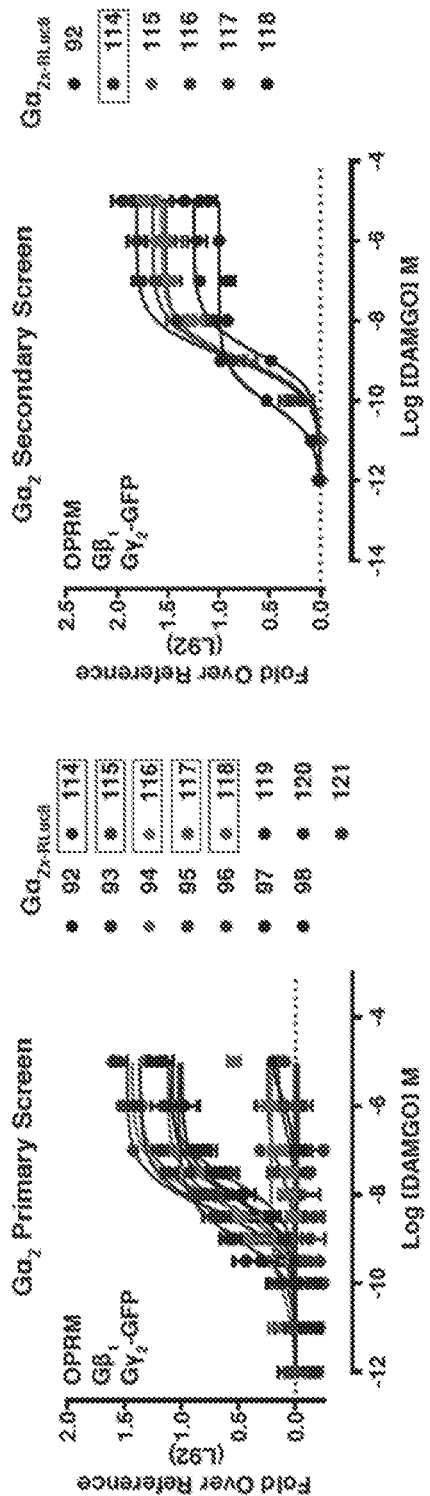
FIGS. 18A to 18D show workflow and data supporting successful optimization of GαZ BRET biosensor. Format follows that of FIG. 13. Briefly.
Figure 18D:
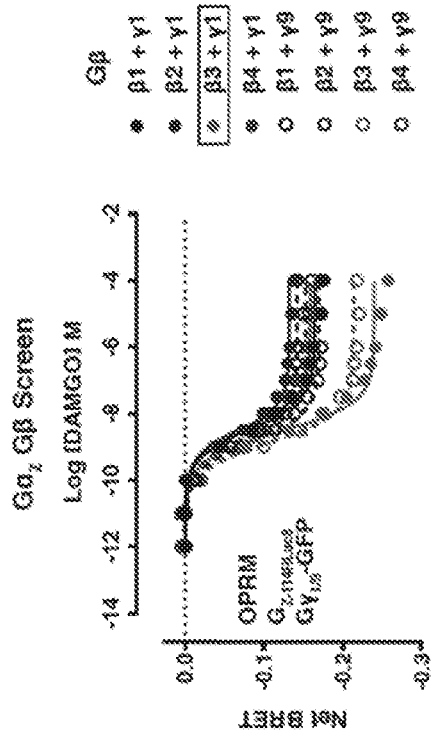
Figure 18C:
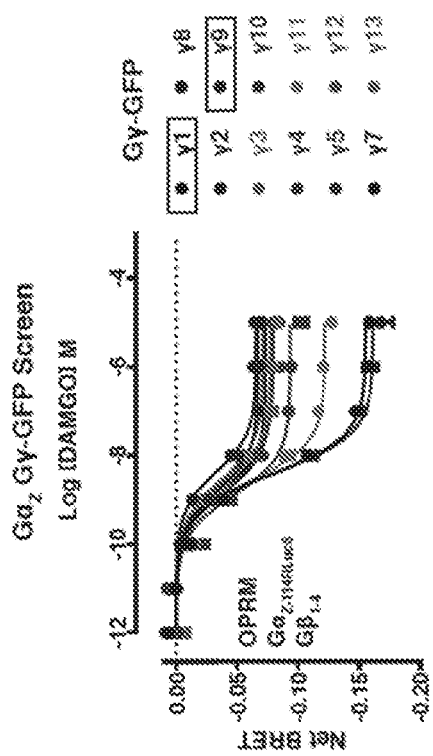
Figure 19A:
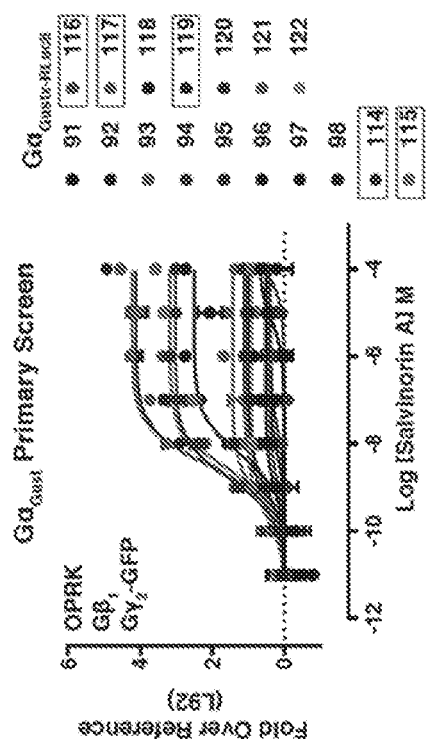
FIGS. 19A to 19D show workflow and data supporting successful optimization of GαGustducin BRET biosensor. Format follows that of FIG. 13. Briefly.
Figure 19B:
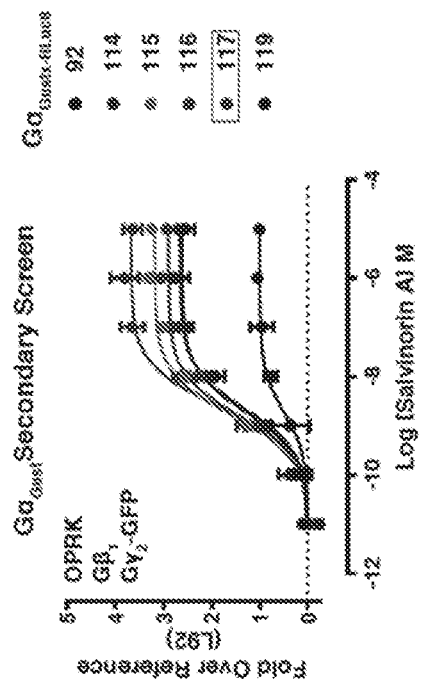
Figures 19C, 19D:
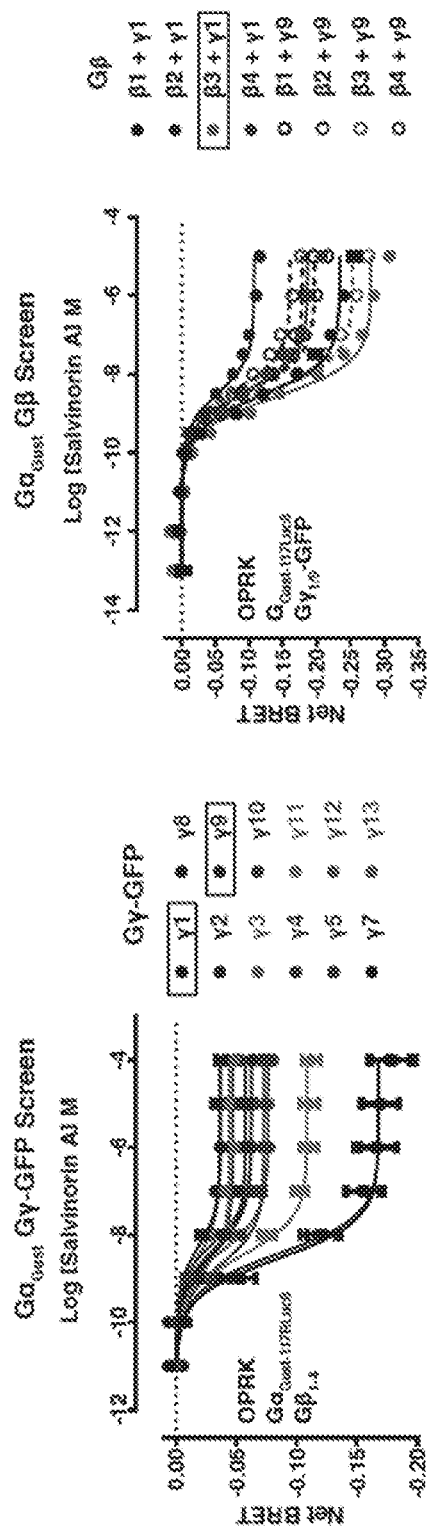
Figures 20A, 20B:
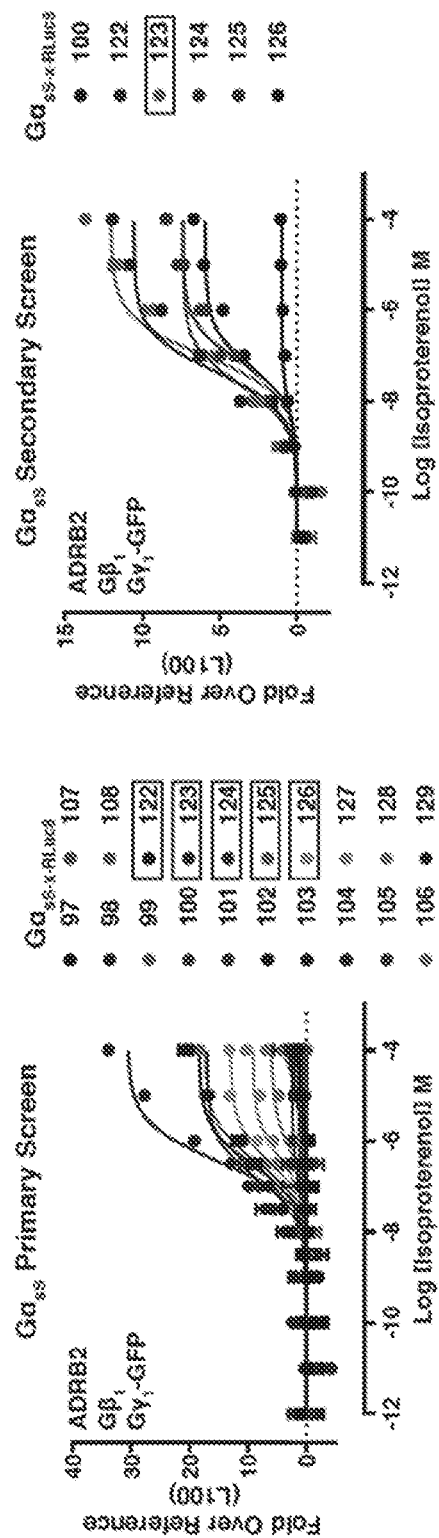
FIGS. 20A to 20D show workflow and data supporting successful optimization of GαsShort BRET biosensor. Format follows that of FIG. 13. Briefly.
Figure 20D:
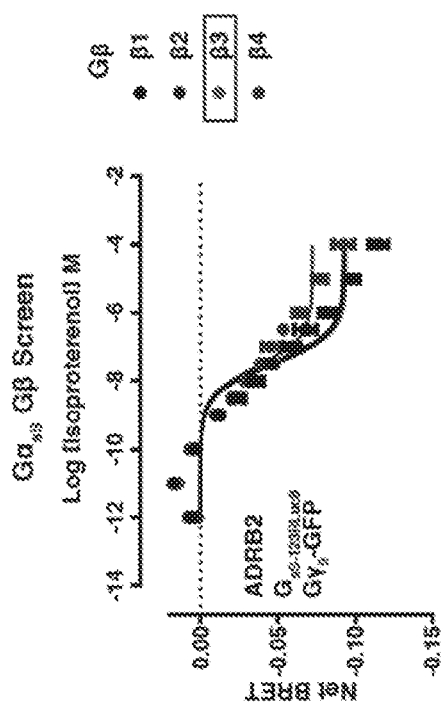
Figure 20C:
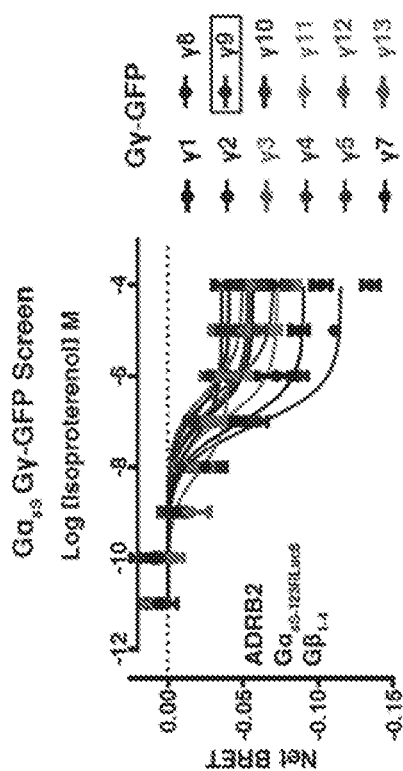

TRUPATH is a comprehensive signal transduction profiling assay that correlates heterotrimeric G protein dissociation with downstream signaling. It can be run in unfused or transducer-receptor-fused scenarios and is based on the concept of Förster Resonance Energy Transfer. The described application herein relies on a bioluminescent donor enzyme, a derivation called Bioluminescence Resonance Energy Transfer (e.g. BRET) (FIG. 3A). The advances described herein can also be applied to the analogous formulation wherein two fluorescent molecules are used rather than a luminescent donor and fluorescent acceptor (e.g. Fluorescence Resonance Energy Transfer, or FRET). BRET is used to measure the interaction (e.g. association or dissociation) or proximity of two entities (e.g. proteins). In brief, one interacting partner is tagged or labeled with a luminescent enzyme (a donor, e.g. Renilla luciferase) which can catalyze the breakdown of a substrate that produces light as a byproduct at a desired wavelength. The other interacting partner is tagged with a fluorescent protein with appropriate absorption and emission wavelengths (an acceptor, e.g. GFP2). If the acceptor is close enough to the site of chemical reaction the luminescence can excite the fluorophore producing fluorescence. This is known as resonance energy transfer. The relative change in the ratio of these two signals is a measure of the changing association or dissociation of the two partners. Extending this principle to known interacting partners of targets (such as heterotrimeric G proteins) measures the activation of these signaling pathways. A specific example of G protein pathway activation (e.g. the dissociation of the GαGβGγ complex) is described below:

A GPCR is an allosteric machine that catalyzes the exchange of one nucleotide (e.g. GDP) for another (GTP) in the subunit of a physically associated Gα protein. The Gα protein when inactive is closely associated with the GβGγ subunit (an obligate dimeric complex). By tagging the Gβ or Gγ subunit with a donor or acceptor, and the Gα with a donor or acceptor, the association or dissociation of this complex can be measured (FIG. 3A). If the receptor and ligand interaction can activate this pathway the complex dissociates when the receptor is active (natively, by mutation, or perturbation by a ligand as defined above) and changes to the rate or magnitude of activation of the receptor can be determined by the changing BRET ratio of these complexes. In the disclosed approach, insertion sites for the donor and acceptor within the Gα subunits have been empirically determined and optimized (FIGS. 7, 13-25, Table1), and the optimal GβGγ subunit complex for each Gα has been empirically identified (FIGS. 7, 13-25, Table 1). If required, fusing the Gα to the receptor (e.g. the target-transducer system from ADSoRB) ensures a 1:1 local stoichiometry in our system, maintains appropriate membrane trafficking, and provides fidelity to the expressed receptor/transducer pathway (FIG. 11A, 11B). This increases the dynamic range of the assay (FIG. 4A, 4B).

Figure 21B:
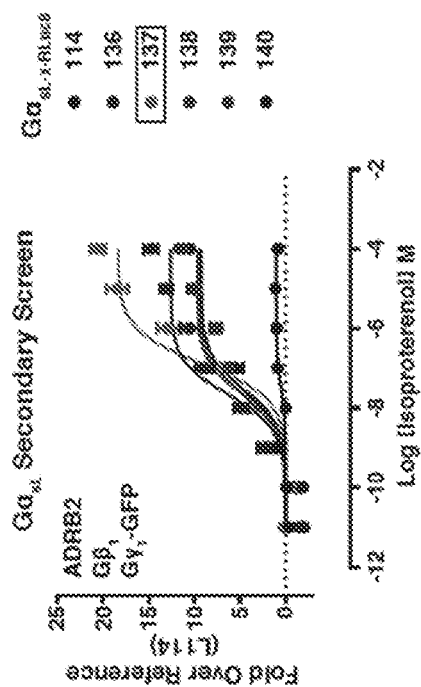
FIGS. 21A to 21D show workflow and data supporting successful optimization of GαsLong BRET biosensor. Format follows that of FIG. 13. Briefly.
Figure 21A:
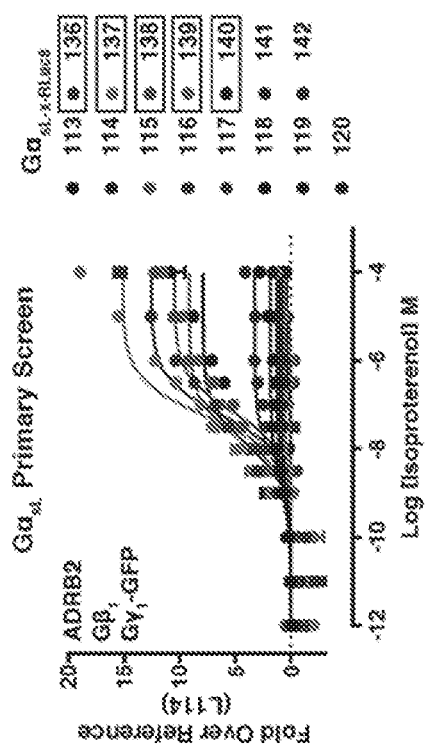
Figure 21D:
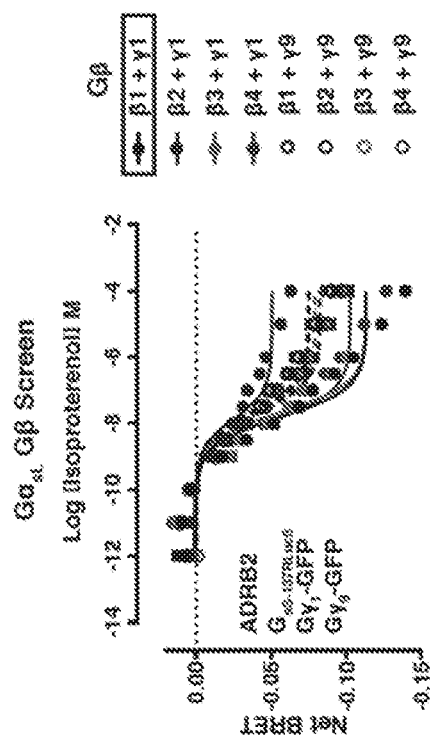
Figure 21C:
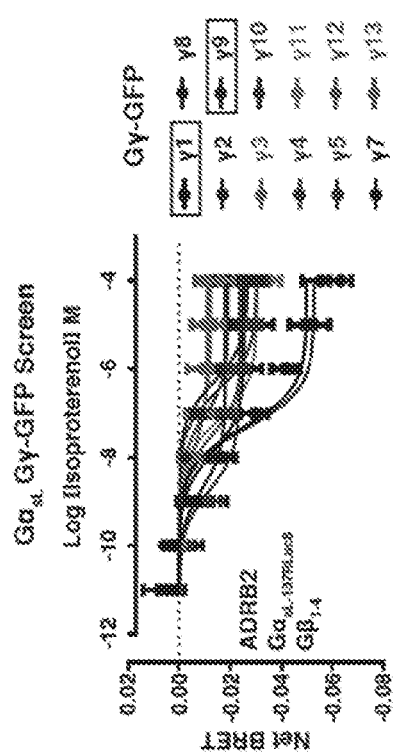

TRUPATH biosensor compositions are novel as insertion sites for the donor/acceptor within the Gα subunits and GβGγ acceptor pairs have been empirically determined and optimized (see below for detailed explanation, FIGS. 3, 7, 13-25). A list of top performing insertion sites is included in Table 1 and their improvements over existing BRET assays are detailed in FIG. 29 and Table 2. Notably, apart from some of the closely related isoforms, we did not observe any consistent pattern in the final Gα-Rluc chimeras. This supports the position that a purely structure-guided or homology-based approach for generating optimal Gα-Rluc chimeras is not likely to be successful and that optimal sensor design is non-obvious. Some insertion sites are relatively equivalent, as are certain GβGγ dimer pairings, which is reflected in the top amino acid (AA) positions and GβGγ compositions listed for each G protein in Table 1. Unlike what is standard practice, TRUPATH biosensors frequently use atypical GβGγ pairings (e.g. GβGγ9 and Gβ3Gγ13) (Table 1). For comparison, current standard Gβ1Gγ1 and Gβ1Gγ2 dimers underperformed at all but one sensor, GsLong, although Gβ1Gγ1 was practically indistinguishable from Gβ4Gγ1 (FIG. 21D, Table 1). For completeness, we disclose and claim for each G protein the top five Gα-Rluc chimeras, top five Gγ-GFP subunits, and all Gβ subunits since they were frequently equivalent (Table 1).

Figure 22B:
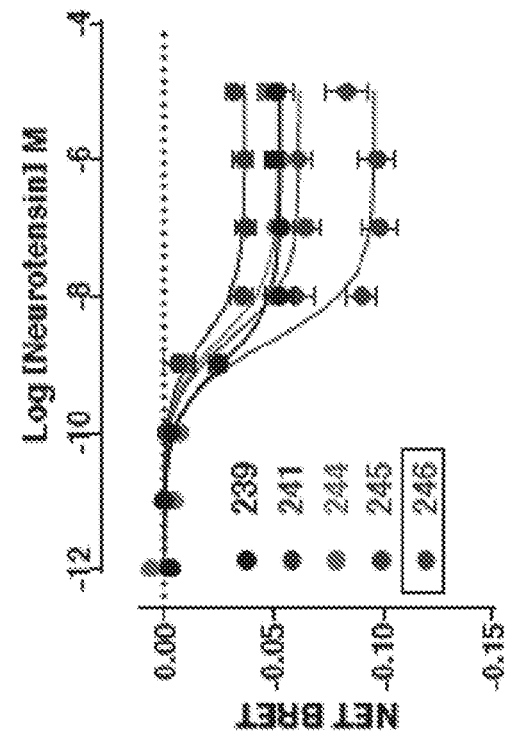
FIGS. 22A to 22D show workflow and data supporting successful optimization of Gα11 BRET biosensor. Format follows that of FIG. 13. Briefly.
Figure 22A:
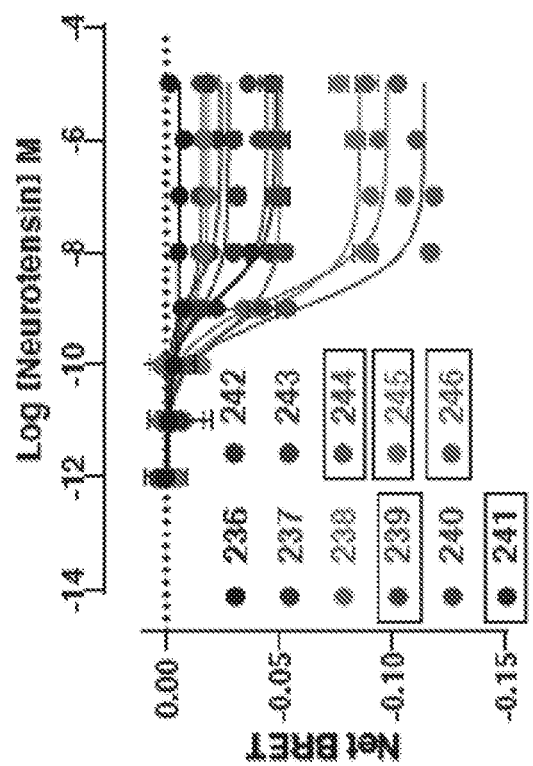
Figures 22C, 22D:
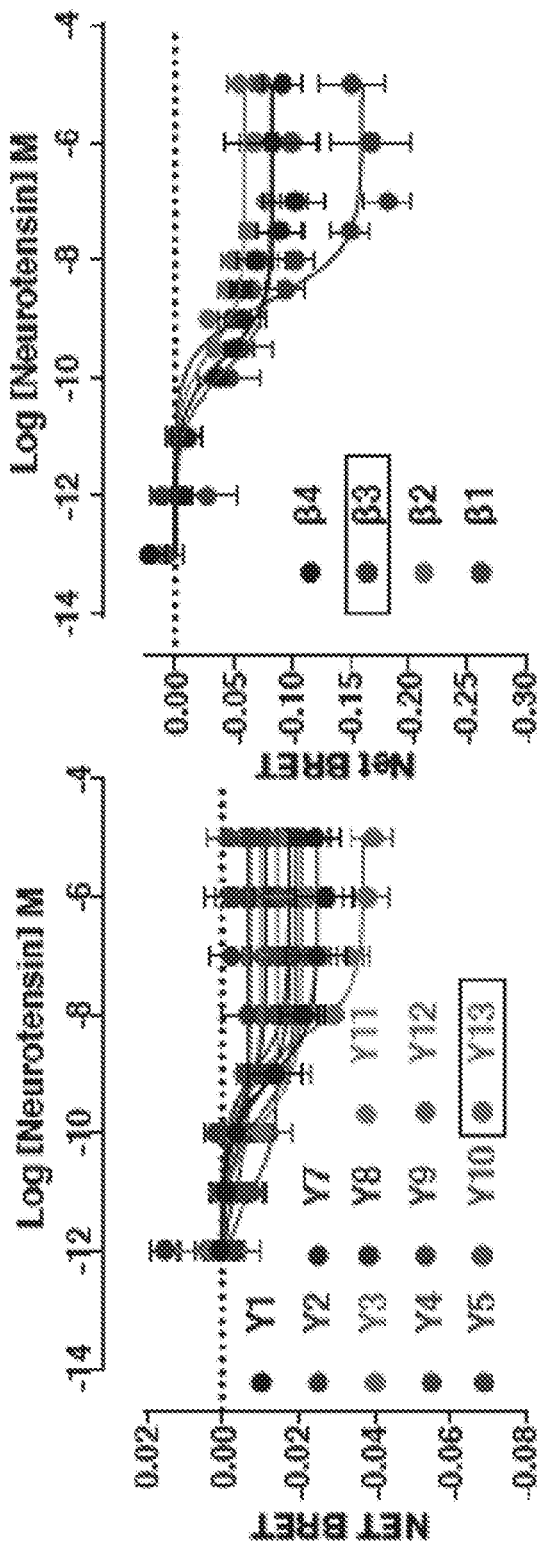
Figures 23A, 23B:
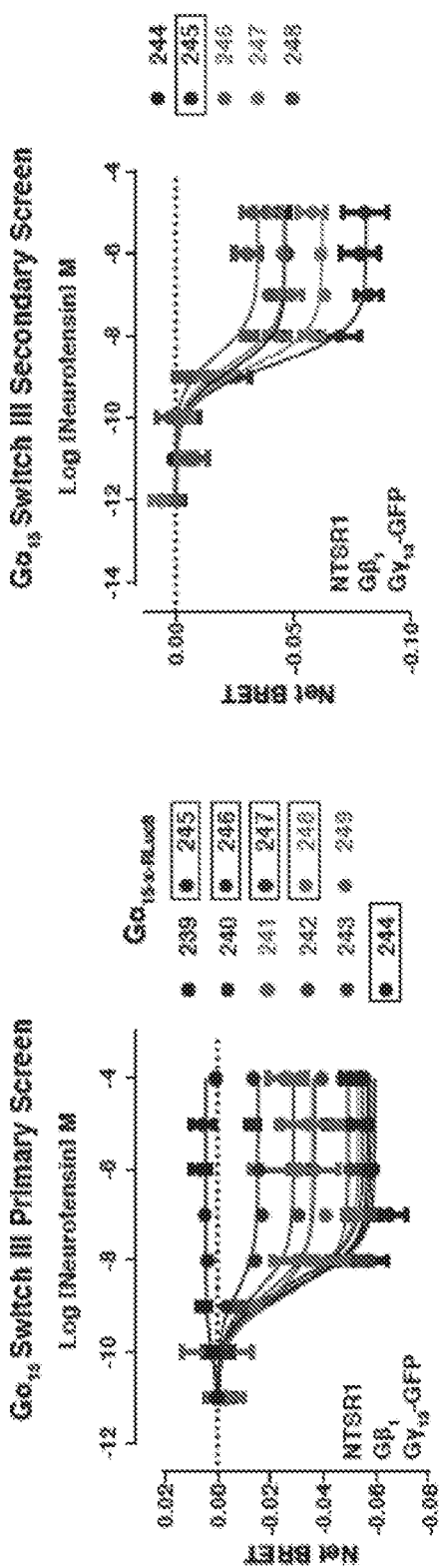
FIGS. 23A to 23D show workflow and data supporting successful optimization of Gα15 BRET biosensor. Format follows that of FIG. 13. Briefly.
Figure 23D:
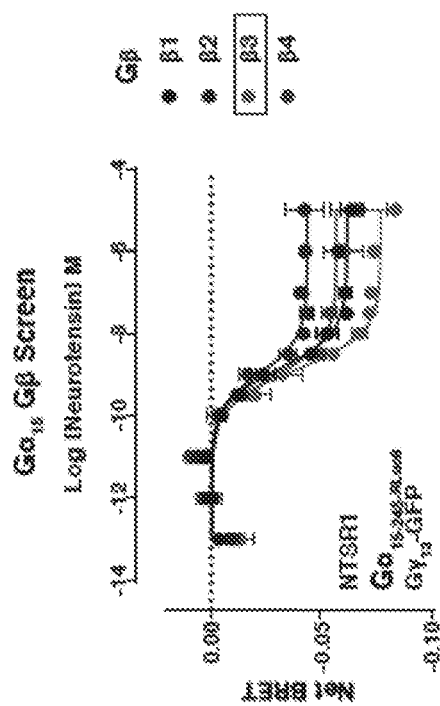
Figure 23C:
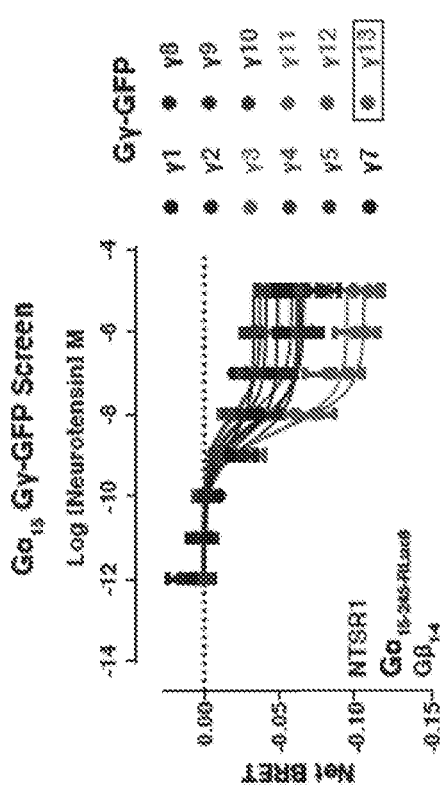
Figures 24A, 24B:
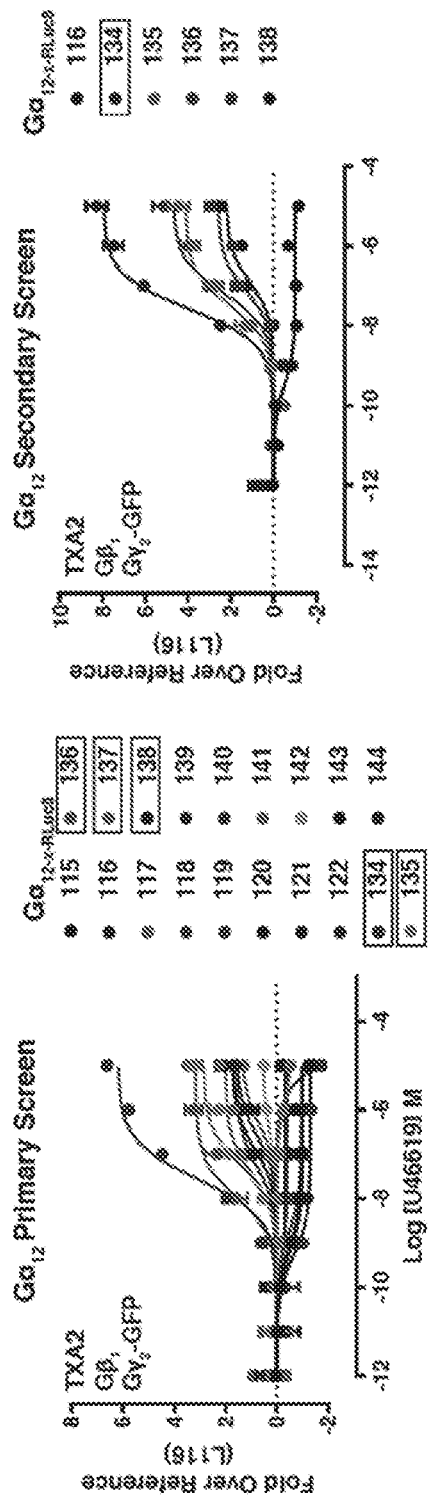
FIGS. 24A to 24D show workflow and data supporting successful optimization of Gα12 BRET biosensor. Format follows that of FIG. 13. Briefly.
Figure 24D:
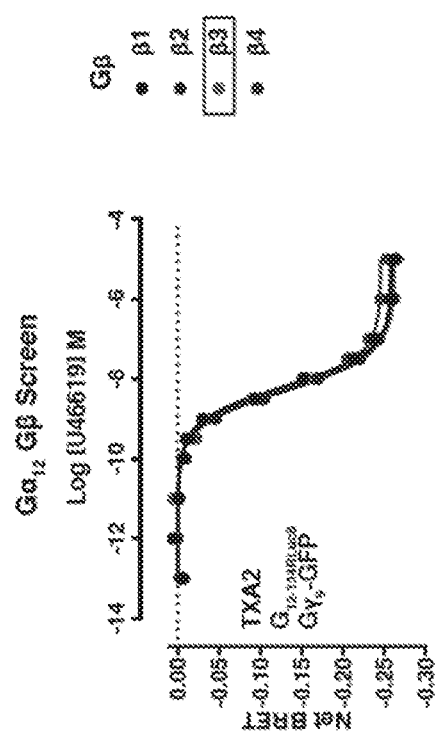
Figure 24C:
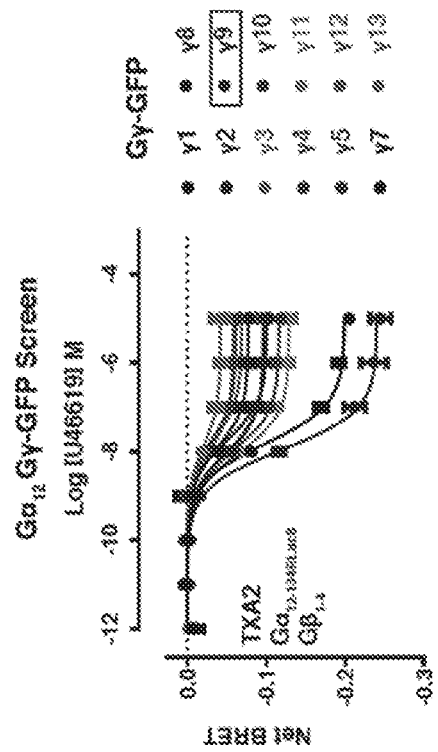
Figure 25D:
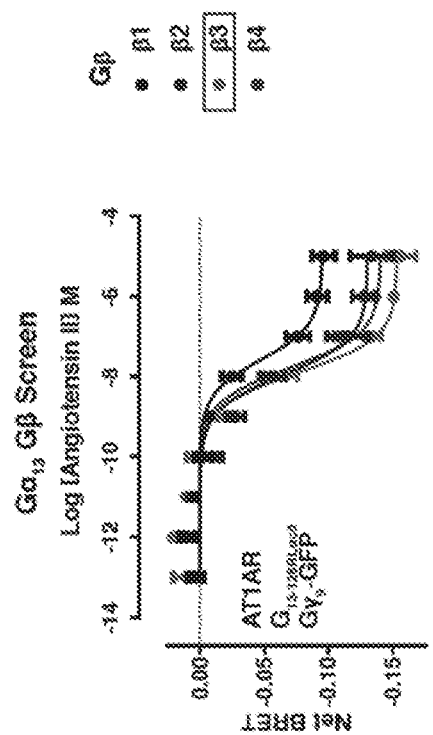
Figure 25C:
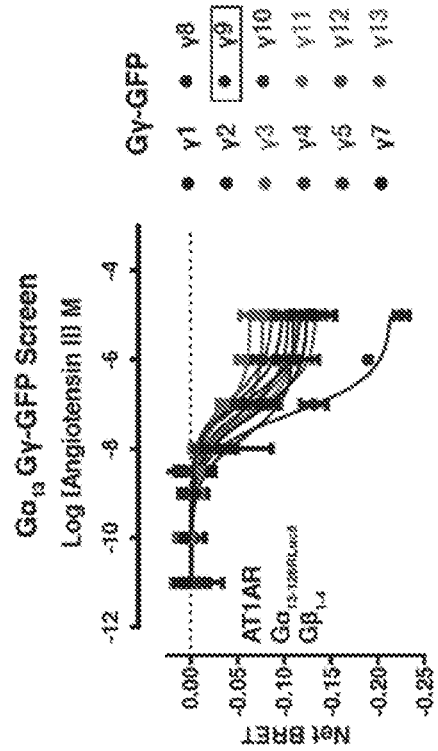
Figure 26A:
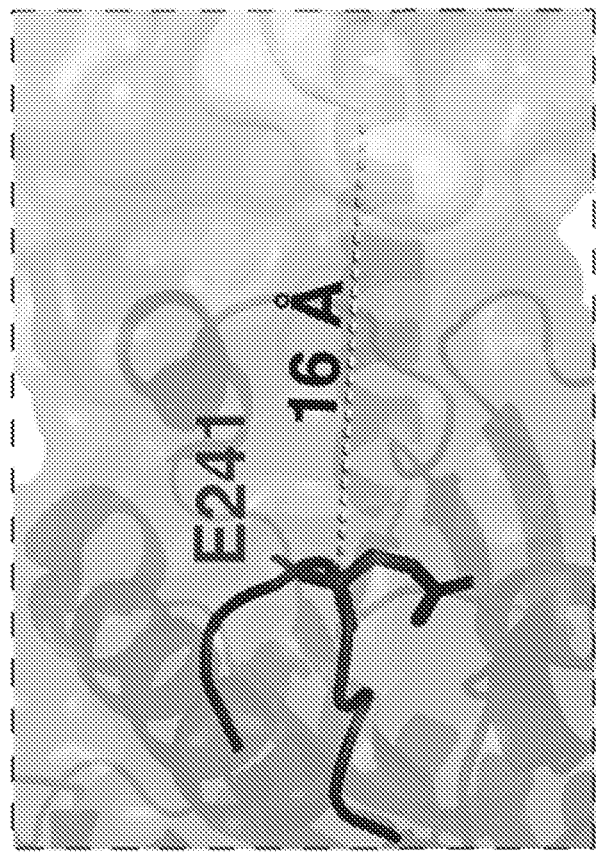
FIGS. 26A to 26C show that Switch III in the Gα-subunit is a novel region for optimal RLuc8 insertion.
Figure 26A:
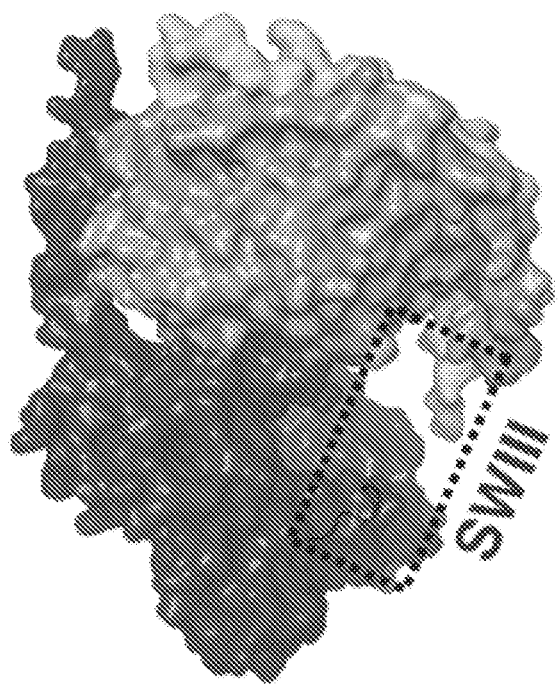
Figure 26B:
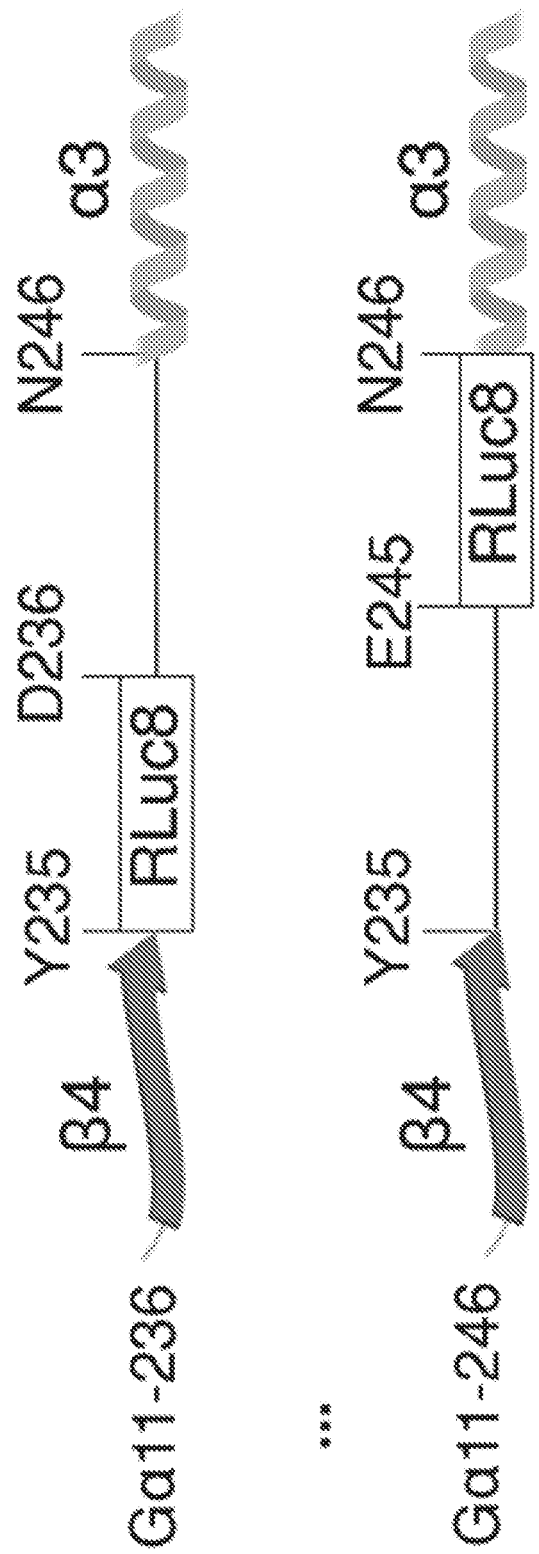
Figure 26C:
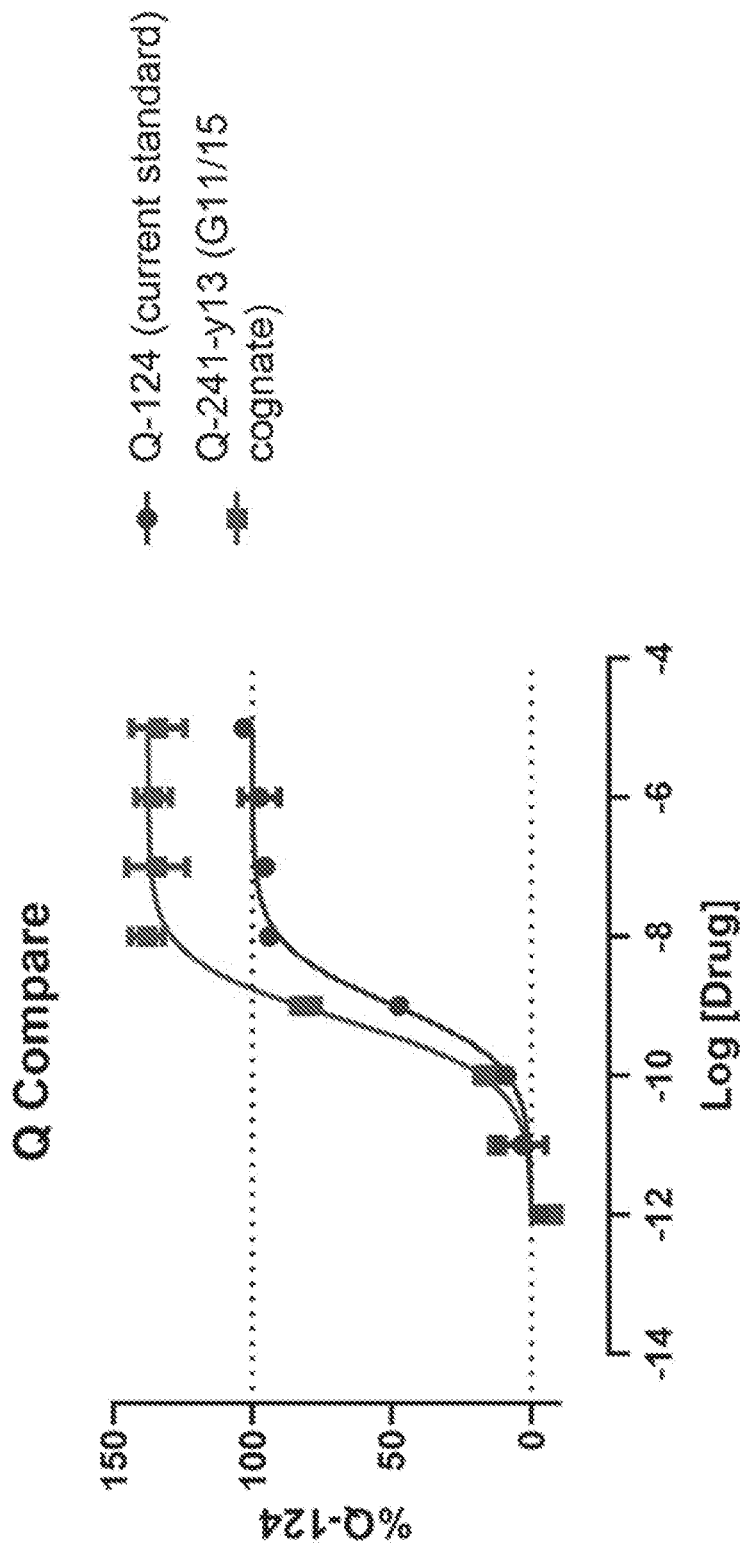
Figure 27:
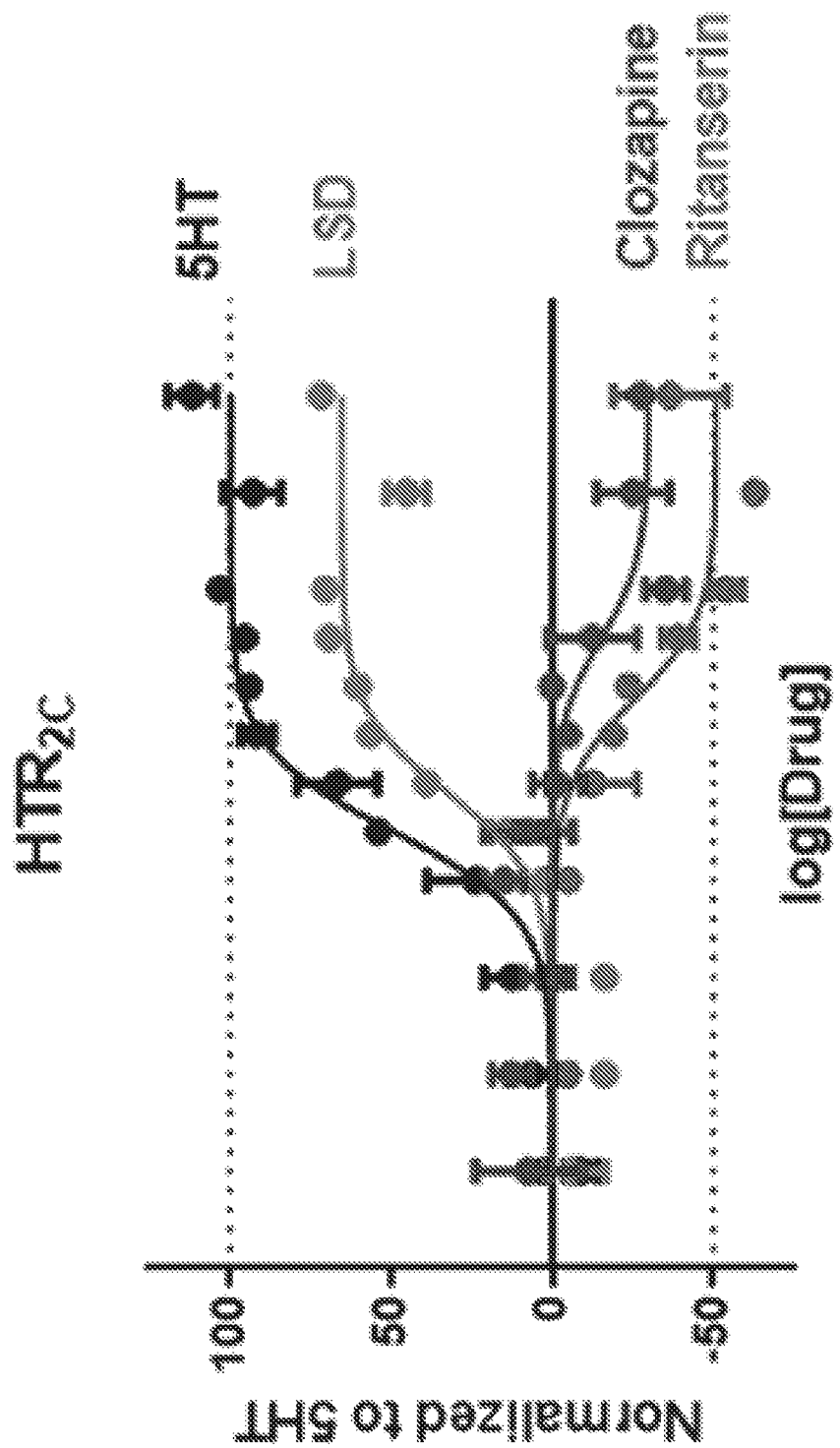
FIG. 27 shows that a BRET system at equilibrium not prone to amplification also allows for the measurement of inverse agonism. Because GPCRs possess varying levels of basal activity, an increase in BRET results from the stabilization of an inactive state. Here, the serotonin 2C receptor (HTR2C), which has a moderate level of basal activity), is inactivated by the inverse agonists ritanserin and clozapine. The HTR2C receptor is one of the most highly variant receptors in the brain, and the consequences of many of these variants are unknown. Some editing variants present a greater risk of suicidality, and as such subtype selective ligands may have substantial therapeutic benefit.

A completely unexplored and non-obvious region for luminescent or fluorescent insertions is disclosed herein. Specifically, we identified a flexible linker region extending from the β4-strand to the α3 helix of the Ras-like domain (Switch III, FIG. 26A). No known chimeric proteins have been generated in this region, likely because mutations within or deletion of the entire Switch III region are thought to negate functional coupling of Gα to its effector. Contrary to this prediction, insertion of RLuc8 into this region (Gα11 (241)-RLuc8, FIG. 26B) yielded a construct that performed identically to its wildtype counterpart. Generation and screening of Gα-RLuc8 constructs spanning this Switch III region (FIG. 26B) used Gγ13 as a suitable, but atypical acceptor pair. The retained function of new Switch III chimeras may be because the insertion of proteins (i.e. chimera generation) may not present the same negative effect on transducer behavior as mutations or deletions-something heretofore unreported or predicted. This region may also be useful for generating chimeras with split GFP or split-luciferase components, or for use with bait-prey type protein complexes to identify novel interacting partners in pulldown and mass-spectrometry assays. The optimization workflow (FIG. 3F-3I) identified optimal Gα11 and Gα15 biosensor compositions using Switch III protein engineering (FIGS. 22 and 23). As shown in FIG. 26C, the Switch III version of Gq performed better than the helical domain Rluc8 insertion, thus luciferase insertions within this new region should extend to all sensors in Table 1.

TABLE 1

Example Donor/Acceptor Insertion sites#

| Gα | Top five AA positions* | Gβ | Gγ |
|---|---|---|---|
| i1 | 91*, 93, 95, 98, 99 | 1, 2, 3*, 4 | 1, 9*, , 11, 13 |
| i2 | 91*, 93, 113, 114, 119 | 1, 2, 3*, 4 | 2, 8*, 9, 10 |
| i3 | 98, 99*, 100, 113, 114 | 1, 2, 3*, 4* | 1, , 9*, 11, 13 |
| oA | 91, 92*, 93, 98, 113 | 1, 2, 3*, 4 | 2, 4, 8*, 10 |
| oB | 91, 92*, 93, 97, 99 | 1, 2, 3*, 4 | 2, 8*, 9, 10 |
| Z | 114*, 115, 116, 117, 118 | 1, 2, 3*, 4 | 1*, 4, 9, 11 |
| Q | 119, 122, 123, 125*, 126 | 1, 2, 3*, 4 | 1, 8, 9*, 11 |
| Slong | 136, 137*, 138, 139. 140 | 1*, 2, 3, 4 | 1*, 4, 9, 11 |
| Sshort | 122, 123*, 124, 125, 126 | 1, 2, 3*, 4 | 1, 4, 9*, 11 |
| Gustducin | 114, 115, 116, 117*, 119 | 1, 2, 3*, 4 | 1*, 9, 11, 12 |
| G12 | 134*, 135, 136, 137, 138 | 1, 2, 3*, 4 | 1, 4, 9*, 11 |
| G13 | 125, 126*, 127, 128, 129 | 1, 2, 3*, 4 | 1, 7, 9*, 12 |
| G11 | 239, 241, 244, 245, 246* | 1, 2, 3*, 4 | 1, 3, 11, 13* |
| G14 | ND | ND | ND |
| G15 | 244, 245*, 246, 247, 248 | 1, 2, 3*, 4 | 2, 3, 9, 13* |
| Golf | ND | ND | ND |

*Denotes top Gα-Rluc chimera, Gβ, or Gγ-GFP. To efficiently define the optimal Gα-RLuc8/Gβγ-GFP heterotrimer composition, we established a screening process and a-priori selection criterion for each step of the optimization (i.e., the construct with the greatest dynamic range, defined as Emax-Basal signal in a dose response assay, was chosen for further refinement).
For naming, we use the position of the first amino acid in the linker-RLuc8 in the full protein sequence. For example, insertion of RLuc8 following the lysine at position 97 in Gαq is named Gαq(98)RLuc8, Head-to-head comparisons against other BRET heterotrimer sensors demonstrates that TRUPATH biosensor compositions are superior at every G protein tested, with statistically significant improvements ranging from 1.5- to approximately 100-fold (FIG. 29 and Table 2), with the median and mean improvements being 7.8- and 20.5-fold, respectively.

Figure 30A:
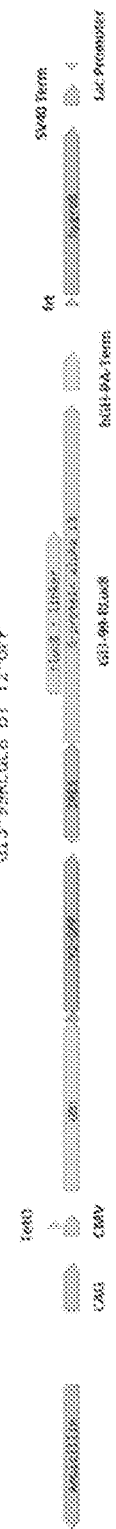
FIGS. 30A to 30C show triple plasmid architecture incorporating all three heterotrimer components (Gα-Rluc8/Gβ/Gγ-GFP2). Shown in FIG. 30A is the Gαi3-99-Rluc8/Gβ1γ2-GFP2 biosensor and in FIG. 30B is the Gαi3-99-Rluc8/Gβ3γ9-GFP2 biosensor.
Figure 30B:
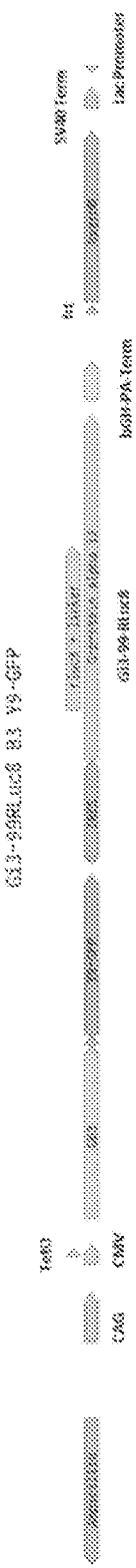
Figure 30C:
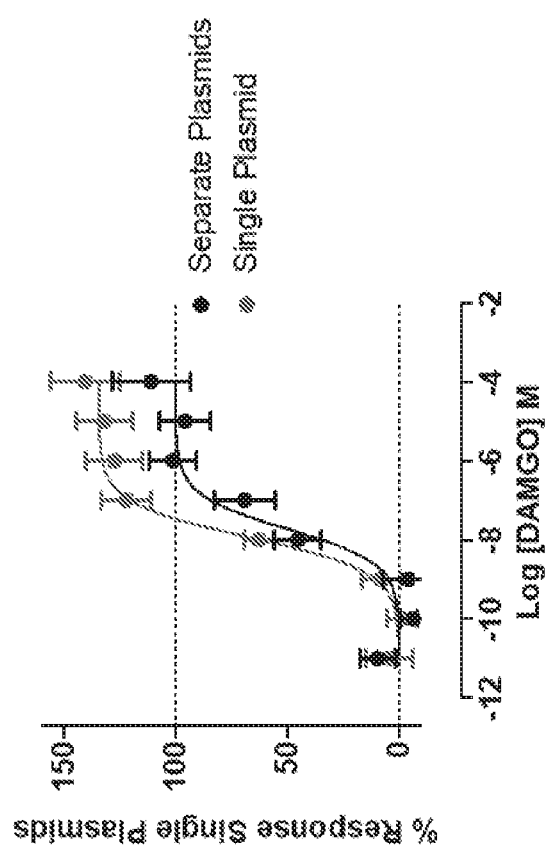
Figure 31:
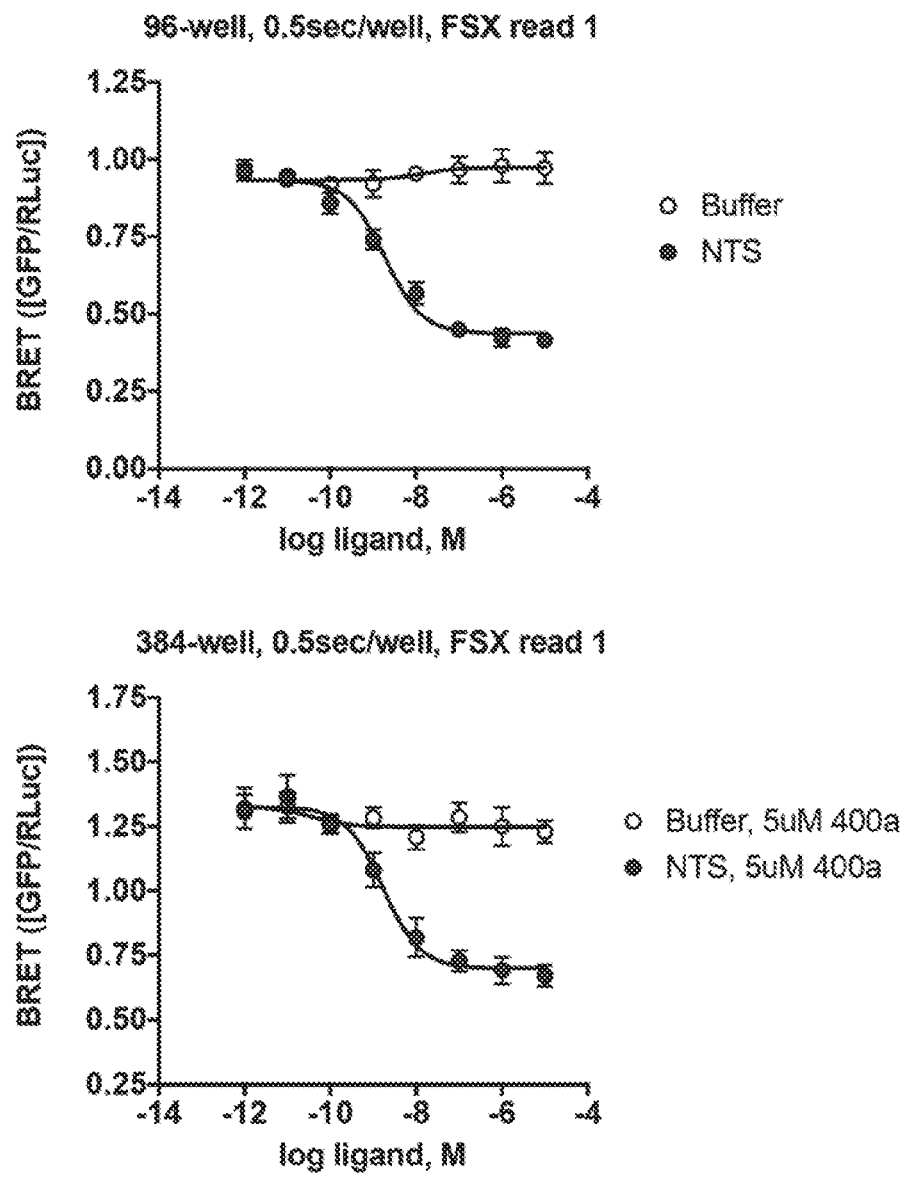

The TRUPATH platform can be enhanced by generating polycistronic 'triple plasmids' that encode Gα, Gβ, and Gγ subunits under the same promoter using 2A self-cleaving peptide and internal ribosome entry site sequences (FIG. 30A,B). Here it is shown to work with the TRUPATH Gαi3 biosensor (FIG. 30C). Compared to a quadruple co-transfection protocol, the triple plasmid strategy increases the NET BRET signal (FIG. 30C) and will improve the between-experiment consistency. Preliminary results (FIG. 30C) show that there is no difference in the measured ligand pharmacology between approaches.

The general principle described in the G protein example can be extended to situations such as the recruitment of other transducers such as arrestins, scaffolding complexes, or in some cases the dissociation of other complexes at the receptor.

TABLE 2

Head-to-head comparison for TRUPATH sensors#

| | | Reference | | | | Optimized Sensor | | | | | |
|---|---|---|---|---|---|---|---|---|---|---|---|
| Gα | Receptor | AA position | Gγ-GFP | Gβ | Net BRET (Avg ± SEM) | AA position | Gγ-GFP | Gβ | Net BRET (Avg ± SEM) | Fold Increase | T | p |
| I1 | OPRM | 92 | γ2 | β1 | 0.018 ± 0 003 | 91 | γ9 | β3 | 0.229 ± 0.004 | 2.12 ± 0.03 | 24.6 | <0.0001 |
| I2 | OPRM | 92 | γ2 | β1 | 0.013 ± 0.002 | 91 | γ8 | β3 | 0.103 ± 0.003 | 7.81 ± 0.23 | 25.43 | <0.0001 |
| I3 | OPRM | 92 | γ2 | β1 | 0.063 ± 0.003 | 99 | γ9 | β3 | 0.245 ± 0.006 | 3.9 ± 0.07 | 36.27 | <0.0001 |
| oA | OPRM | 92 | γ2 | β1 | 0.127 ± 0.003 | 92 | γ8 | β3 | 0.185 ± 0.005 | 1.48 ± 0.04 | 9.472 | |
| oB | OPRM | 92 | γ2 | β1 | 0.130 ± 0.003 | 92 | γ8 | β3 | 0.198 ± 0.003 | 1.52 ± 0.03 | 11.95 | |
| Z | OPRM | 92 | γ2 | β1 | 0.037 ± 0.003 | 114 | γ1 | β3 | 0.251 ± 0.006 | 6.87 ± 0.16 | 32.95 | <0.0001 |
| Gust | KOR | 92 | γ2 | β1 | 0.003 ± 0.001 | 117 | γ1 | β3 | 0.223 ± 0.006 | 65.43 ± 1.75 | 35.84 | <0.0001 |
| sS | ADRB2 | 100 | γ1 | β1 | 0.016 ± 0.002 | 123 | γ9 | β3 | 0.128 ± 0.006 | 7.81 ± 0.35 | 18.75 | <0.0001 |
| sL | ADRB2 | 114 | γ1 | β1 | 0.018 ± 0.003 | 137 | γ1 | β3 | 0.077 ± 0.005 | 5.43 ± 0.25 | 17.24 | <0.0001 |
| Olf | ADRB2 | 101 | γ2 | β1 | n.d. | n.d | n.d. | n.d. | n.d. | n.d. | n.d. | n.d. |
| Q | NTSR1 | 98 | γ1 | β1 | 0.018 ± 0.002 | 125 | γ9 | β3 | 0.203 ± 0.005 | 11.04 ± 0.18 | 49.59 | <0.0001 |
| 11 | NTSR1 | 98 | γ1 | β1 | 0.001 ± 0.001 | 246 | γ13 | β3 | 0.123 ± 0.008 | 106.58 ± 6.49 | 16.25 | <0.0001 |
| 14 | NTSR1 | 98 | γ2 | β1 | n.d. | n.d. | n.d. | n.d. | n.d. | n.d. | n.d. | n.d. |
| 15 | NTSR1 | 101 | γ2 | β1 | 0.006 ± 0.001 | 245 | γ13 | β3 | 0.047 ± 0.003 | 8.01 ± 0.46 | 14.36 | <0.0001 |
| 12 | NTSR1 | 115 | γ2 | β1 | 0.004 ± 0.001 | 134 | γ9 | β3 | 0.161 ± 0.002 | 40.49 ± 0.59 | 65.05 | <0.0001 |
| 13 | NTSR1 | 107 | γ2 | β1 | 0.021 ± 0.002 | 126 | γ9 | β3 | 0.412 ± 0.006 | 19.51 ± 0.29 | 61.39 | <0.0001 |

Raw data (NET BRET and fold-increase in amplitude, FIG. 29) showing significant improvement in dynamic range for all optimized BRET sensors. Data represent mean values ± standard error from three biological replicates. Fold increase in dynamic range (NET BRET) between reference construct sets and the final optimized sensor (TRUPATH) were analyzed by two-tailed unpaired t-tests for each Gα, significance set at 0.05.

Highlighting the platform's strength as a complete drug discovery tool, TRUPATH can be used to i) assay dose-responses of known ligands or those derived from ADSoRB in an effort to determine their efficacies, potencies, or allosteric properties, or ii) assay single point concentrations of ligand across multitudes of conditions (matrix) or large ligand libraries. Conversely, TRUPATH can precede ADSoRB to identify transducer preferences that can then be used to screen and isolate new pathway-specific ligands (i.e. tailor ligand pharmacology). For example, the GPCR-GαRLuc8 fusion protein corresponding to the signaling pathway activated in TRUPATH will serve as the target complex for uHTS of extremely large ligand libraries in ADSoRB. Miniaturizing this platform to 384-well (FIG. 3I) or smaller will accommodate larger scale screening as well as simultaneous reading of BRET to enable kinetic data acquisition.

ADSoRB and TRUPATH are complementary technologies, which as a platform enable large scale profiling of all signaling pathways that can facilitate rapid and targeted screening of complex ligand mixtures, and vice versa. Together, these technologies greatly expand the signaling space and chemical space available to GPCRs, thus increasing our understanding of GPCR function in human health and disease and our ability to treat its dysfunction.

TRUPATH screening has many uses. These include but are not limited to: 1) comprehensive profiling of signaling for any given ligand-GPCR pair, 2) profiling the signaling of receptor mutants and variants (pharmacogenomics), and 3) profiling the signaling of understudied GPCRs and orphan GPCRs (i.e. receptors that lack an endogenous agonist or well-defined physiological function).

A number of embodiments of the invention have been described. Nevertheless, it will be understood that various modifications may be made without departing from the spirit and scope of the invention. Accordingly, other embodiments are within the scope of the following claims.

EXAMPLES

Example 1: Affinity-Directed Selection of Receptor Binders (ADSoRB) Enables Specific Isolation of Opioid Receptor Agonists Methods Cloning: GPCR-transducer fusions in which the top Gα-RLuc8 chimera from TRUPATH (Table 1) is fused via its N-terminus to the C-terminus of a GPCR can be generated via standard cloning methodologies such as Gibson assembly. Fusions between proteins can be direct or use any of the linkers detailed above. See the Genbank formatted example of a receptor-Galpha-Rluc fusion protein (Neurotensin-Gq) provided below.

Microsomal membrane preparation: A given GPCR-transducer fusion in a mammalian expression vector is transiently transfected into HEK293 suspension cells (30 μg DNA/30 mL culture) for overexpression. Microsomes are prepared 36-48 hr post-transfection using differential centrifugation. Briefly, cells are collected at 300×g for 10 min at RT. Cell pellets are resuspended in 10 mL Homogenization Buffer (50 mM TrisHCl, 2 mM EDTA, 1× protease inhibitors, pH7.4) and dounce homogenized on ice (50 strokes, Type A). Lysed cells are centrifuged 500×g for 10 min at 4'C. The low speed supernatant is transferred to a 30 mL centrifuge tube and microsomes are collected at 35,000×g for 60 min at 4° C. The high-speed pellet (P2) is resuspended in 1 mL of Resuspension Buffer (50 mM TrisHCl, 2 mM EDTA, 10 mM $MgCl_2$, 5% glycerol, 1× protease inhibitors, pH7.4) and aliquoted into 1.5 mL tubes. Membranes pellets are collected at max speed in a table top centrifuge (14000×g for 30 min) at 4° C. The supernatant is removed and pellets are frozen and stored at −80° C. until use.

ADSoRB process using membranes and centrifugation: Membrane pellets are thawed and resuspended to homogeneity in cold Binding Buffer (20 mM HEPES, 10 mM $MgCl2$, 0.1 mM EDTA, 0.1% BSA, pH7.4) and aliquoted into 1.5 mL tubes at ~1×10$^{12}$ receptor molecules per selection (or less depending on round). The membrane pellet is recovered at 18000×g for 10 min at 4° C. Microsomes are resuspended in a library surrogate (KD concentration of [$^3$H]agonist radiotracers like [H]DAMGO or [$^3$H]U69593, or [H]antagonist radiotracer like [$^3$H]Naloxone) and incubated for 2 hr at RT with end-over-end mixing. The membrane pellet is recovered at 18000×g for 10 min at 4° C. Supernatant is removed and membrane pellet washed by resuspension in 1 mL cold binding buffer. Membranes are recovered at 18000×g for 10 min at 4° C. This step is repeated four times for a total of 5 washes, with the last wash split according to the different elution conditions (e.g. buffer or GPPNHP). The final wash is removed and the pellet is resuspended in 500 μL of binding buffer or GPPNHP elution buffer. Incubate at RT for various times (typically 1 to 5 min). High speed centrifugation is used to pellet the membrane and the supernatant containing the eluted ligands is saved for downstream processing. In the case of a radiotracer we performed scintillation counting to detect the number of ligands at each step. Elution steps can be repeated as needed to recover the ligand. Functional elution can be followed with general elution (e.g. 0.2M Glycine, pH 2.2) for recovery of all other binders.

Results

Figure 2A:
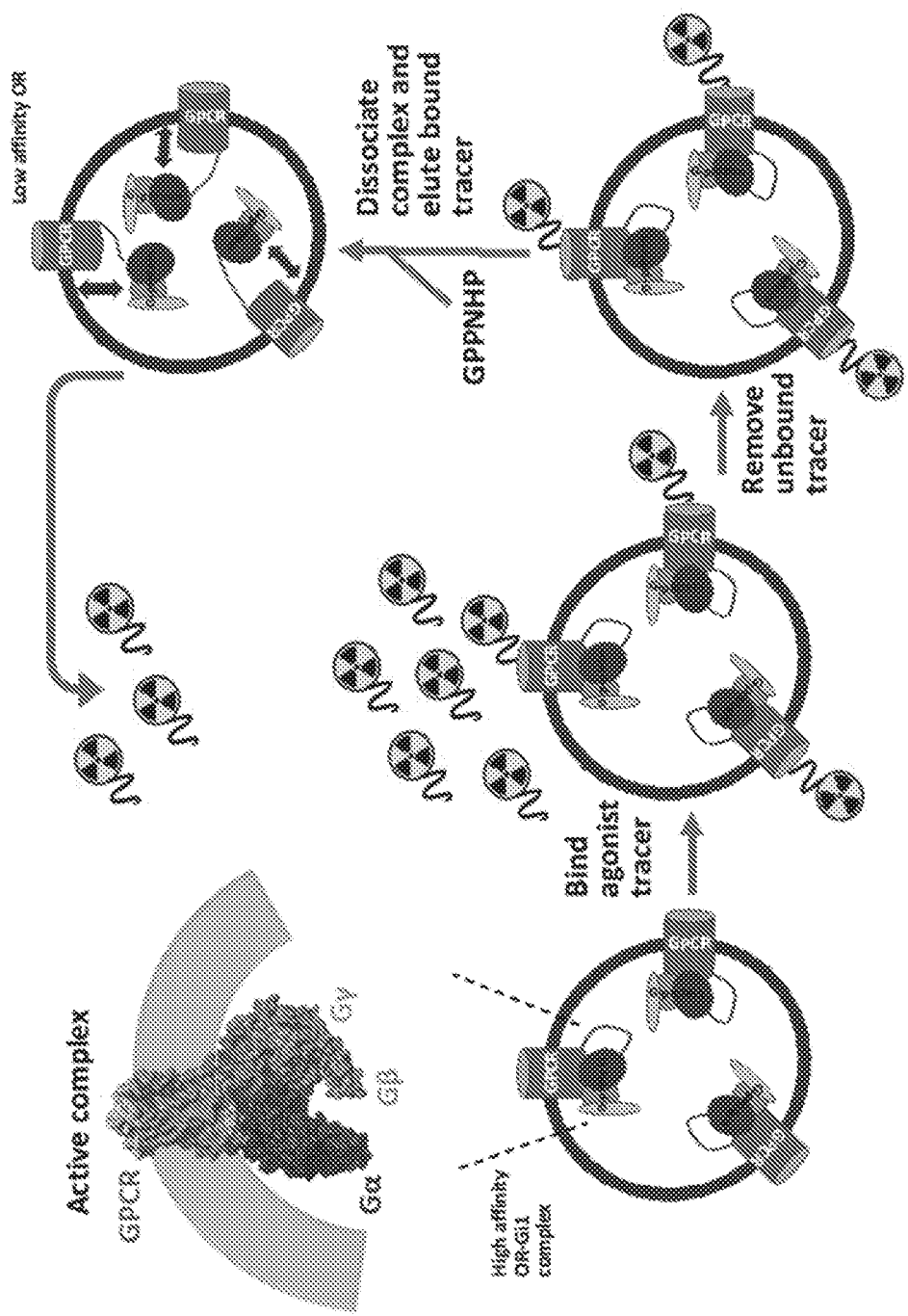
FIG. 2A is the experimental workflow for screening of an opioid receptor fused to the Gαi1 protein (OR-Gi1 active complex) expressed in a native membrane microsome. A radiolabeled agonist is used as the positive control to assess the performance of the screen in place of a large library (i.e. to quantify agonist binding, washing, and elution).

FIG. 2B shows quantification of ADSoRB screen at the mu-opioid receptor (MOR) fused to Gαi1 protein. High adsorption to the active, high affinity complex manifests as low unbound counts per minute (cpm), low cpms in the wash, and a large elution upon complex dissociation/uncoupling with GPPNHP (30% of total agonist added) versus buffer control (2% of total agonist added).

FIG. 2C shows quantification of ADSoRB screen at the kappa-opioid receptor (KOR) fused to Gαi1 protein. High adsorption to the active, high affinity complex manifests as low unbound counts per minute (cpm), low cpms in the wash, and a large elution upon complex dissociation/uncoupling with GPPNHP (20% of total agonist added) versus buffer control (3% of total agonist added). Functional elution with GPPNHP is greater than with a competitive antagonist like 10 uM naloxone.

Figure 2D:
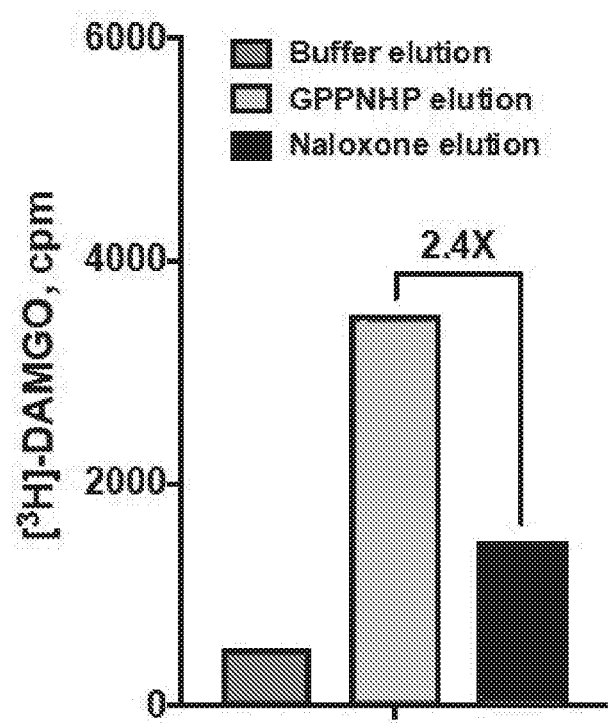
FIG. 2B shows quantification of an ADSoRB screen at the μ-opioid receptor (MOR) fused to Gαi1 protein (MOR-Gi1). High adsorption of the tritiated agonist [3H]DAMGO to the active complex manifests as low unbound counts per minute (cpm), low cpms in the wash, and a large elution upon complex dissociation/uncoupling with GPPNHP (30% of total agonist added) versus buffer control (2% of total agonist added).
FIG. 2C shows quantification of an ADSoRB screen at the k-opioid receptor (KOR) fused to Gαi1 protein. High adsorption of the tritiated agonist [3H]U69593 to the active complex manifests as low unbound counts per minute (cpm), low cpms in the wash, and a large elution upon complex dissociation/uncoupling with GPPNHP (20% of total agonist added) versus buffer control (3% of total agonist added). Functional elution with GPPNHP is greater than with a competitive antagonist like 10 μM naloxone (FIG. 2D), reflecting slow dissociation of the agonist tracer from the active complex and inefficient displacement by competitor.
FIGS. 2E and F show quantification of a proof-of-concept ADSoRB screen at the unfused MOR (low affinity) and MOR-Gαi1 expressing membranes. In panel E the tracer is the antagonist [H]Naloxone, and in FIG. 2F the tracer is the efficacious agonist [H]DAMGO.
FIG. 2G shows functional elution with GPPNHP can be enhanced by the addition of sub-saturating concentrations of a competitive ligand. As shown here, the amount of functionally eluted peptide agonist can be doubled by the addition of 100 nM naloxone. It is likely that sub-saturating concentrations of competitor enhance elution by keeping the agonist from re-binding the low-affinity state of the receptor. Compared to its weak elution from the coupled/high affinity state of the receptor, naloxone is now more effective at displacing the agonist from the uncoupled receptor.

FIG. 2D shows quantification of ADSoRB screen at the mu-opioid receptor unfused (MOR) and fused to Gαi1-RLuc8 chimera (MOR-Gi1RLuc). The radiotracer in this experiment is the antagonist [3H]-Naloxone. Low adsorption of antagonist to both the unfused (inactive) MOR and fused MOR-Gi1Rluc (active) manifests as high unbound counts per minute (cpm) (on average 55% of total added for both membrane types), modest cpms in the wash (on average 25% for both), and a very small elution upon complex dissociation with GPPNHP (1% of total for MOR and 2.5% for MOR-Gi1RLuc) versus buffer control (~0.5% of total for both). Notably, the antagonist showed no real preference for low or high affinity states and would not be highly represented in the eluate of an ADSoRB screen.

Figures 2E, 2F:
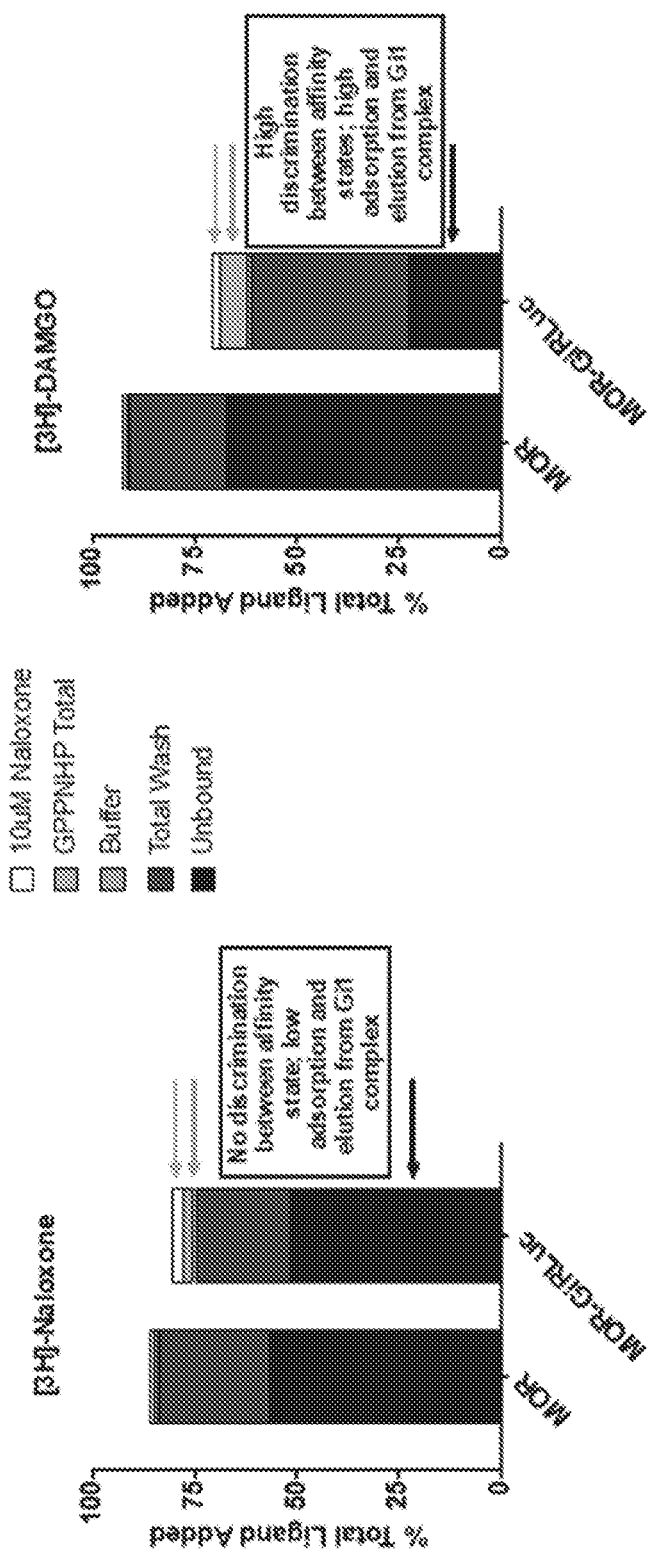
Figure 2G:
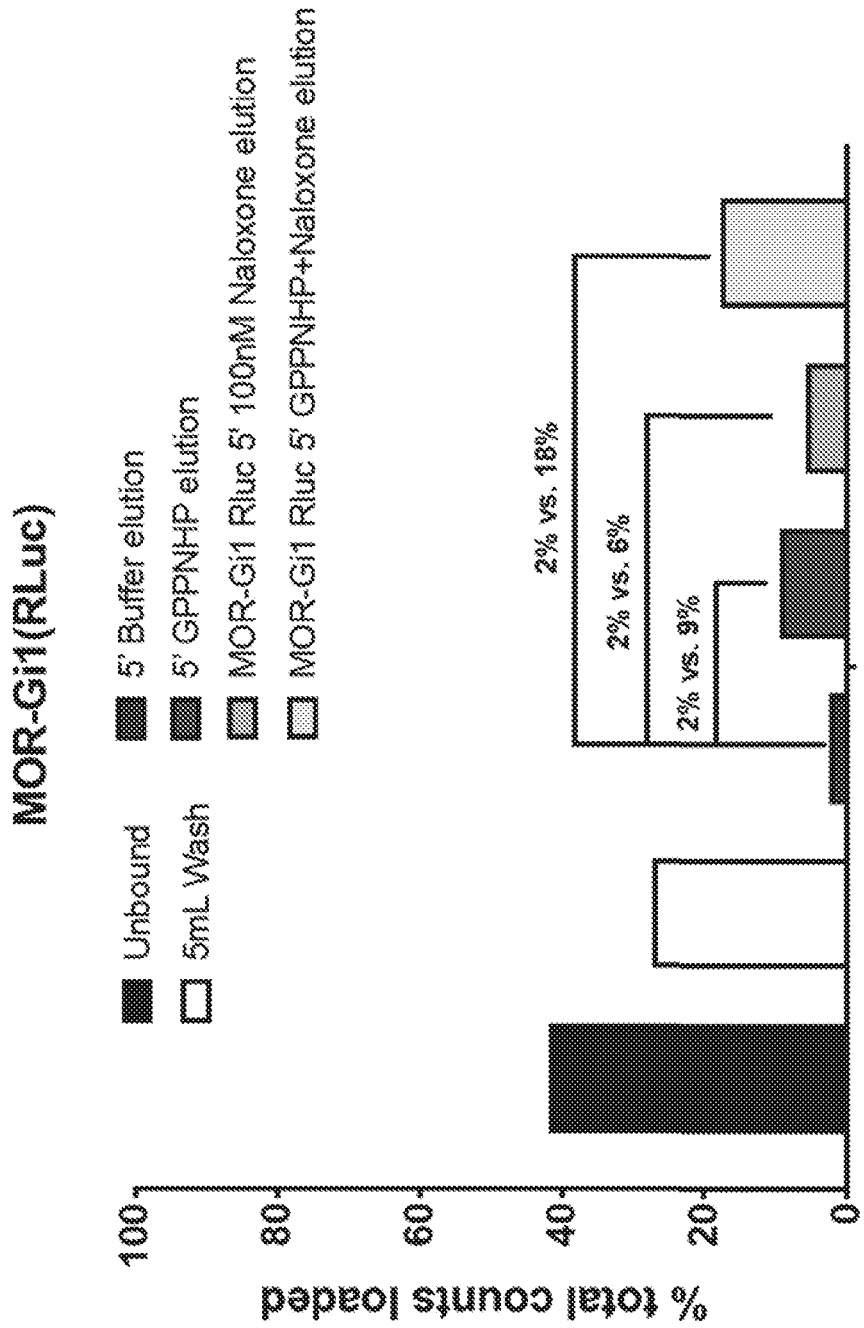

FIG. 2E shows the same experimental setup as in FIG. 2D but instead uses an agonist radiotracer ([3H]DAMGO), low affinity MOR membranes, and high affinity MOR-Gi1RLuc complexes. Quantification of counts per minute (cpm) shows high preferential adsorption of the agonist to the MOR-Gi1RLuc complex (23% unbound tracer) compared to unfused MOR (67% unbound tracer). Upon GPPNHP treatment, a very small fraction of agonist eluted from low affinity MOR (0.8% of total agonist) vs. the relatively large fraction that eluted from the high affinity MOR-Gi1RLuc complex (7% of total agonist). Compared to the antagonist tracer experiment in FIG. 2D, ADSoRB preferentially binds and elutes agonist ligands from GPCR-transducer complexes. In a multi-round enrichment paradigm, high efficacy agonists should predominate in the functionally eluted fractions of later rounds.

Example 2: Development of a Scalable, Cell-Type-Agnostic Platform for Profiling GPCR Signaling at Single Transducer Resolution G Protein Coupled Receptors (GPCRs) are the most widely drugged protein family in the human genome. It is recognized that signaling events following GPCR activation by a ligand can proceed disproportionately through multiple G-protein pathways. This signaling "bias" makes it possible to tune the physiological response for each receptor-ligand interaction, thus setting up the potential to develop safer and more efficacious biased drugs (Manglik A et al. Nature. 2016 Sep. 8; 537(7619):185-190). However, there are limited assays that can differentiate between G proteins, and many of these are further confounded because of their dependence on downstream signaling events and manifest qualities such as amplification and cell-type variation. The ability to measure the extent to which any given ligand-GPCR signaling response is biased would advance the scope of known GPCR pharmacology and help inform drug-discovery and optimization efforts. This disclosure presents a comprehensive signaling assay to avoid these specific caveats.

For the following, placement of the luminescent donor and fluorescent acceptor can be exchanged (i.e. it is not necessary that the luminescent donor be on the Gα, and could for the intended purposes be located on the Gβ or Gγ subunit).

Peptide sequences for Gα subunits are used to generate maps of known or putative flexible or disordered domains. This can be done either by using published structures or through modeling of amino acid sequences for less well understood Gα subunits against known structures with high similarity (Table 3). Plasmids containing human Gα, Gβ, and Gγ constructs were obtained from public resources, except for Gα12 and Gαgustducin, which were synthesized as gene blocks. All constructs were subcloned into pcDNA5/FRT/TO.

TABLE 3

List of Gα proteins and the PDB ID for the structure used to build homology models in swiss model.

| Gαi1 | 3UMS |
| Gαi2 | 3UMS |
| Gαi3 | 5KDO |
| GαoA | 3C7K |
| GαoB | 3C7K |
| GαZ | 5KDO |
| GαGust | 3V00 |
| GαsS | 3SN6 |
| GαsL | 3SN6 |
| GαOlf | 3SN6 |
| GαQ | 3AH8 |

TABLE 3-continued

List of Gα proteins and the PDB ID for the structure used to build homology models in swiss model.

| Gα11 | 3AH8 |
| Gα14 | 4GNK |
| Gα15 | 3AH8 |
| Gα12 | 1ZCA |
| Gα13 | 3AB3 |

Chimeric constructs (e.g. Gα-RLuc8 and Gγ-GFP2 constructs) were generated via Gibson assembly-type methods. Gγ-GFP2 constructs were generated by amplification of the backbone construct (e.g. pcDNA-Gγ) from the N-terminal start codon and adding homology to the C-terminus of GFP flanked by a short flexible linker sequence (GSAGT). GFP2 sequences were amplified by PCR, adding homology to the pcDNA backbone at the 5' end, and homology to the N-terminus of the Gγ sequence at the 3' end. Backbone and insert constructs were co-incubated with Gibson-assembly master mix and transformed into competent E. coli. Gα-RLuc8 constructs were generated by linearizing a single backbone template for each region (e.g. αA-αB linker region, αB-αC helical region, Switch III), amplifying outwards from the 5' and 3' ends of the beginning of the respective regions—producing a linearized construct lacking that sequence. These deleted codons were filled in with RLuc8 insertion sequences by overhang PCR while adding a flexible SGGGS linker, the missing codon sequences flanking the appropriate insertion site, and homology to the 5' and 3' end of the linearized backbone. These were incubated with Gibson-assembly master mix to assemble Gα-RLuc8 chimeric constructs containing a fully intact Gα with an RLuc8 sequence, one for each amino-acid position within the targeted region.

For GPCR-fusion proteins, the optimal Gα-RLuc8 chimera is fused via its N-terminus to the C-terminus of a GPCR using standard cloning methods. See the Genbank formatted example of a receptor-Galpha-Rluc fusion protein (Neurotensin+Gq) provided below.

Figure 3B:
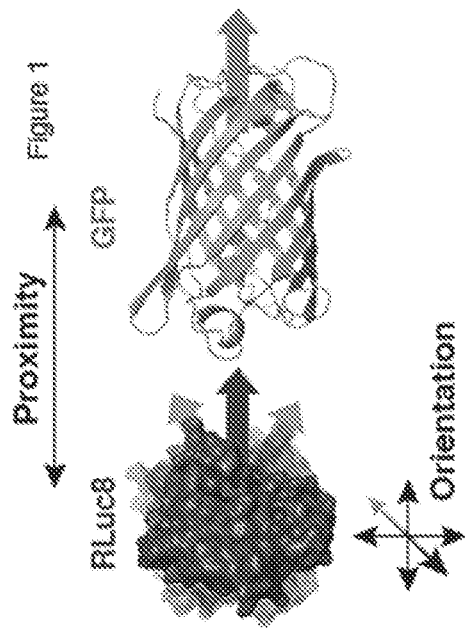
FIG. 3B demonstrates that resonance energy transfer (RET) efficiency between the luminescent and fluorescent proteins depends on both proximity and orientation of their dipole moments. Protein regions can be targeted for RLuc8 or GFP2 insertion, but the precise location for optimal RET cannot be readily predicted in such conformationally dynamic proteins.
Figure 5B:
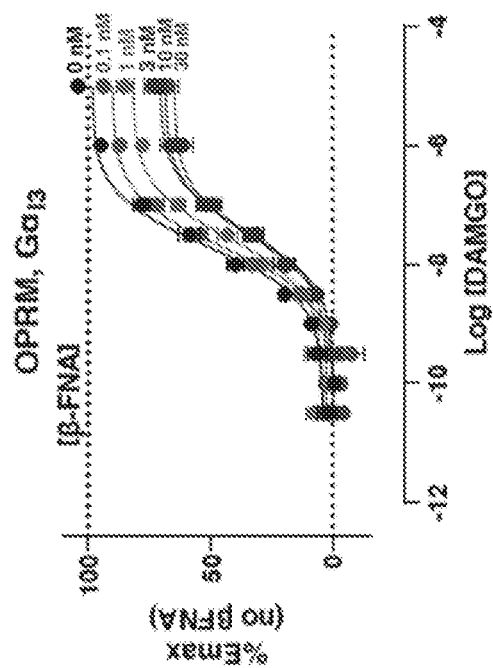
In FIG. 5B, alkylation of the μ-opioid receptor (MOR) with increasing β-FNA treatment shows a minimal effect of receptor reserve (spare receptors) evidenced by a strong inhibition of maximal efficacy and minimal effect on potency. A test for linear trend in decreasing Emax with β-FNA treatment was significant with a large effect size (FIG. 5C, $F(1,52)=180.6$, $p<0.0001$; $r2=0.7502$), while the effect on potency was weak (FIG. 5D, $F(1,52)=6.793$, $p=0.0119$, $r2=0.1005$).
Figure 5A:
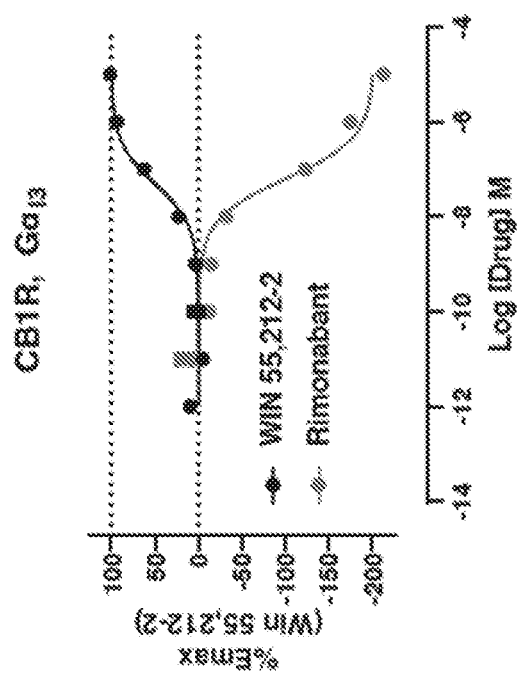
FIG. 5A shows that TRUPATH is sensitive to inverse agonists as concentration-response curves for the constitutively active cannabinoid 1 receptor (CB1R) at Gαi3 show a small full agonist response (WIN 55,212-2) and large effect of the inverse agonist (Rimonabant).
Figure 5D:
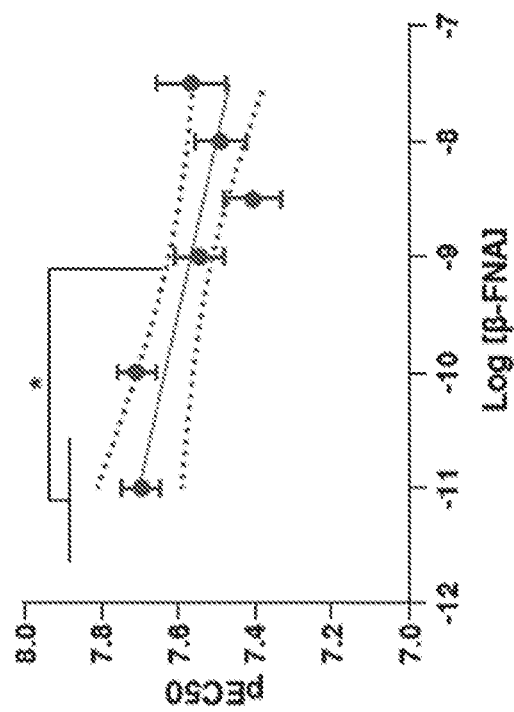
Figure 5C:
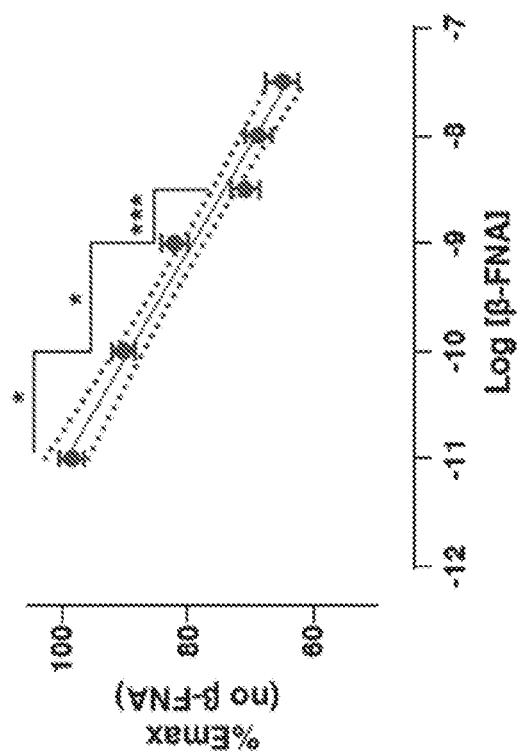
Figure 6A:
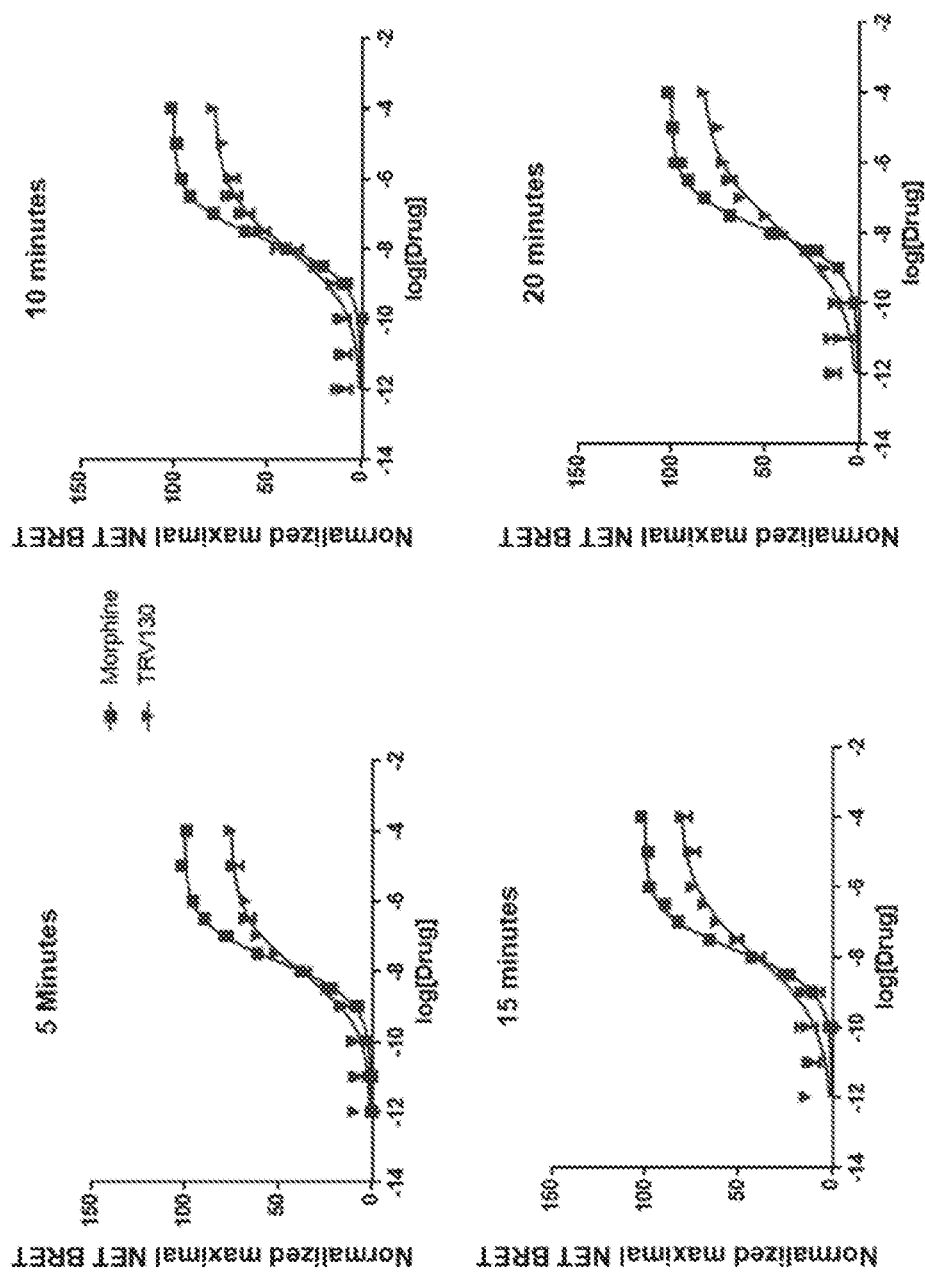
FIGS. 6A to 6C show the fusion BRET system provides an accurate estimation of the kinetics of receptor activation/equilibration. The substrate appears stable >1 hour and thus kinetics can be measured by staggered addition of drug followed by simultaneous addition of substrate, or through repeated measurements. Here, the MOR (FIG. 6A) and HTR1E (FIG. 6B) receptors show activation kinetics.
Figure 6B:
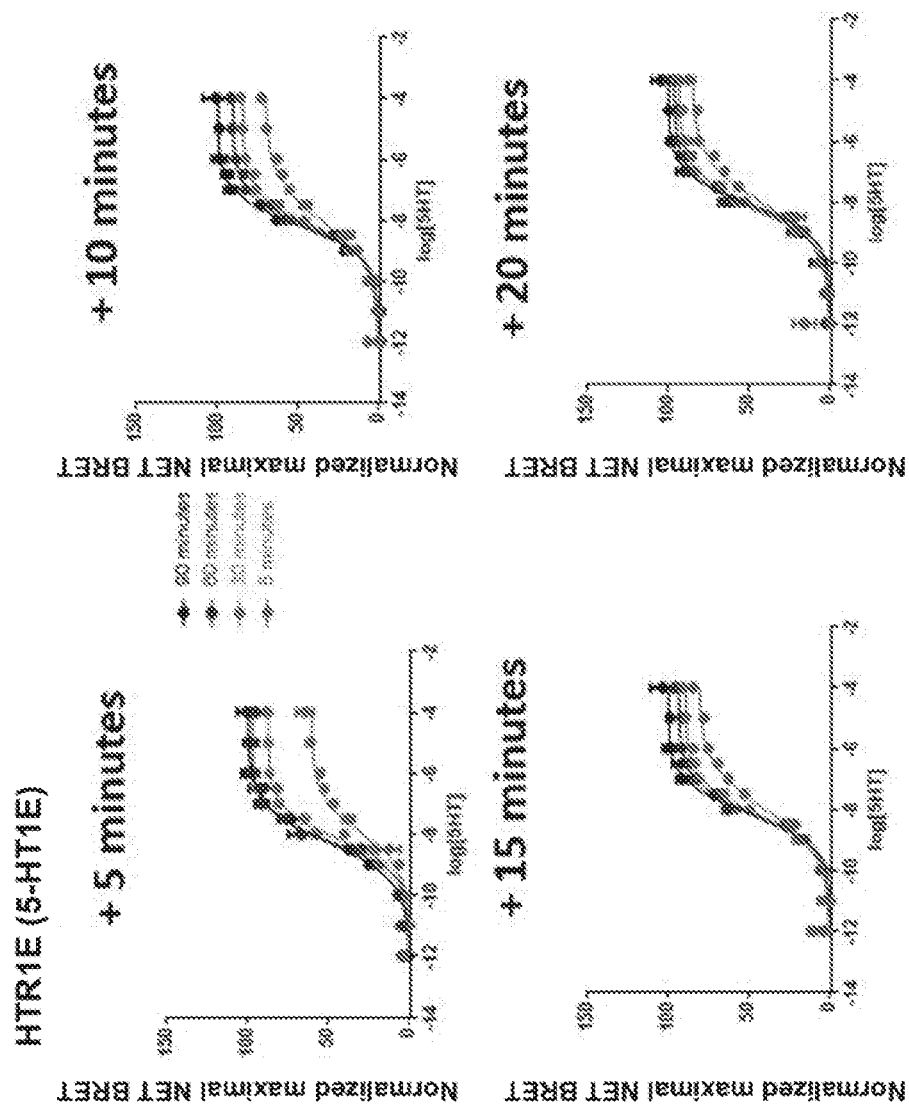
Figure 6C:
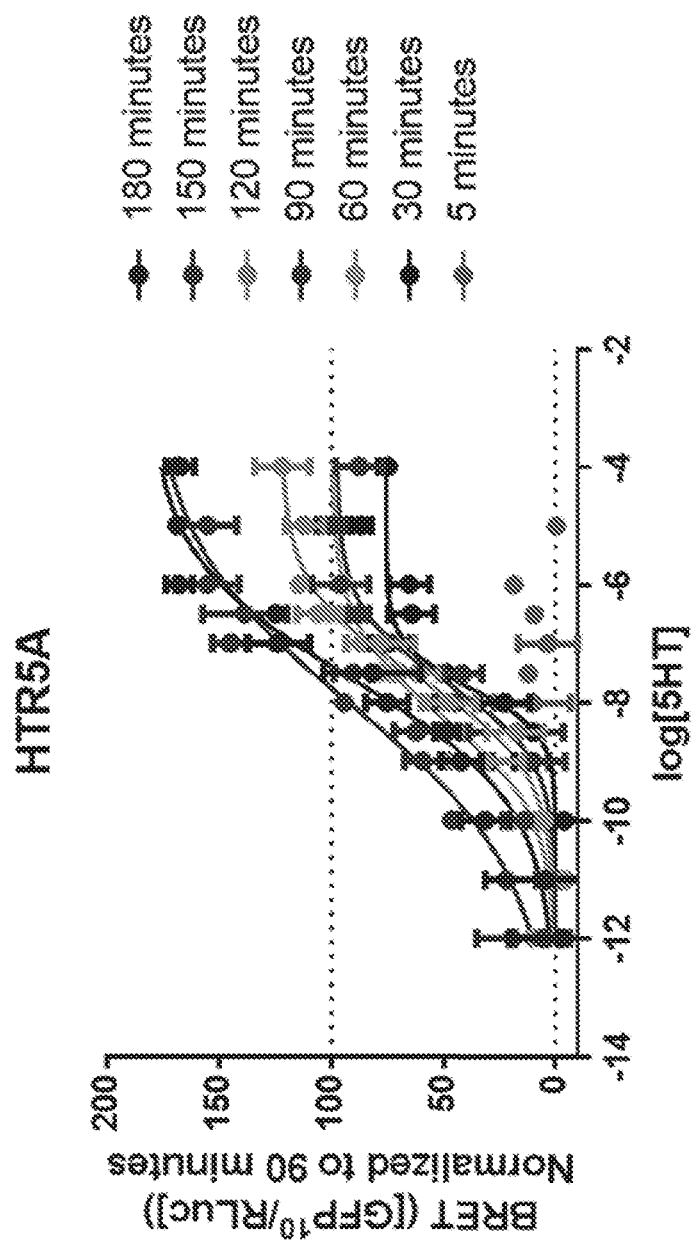
Figure 7A:
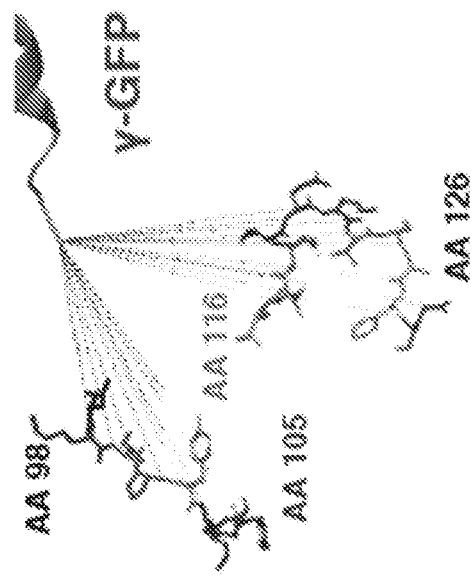
FIG. 7A uses the exemplar sensor Gαq to illustrate how the crystal structure of the inactive Gαq/Gβ1/γ2 heterotrimer (PDB 3AH8) was used to first identify regions within the alpha-helical domain (red box) for RLuc8 insertion that were close to the predicted N-terminus of the Gγ-subunit (green box). For naming, we used the position of the first amino acid in the linker-RLuc8 in the full protein sequence. For example, insertion of RLuc8 following the lysine at position 97 in Gαq is named Gαq(98)RLuc8. Twenty Gαq-RLuc8 fusion proteins were generated at each amino acid spanning the linker regions between αA-αB and between αB-αC helices.
Figure 7A:
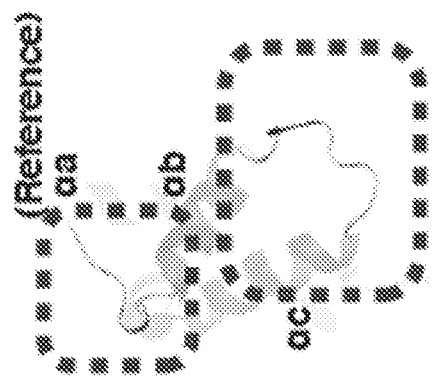
Figure 7A:
Figure 7E:
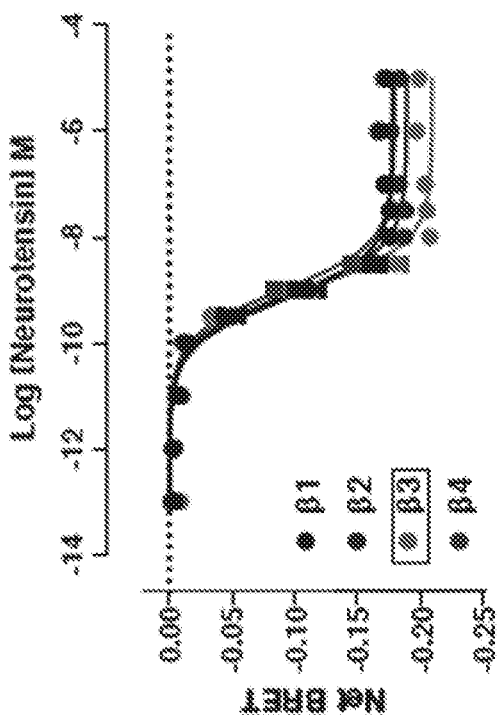
In FIG. 7B each chimera was evaluated in a primary concentration-response assay using the Gαq-coupled Neurotensin receptor. Performance was evaluated as fold-increase in dynamic range (Net BRET) relative to the reference construct (AA position 98 in Gαq). The top five insertion positions 119, 122, 123, 125,126 (boxed) were confirmed in a secondary screen (three biological replicates), identifying position 125 as the optimal Gαq-Rluc8 chimera insertion site (FIG. 7C, boxed). Next, a 'Gγ-GFP2' screen (FIG. 7D) was performed with Gαq(125)-Rluc8 to select the optimal GFP-acceptor construct (three biological replicates) when paired with 12 different N-terminally fused Gγ-GFP2 constructs and a co-precipitated mixture of the four major Gβ subunits. The Gγ9-GFP2 chimera provided the largest signal and was next screened alongside Gαq(125)-Rluc8 and each of the four major Gβ subunits (three biological replicates) (FIG. 7E). Stepwise optimization determined that Gαq(125)-Rluc8/Gβ3γ9-GFP2 was the optimal biosensor composition.
In FIG. 7F, biosensor functionality was confirmed in a screen of four well-documented Gαq-coupled receptors.
Figure 7D:
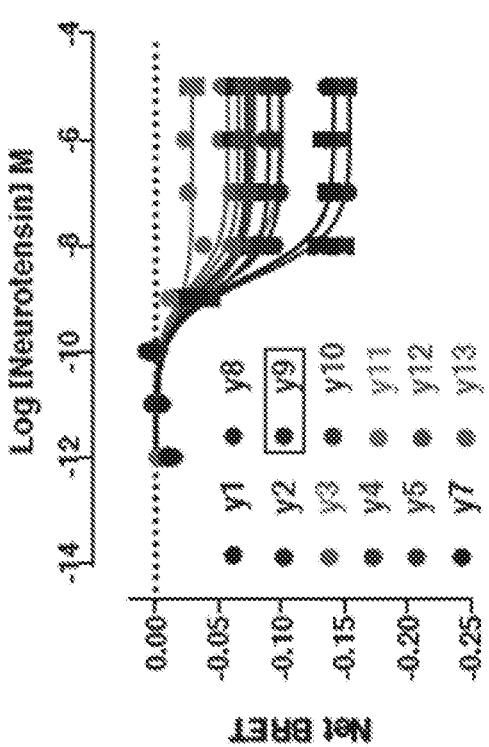
Figure 7F:
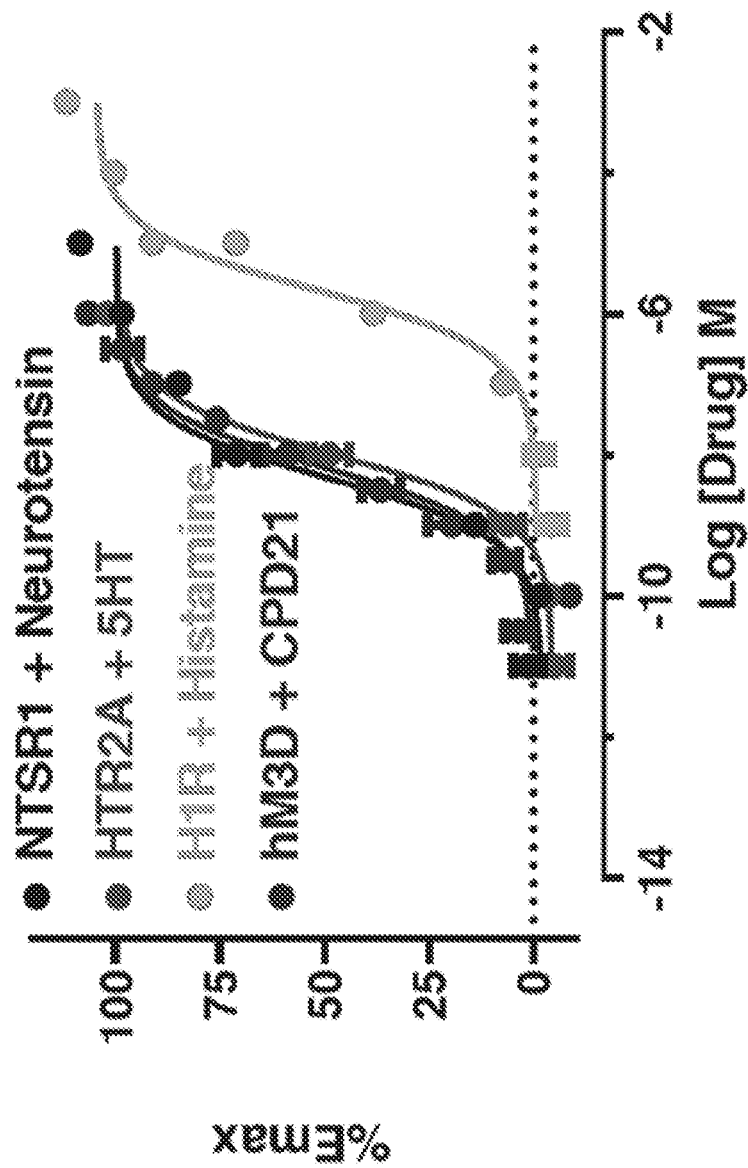
Figure 8A:
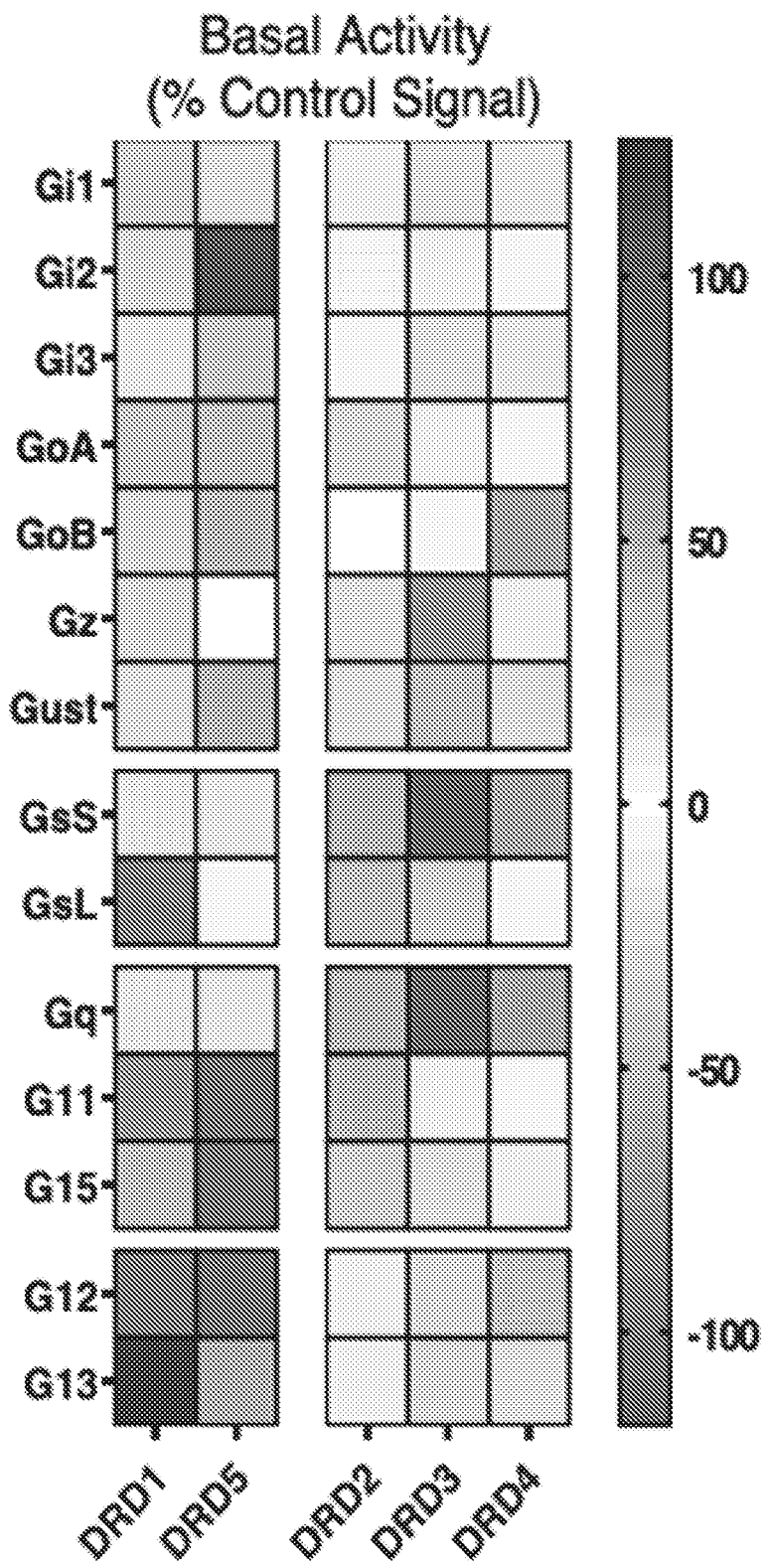
FIGS. 8A to 8E show constitutive activity of dopamine family receptors (DRD1-5), which reveals unexpected promiscuity.
Figure 8C:
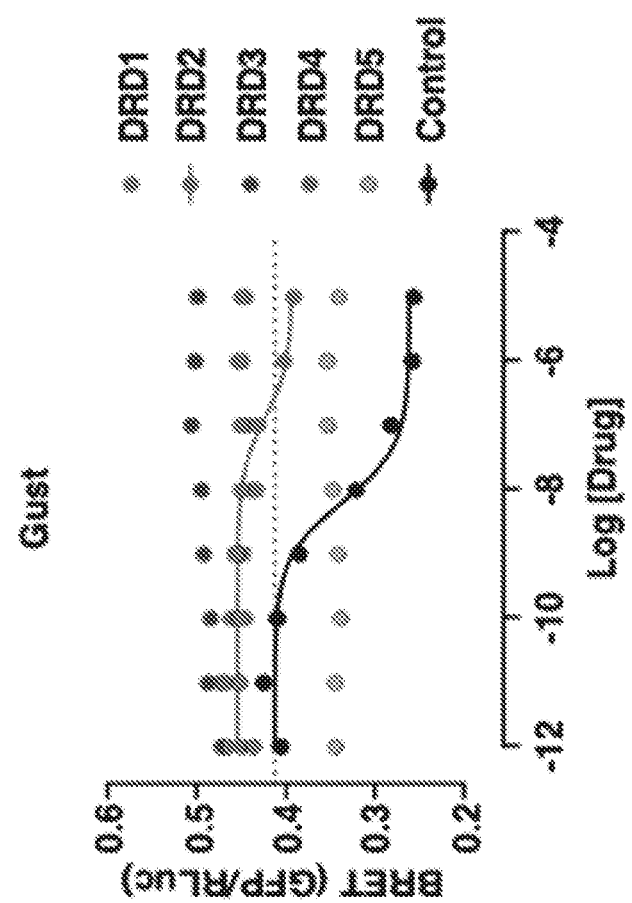
Figure 8B:
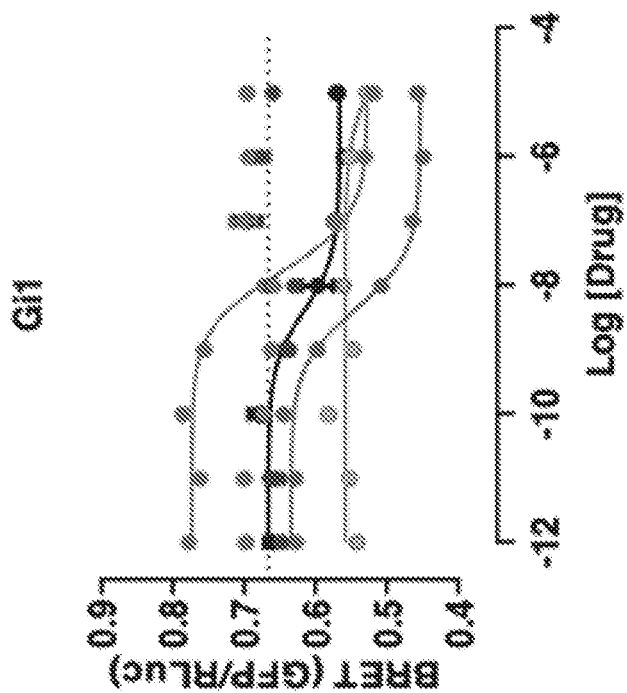
Figure 8E:
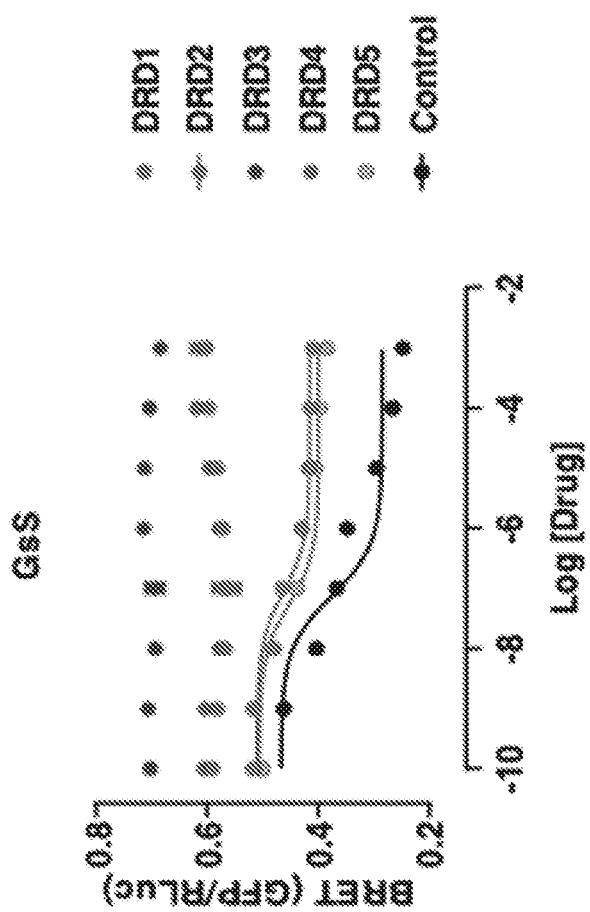
Figure 8D:
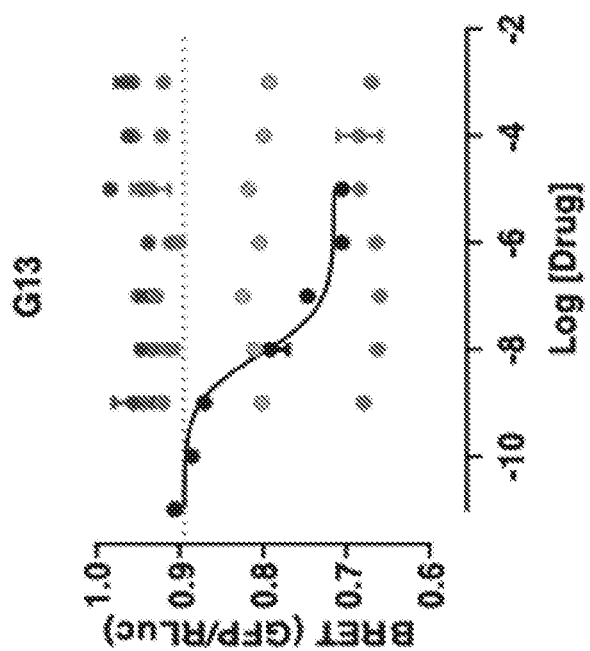
Figure 9:
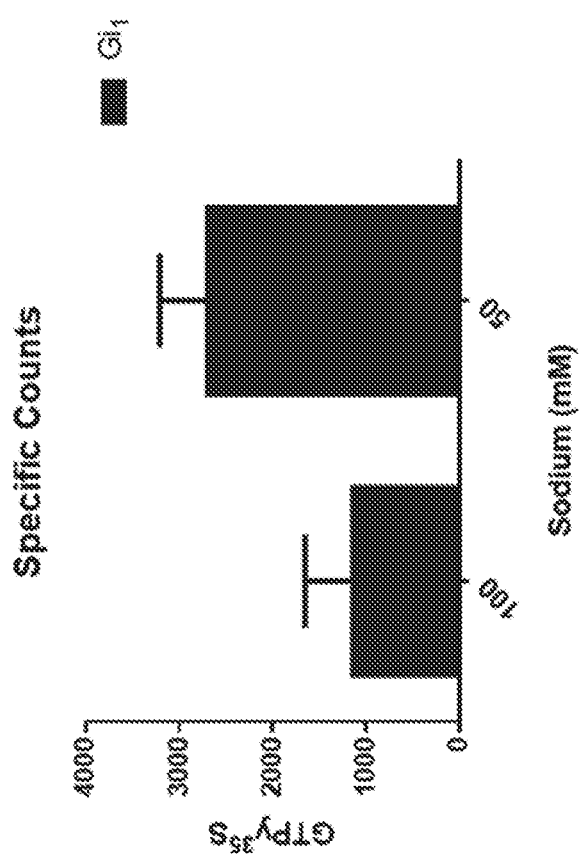
FIG. 9 shows via a GTPγ³⁵S loading assay using GPCR-transducer fusion constructs (MOR-Gi1) that GPCRs are responsive to negative allostery by sodium ions (right panel). As described in the summary, this is useful for identifying transducer preferences without a ligand in addition to the method of FIG. 8.

Biosensor optimization can be performed as follows using either a co-transfection of receptor and GαRluc variants or an N-terminally fused GPCR-GαRluc chimera (FIG. 3). The following text describes optimization in the context of a GPCR-Gα fusion but can be applied to a "non-fused" Gα construct. First identify a suitable prototype GPCR if not using one already fused to the Gα's N-terminus. Then, transfect equal ratios of the GPCR and optimal biosensor plasmids containing Gβi1 2, 3, or 4, and a fluorescently tagged Gγ subunit 1 through 13. The standard Gβ1Gγ2-GFP2 dimer is a good starting point. Any combination can be tried at first (including switching the fluorescent protein from the Gγ to the Gβ subunit) if little BRET is observed. After transfection, cells can be plated in a plate suitable for use in a luminescence/fluorescence plate reader (or read right away if transfected directly in such a plate). Treatment of wells with luminescent substrate and a known agonist (either at single points or to produce a dose-response curve) can be used to observe the relative change in BRET from basal conditions. The top 5 insertion sites based on NET BRET (number can be modified based on needs) can then be retested to be confident that the optimal insertion site has been identified (FIG. 3F). All Gβ subunits can then be co-precipitated and the optimal construct transfected in parallel with each fluorescently-tagged Gγ subunit (separate transfections for each Gγ subunit, FIG. 3G). Alternately this can be done without co-precipitating by running a large matrix. The order of this can be reversed if/when tagging the Gβ subunit with the fluorescent acceptor. A dose-response assay may be performed to determine the optimal donor/acceptor pair. If a full matrix for GβGγ dimers was not performed, the optimal Gα-RLuc (or GPCR-GαRLuc fusion) and the optimal acceptor construct can be taken, and then each of the untagged Gβ or Gγ substituents can then be separately transfected (FIG. 3H). A concentration response experiment can be performed to verify the optimal heterotrimeric substituents.

The following is a Genbank formatted example of a receptor-Gα-Rluc fusion protein (Neurotensin-Gα-Rluc):

```
LOCUS       Neurotensin_GqRluc8 3522 bp ds-DNA linear 28 Nov. 2018
DEFINITION  .
FEATURES    Location/Qualifiers misc_feature    1360..1365
                /label = "Age I"
                /ApEinfo_revcolor = #d59687
                /ApEinfo_fwdcolor = #d59687 misc_feature    1846..1871
                /label = "rluc8 FWD homology"
                /ApEinfo_revcolor = #f8d3a9
                /ApEinfo_fwdcolor = #f8d3a9 misc_feature    1846..1863
                /label = "Linker F"
                /ApEinfo_revcolor = #75c6a9
                /ApEinfo_fwdcolor = #75c6a9 misc_feature    1474..1845
                /label = "Gq Fragment 1"
                /ApEinfo_revcolor = #c7b0e3
                /ApEinfo_fwdcolor = #c7b0e3 misc_feature    1453..1458
                /label = "TEV Cut Site"
                /ApEinfo_revcolor = #b7e6d7
                /ApEinfo_fwdcolor = #b7e6d7 misc_feature    1354..1359
                /label = "ClaI"
                /ApEinfo_revcolor = #75c6a9
                /ApEinfo_fwdcolor = #75c6a9 misc_feature    1864..2796
                /label = "rluc8"
                /ApEinfo_revcolor = #ff9ccd
                /ApEinfo_fwdcolor = #ff9ccd misc_feature    1366..1446
                /label = "V2 Tail"
                /ApEinfo_revcolor = #ffef86
                /ApEinfo_fwdcolor = #ffef86 misc_feature    2815..3522
                /label = "Gq Fragment 2"
                /ApEinfo_revcolor = #84b0dc
                /ApEinfo_fwdcolor = #84b0dc misc_feature    1447..1452
                /label = "Age I"
                /ApEinfo_revcolor = #b4abac
                /ApEinfo_fwdcolor = #b4abac misc_feature    1250..1255
                /label = "KOZAK"
                /ApEinfo_revcolor = #9eafd2
                /ApEinfo_fwdcolor = #9eafd2 misc_feature    1354..1473
                /label = "Linker"
                /ApEinfo_revcolor = #faac61
                /ApEinfo_fwdcolor = #faac61 misc_feature    1846..2814
                /label = "rluc8 + linker"
                /ApEinfo_revcolor = #c6c9d1
                /ApEinfo_fwdcolor = #c6c9d1 misc_feature    complement(2838..2838)
                /label = "Homo 2"
                /ApEinfo_revcolor = #c7b0e3
                /ApEinfo_fwdcolor = #c7b0e3
```

```
misc_feature    76..81
                /label = "ClaI"
                /ApEinfo_revcolor = #75c6a9
                /ApEinfo_fwdcolor = #75c6a9 misc_feature    1798..1798
                /label = "Homology 1"
                /ApEinfo_revcolor = #d59687
                /ApEinfo_fwdcolor = #d59687 misc_feature    2797..2814
                /label = "Linker"
                /ApEinfo_revcolor = #f8d3a9
                /ApEinfo_fwdcolor = #f8d3a9 misc_feature    complement(1256..1261)
                /label = "KOZAK"
                /ApEinfo_revcolor = #9eafd2
                /ApEinfo_fwdcolor = #9eafd2 misc_feature    82..3522
                /label = "Receptor-Alpha Fusion"
                /ApEinfo_revcolor = #ffef86
                /ApEinfo_fwdcolor = #ffef86 misc_feature    1..3
                /label = "Start"
                /ApEinfo_revcolor = #f8d3a9
                /ApEinfo_fwdcolor = #f8d3a9 misc_feature    82..1353
                /label = "Neurotensin"
                /ApEinfo_revcolor = #84b0dc
                /ApEinfo_fwdcolor = #84b0dc misc_feature    1459..1473
                /label = "TEV Cut Site"
                /ApEinfo_revcolor = #b7e6d7
                /ApEinfo_fwdcolor = #b7e6d7 misc_feature    4..75
                /label = "Signal/FLAG"
                /ApEinfo_revcolor = #faac61
                /ApEinfo_fwdcolor = #faac61 misc_feature    2790..2814
                /label = "Rluc8 Homology R"
                /ApEinfo_revcolor = #b4abac
                /ApEinfo_fwdcolor = #b4abac
```

(SEQ ID NO: 1)

```
  1    atgaagacga tcatcgccct gagctacatc ttctgcctgg tattcgccga ctacaaggac
 61    gatgatgacg ccagcatcga tatgcacctc aacagctccg tgccgcaggg caccctggt
121    gaacccgatg cccagccctt tcgggaccag agtccgaaa tggaagcgac gttcctggcg
181    ctcagtttga gcaatggttc tggcaatacc tcggaatccg acacggcagg gcccaacagc
241    gacctggacg tgaacactga catttattcc aaggtgctgg tgactgctat atacctggca
301    ctcttcgtgg tgggcactgt gggcaactcc gtgacactct tcactctagc gcggaagaag
361    tcactgcaga gcctgcagag cactgtgcat taccacctgg gcagcctggc actgtctgac
421    ctgcttatcc ttctgctggc catgcccgtg agctataca acttcatctg ggtacaccat
481    ccctgggcct ttgggacgc tggctgccgt ggctactatt tcctgcgtga tgcctgcacc
541    tatgccacag ccctcaatgt agccagcctg agtgtggagc gctacttggc catctgccat
601    cccttcaagg ccaagaccct catgtcccgc agccgcacca agaaattcat cagtgccata
661    tggctagctt cggcgctgct ggctataccc atgctttca ccatgggcct gcagaaccgc
721    agtgccgacg gcacgcaccc tggcggcctg gtgtgcacac ccattgtgga cacagccact
781    gtcaaggtcg tcatccaggt aacaccttc atgtccttcc tgtttccat gttggtcatc
841    tccatcctaa acaccgtgat tgccaacaaa ctgacagtca tggtgcacca ggccgccgag
```

-continued

```
 901   cagggccgag tgtgcaccgt gggcacacac aacggtttag agcacagcac gttcaacatg
 961   accatcgagc cgggtcgtgt ccaggccctg cgccacggag tcctcgtctt acgtgctgtg
1021   gtcattgcct ttgtggtctg ctggctgccc taccacgtgc gacgcctgat gttctgctat
1081   atctcggatg aacagtggac tacgttcctc ttcgatttct accactattt ctacatgcta
1141   accaacgctc tcttctacgc cagctccgcc atcaatccca tcctctacaa cctggtctcc
1201   gccaacttcc gccaggtctt tctgtccacg ctggcctgcc tttgtcctgg gtggcgccac
1261   cgccggagga agcgccccgc cttctcacgg aaggccgact cagtatcctc taaccatacc
1321   ctgagttcaa acgccactcg ggaaacgctg tacatcgata ccggtggacg caccccaccc
1381   agcctgggtc cccaagatga gtcctgcacc accgccagct cctccctggc caaggacact
1441   tcatcgaccg gtgagaacct gtacttccag ctaatgactc tggagtccat catggcgtgc
1501   tgcctgagcg aggaggccaa ggaagcccgg cggatcaacg acgagatcga gcggcagctc
1561   cgcagggaca agcgggacgc ccgccgggct ctcaagctgc tgctgctcgg gacaggagag
1621   agtggcaaga gtacgtttat caagcagatg agaatcatcc atgggtcagg atactctgat
1681   gaagataaaa gggcttcac caagctggtg tatcagaaca tcttcacggc catgcaggcc
1741   atgatcagag ccatggacac actcaagatc ccatacaagt atgagcacaa taaggctcat
1801   gcacaattag ttcgagaagt tgatgtggaa aaggtgtctg ctttttctgg tggtggtgga
1861   tccatggctt ccaaggtgta cgaccccgag caacgcaaac gcatgatcac tgggcctcag
1921   tggtgggctc gctgcaagca atgaacgtg ctggactcct tcatcaacta ctatgattcc
1981   gagaagcacg ccgagaacgc cgtgattttt ctgcatggta acgctacctc cagctacctg
2041   tggaggcacg tcgtgcctca catcgagccc gtggctagat gcatcatccc tgatctgatc
2101   ggaatgggta agtccggcaa gagcgggaat ggctcatatc gcctcctgga tcactacaag
2161   tacctcaccg cttggttcga gctgctgaac cttccaaaga aaatcatctt tgtgggccac
2221   gactgggggg ctgctctggc ctttcactac gcctacgagc accaagacag gatcaaggcc
2281   atcgtccata tggagagtgt cgtggacgtg atcgagtcct gggacgagtg gcctgacatc
2341   gaggaggata tcgccctgat caagagcgaa gagggcgaga aaatggtgct tgagaataac
2401   ttcttcgtcg agaccgtgct cccaagcaag atcatgcgga aactggagcc tgaggagttc
2461   gctgcctacc tggagccatt caaggagaag ggcgaggtta gacggcctac cctctcctgg
2521   cctcgcgaga tccctctcgt taagggaggc aagcccgacg tcgtccagat tgtccgcaac
2581   tacaacgcct accttcgggc cagcgacgat ctgcctaagc tgttcatcga gtccgaccct
2641   gggttctttt ccaacgctat tgtcgaggga gctaagaagt ccctaacac cgagttcgtg
2701   aaggtgaagg gcctccactt cctccaggag gacgctccag atgaaatggg taagtacatc
2761   aagagcttcg tggagcgcgt gctgaagaac gagcagagcg gaggaggcgg cagtgagaat
2821   ccatatgtag atgcaataaa gagtttatgg aatgatcctg aatccaggag atgctatgat
2881   agacgacgag aatatcaatt atctgactct accaaatact atcttaatga cttggaccgc
2941   gtagctgacc ctgcctacct gcctacgcaa caagatgtgc ttagagttcg agtccccacc
3001   acagggatca tcgaataccc ctttgactta caaagtgtca ttttcagaat ggtcgatgta
3061   gggggccaaa ggtcagagag aagaaaatgg atacactgct ttgaaaatgt cacctctatc
3121   atgtttctag tagcgcttag tgaatatgat caagttctcg tggagtcaga caatgagaac
3181   cgaatggagg aaagcaaggc tctctttaga acaattatca catacccctg gttccagaac
3241   tcctcggtta ttctgttctt aaacaagaaa gatcttctag aggagaaaat catgtattcc
```

```
3301        catctagtcg actacttccc agaatatgat ggaccccaga gagatgccca ggcagcccga 3361        gaattcattc tgaagatgtt cgtggacctg aacccagaca gtgacaaaat tatctactcc 3421        cacttcacgt gcgccacaga caccgagaat atccgctttg tctttgctgc cgtcaaggac 3481        accatcctcc agttgaacct gaaggagtac aatctggtct aa.
```

Example 3: TRUPATH Assays for Screening Prototypic and Understudied GPCRs for G-Protein Preferences A mammalian expression vector containing any GPCR can be used to screen the complete set of TRUPATH G protein sensors (Table 1) for any number of ligands. Alternatively, a single expression vector utilizing multiple promoter regions or IRES (or similar sites) can be employed to express the entire system from a single plasmid (described here as a triple plasmid or polycistronic vector (FIG. 30A, B).

After transfection, cells are plated in a suitable plate for the instrument/plate-reader (e.g. a 96-well plate, 384, 1536, etc). This step is unnecessary if the cells are transfected directly in such a plate.

After sufficient time to allow for expression (~36 to 48 hr), cell media is aspirated off and washed with an assay buffer (e.g. a buffered saline solution).

The order of addition of ligands or substrate can be determined by the experimenter, but in a general experiment a substrate for the luminescent enzyme is added and allowed to equilibrate in solution with the cells (optional). Test ligands are then added (single point or dose response) and either read in the plate-reader right away or after a pre-determined amount of time.

Dose response curves can be analyzed using conventional pharmacological methods (e.g. three parameter logistic model) to estimate parameters such as efficacy (Emax) and potency (EC50) (FIG. 32). For receptors with a known standard ligand, all values can be measured relative to this reference. Bias at each transducer can be calculated using published standard pharmacological formulas (e.g. Onaran H O et al. Sci Rep. 2017 Mar. 14; 7:44247) or other model free methods.

The relative efficacies can be measured by comparing the net BRET values from the experiment above against a standard receptor/alpha/ligand (e.g. Neurotensin for most G proteins except for Gs isoforms (beta2-adrenergic receptor) or GαGustducin (KOR)). Once normalized to these standards, a user-defined method of bias quantification can be used.

Figures 32A, 32B:
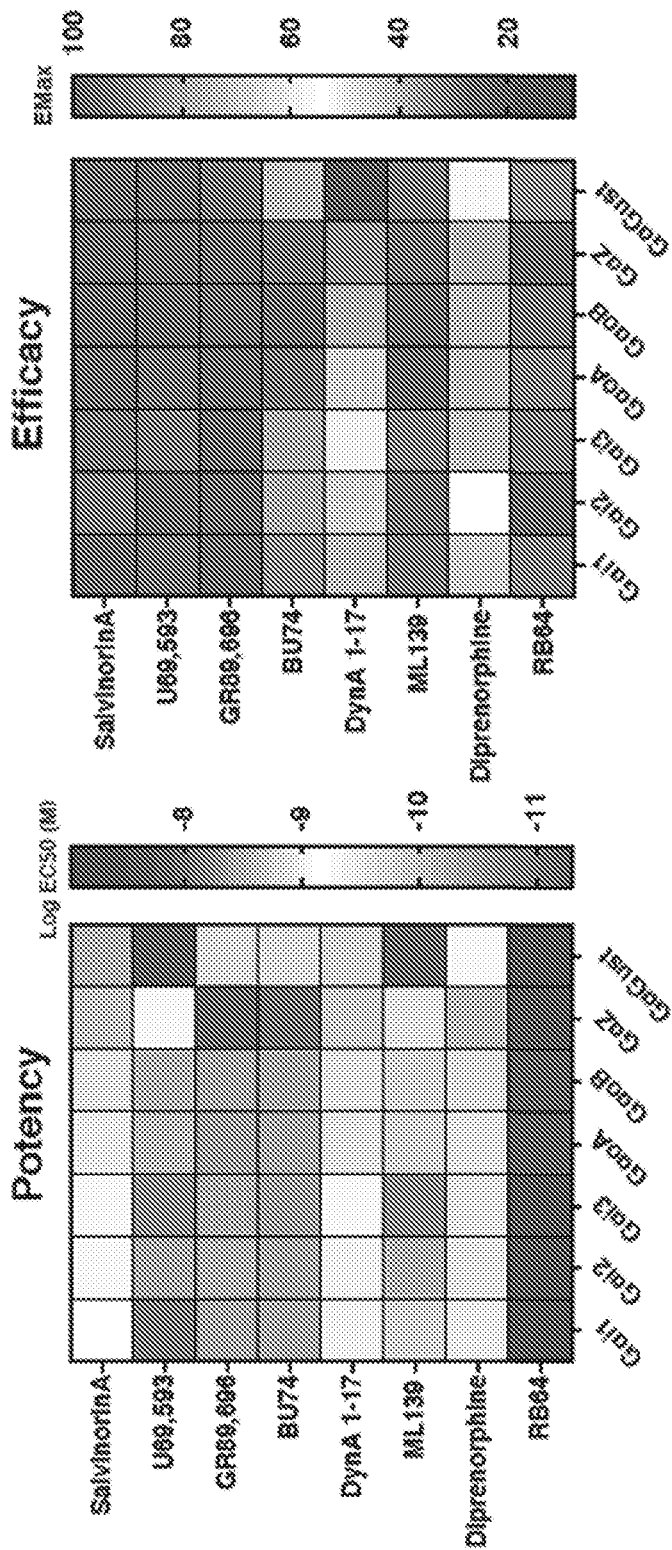
Figure 33A:
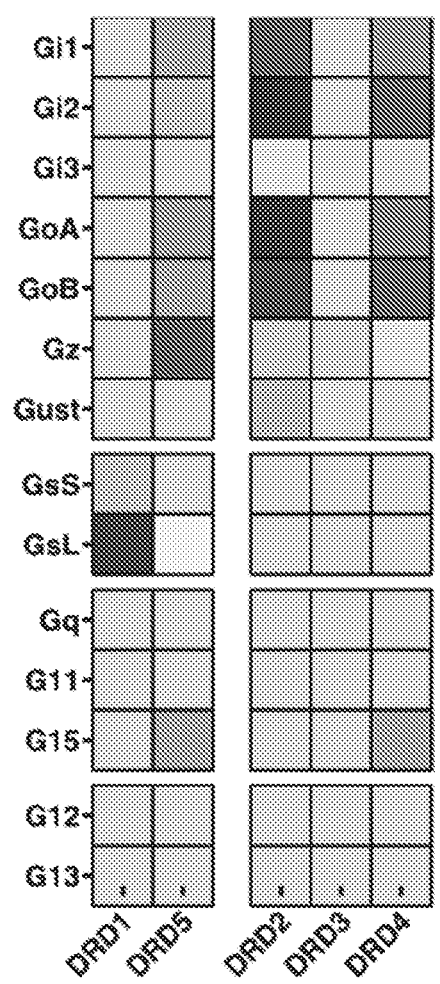
FIGS. 33A to 33D show dopamine family (D1-5) transducerome profiles for endogenous agonist dopamine.
Figure 33B:
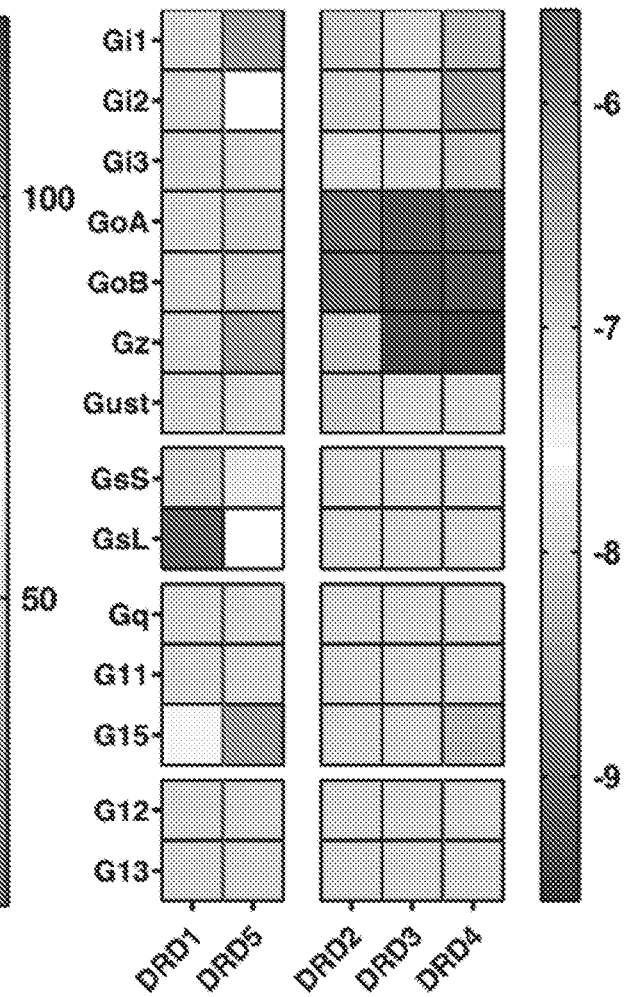
Figure 33D:
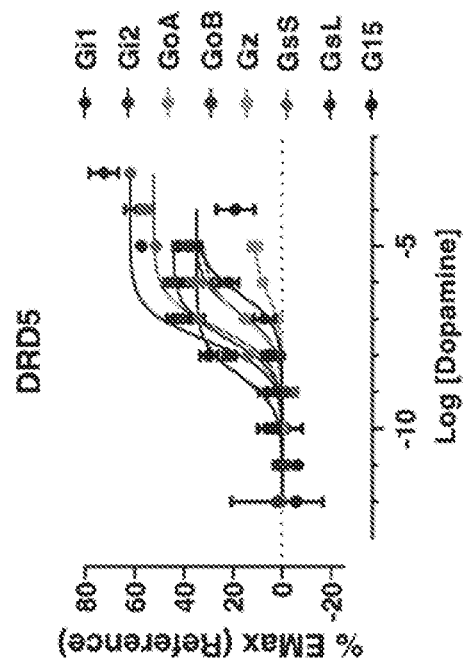
Figure 33C:
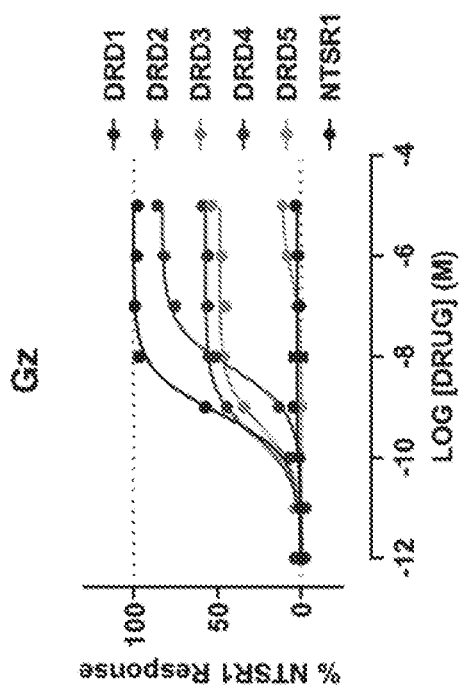
Figure 34A:
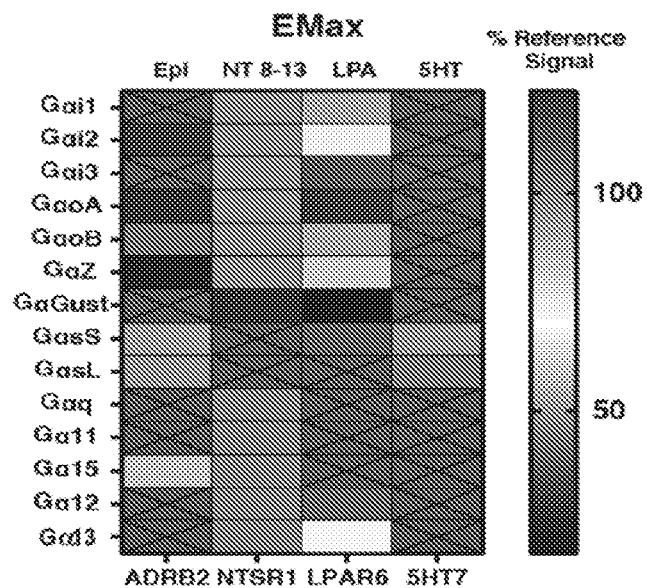
FIGS. 34A and 34B show transducerome profiles for prototypic (ADRB2 and neurotensin, NTSR1) and understudied (LPA, LPAR6 and serotonin 7, 5-HT7) receptors to demonstrate the varying degrees of promiscuity of endogenous agonists. (A) Relative amplitude (Emax or efficacy) of agonist-induced stimulation of TRUPATH biosensors is frequently nonuniform for a given receptor-ligand pair. (B) Potency (Log EC50) values across the transducerome are similarly non-uniform for many receptor-ligand pairs. Data presented as mean values t SEM. Heat map values represent mean value.
Figure 34B:
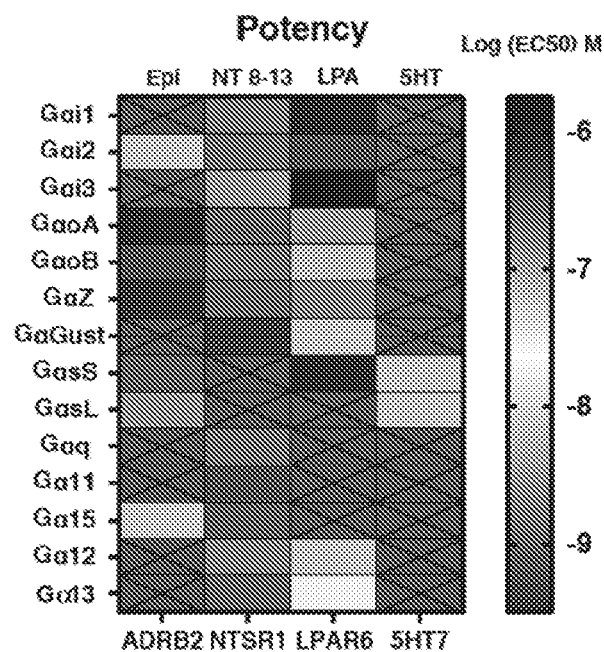

In FIG. 32, heatmaps and concentration-response curves demonstrate how a panel of KOR agonists engage Gαi/o-class TRUPATH sensors with varying potency (FIG. 32A) and efficacy (FIG. 32B). Responses were not detected at other G proteins.

In FIG. 33, heatmaps and concentration-response curves demonstrate how the endogenous agonist dopamine activates its receptors to produce different transducerome signatures. Note considerable differences amongst subclasses of dopamine receptors originally thought to signal similarly (FIGS. 33 A and B).

For comprehensive transducerome profiling of understudied receptors (FIG. 8), the basal activities of the receptor can be evaluated relative to a receptor with known low constitutive activity, or in the case of Gαi class proteins, pertussis toxin can be used. Other toxins and inhibitors for G proteins can be similarly used. For instance, toxins such as cholera or *Pasteurella multocida* toxin can be used to irreversibly activate G proteins, thus providing a theoretical "maximum" response for the assay.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for measuring G protein pathway activation by an agent, comprising
   (a) providing a system comprising:
      a G protein coupled receptor (GPCR) that is unfused or fused to a Gα protein subunit that is tagged with a fluorescent or luminescent donor or acceptor at an insertion site and incorporated into a lipid bilayer,
      a Gβ protein subunit and a Gγ protein subunit, wherein one of the Gβ protein subunit or the Gγ protein subunit is tagged with a fluorescent or luminescent donor or acceptor through insertion sites,
      wherein the insertion site for the fluorescent or luminescent donor or acceptor in the Gα protein subunit is:
         wherein the Gα subunit is a Gα(i1) subunit, the fluorescent donor or acceptor is inserted in the Gα subunit at position 91, 93, 95, 98, or 99;
         wherein the Gα subunit is a Gα(i2) subunit, the fluorescent donor or acceptor is inserted in the Gα subunit at position 91, 93, 113, 114, or 119;
         wherein the Gα subunit is a Gα(i3) subunit, the fluorescent donor or acceptor is inserted in the Gα subunit at position 98, 99, 100, 113, or 114;
         wherein the Gα subunit is a Gα(oA) subunit, the fluorescent donor or acceptor is inserted in the Gα subunit at position 91, 92, 93, 98, or 113;
         wherein the Gα subunit is a Gα(oB) subunit, the fluorescent donor or acceptor is inserted in the Gα subunit at position 91, 92, 93, 97, or 99;
         wherein the Gα subunit is a Gα(Z) subunit, the fluorescent donor or acceptor starts is inserted in the Gα subunit at position 114, 115, 116, 117, or 118;
         wherein the Gα subunit is a Gα(Q) subunit, the fluorescent donor or acceptor starts is inserted in the Gα subunit at position 119, 122, 123, 125, or 126;
         wherein the Gα subunit is a Gα(Slong) subunit, the fluorescent donor or acceptor is inserted in the Gα subunit at position 136, 137, 138, 139, or 140;
         wherein the Gα subunit is a Gα(Sshort) subunit, the fluorescent donor or acceptor starts is inserted in the Gα subunit at position 122, 123, 124, 125, or 126;
         wherein the Gα subunit is a Gα(Gustducin) subunit, the fluorescent donor or acceptor is inserted in the Gα subunit at position 114, 115, 116, 117, or 119;
         wherein the Gα subunit is a Gα(G12) subunit, the fluorescent donor or acceptor is inserted in the Gα subunit at position 134, 135, 136, 137, or 138;
         wherein the Gα subunit is a Gα(G13) subunit, the fluorescent donor or acceptor is inserted in the Gα subunit at position 125, 126, 127, 128, or 129;
         wherein the Gα subunit is a Gα(G11) subunit, the fluorescent donor or acceptor is inserted in the Gα subunit at position 239, 241, 244, 245, or 246;
         wherein the Gα subunit is a Gα(G15) subunit, the fluorescent donor or acceptor is inserted in the Gα subunit at position 244, 245, 246, 247, or 248;
      wherein if the Gα protein subunit is tagged with a fluorescent or luminescent donor, then either the Gβ protein subunit or the Gγ protein subunit is tagged with a fluorescent acceptor, and wherein if the Gα protein subunit is tagged with a fluorescent acceptor, then either the Gβ protein subunit or the Gγ protein subunit is tagged with a fluorescent or luminescent donor;
   (b) measuring a first resonance energy transfer in the system;
   (c) contacting the system with the agent;
   (d) measuring a second resonance energy transfer in the system; and
   (e) calculating G protein pathway activation (complex dissociation or rearrangement) from the difference between the second bioluminescence resonance energy transfer and the first bioluminescence resonance energy transfer.

2. The method of claim 1, further comprising repeating steps (b) to (e) for the agent at a plurality of doses and calculating a dose-response curve.

3. The method of claim 1, further comprising repeating steps (b) to (e) for the agent using a plurality of Gα/Gβ/Gγ combinations.

4. The method of claim 1, further comprising repeating steps (b) to (e) over time to determine kinetic parameters.

5. The method of claim 1, wherein the agent is a ligand with differential affinity for the GPCR in transducer-coupled versus uncoupled states.

6. The method of claim 1, wherein the system comprises a GPCR-Gα fusion or GPCR-Gα unfused pair.

7. The method of claim 1, wherein the lipid bilayer is a membrane of an intact cell, micelle, microsome, or liposome.

8. The method of claim 1, wherein other unfused or fused transducers are substituted for the G-protein.

9. The method of claim 1 wherein the insertional sites for the Gα/Gβ/Gγ combinations are:
   wherein the Gα subunit is a Gα(i1) subunit, wherein the fluorescent donor or acceptor is inserted in the Gα subunit at position 91, wherein the Gβ protein subunit is a Gβ3 subunit, and wherein the Gγ protein subunit is a Gγ9 subunit;

wherein the Gα subunit is a Gα(i2) subunit, wherein the fluorescent donor or acceptor is inserted in the Gα subunit at position 91, wherein the Gβ protein subunit is a Gβ3 subunit, and wherein the Gγ protein subunit is a Gγ8 subunit;

wherein the Gα subunit is a Gα(i3) subunit, wherein the fluorescent donor or acceptor is inserted in the Gα subunit at position 99, wherein the Gβ protein subunit is a Gβ3 or Gβ4 subunit, and wherein the Gγ protein subunit is a Gγ9 subunit;

wherein the Gα subunit is a Gα(oA) subunit, wherein the fluorescent donor or acceptor is inserted in the Gα subunit at position 92, wherein the Gβ protein subunit is a Gβ3 subunit, and wherein the Gγ protein subunit is a Gγ8 subunit;

wherein the Gα subunit is a Gα(oB) subunit, wherein the fluorescent donor or acceptor is inserted in the Gα subunit at position 92, wherein the Gβ protein subunit is a Gβ3 subunit, and wherein the Gγ protein subunit is a Gγ8 subunit;

wherein the Gα subunit is a Gα(Z) subunit, wherein the fluorescent donor or acceptor is inserted in the Gα subunit at position 114, wherein the Gβ protein subunit is a Gβ3 subunit, and wherein the Gγ protein subunit is a Gγ1 subunit;

wherein the Gα subunit is a Gα(Q) subunit, wherein the fluorescent donor or acceptor is inserted in the Gα subunit at position 125, wherein the Gβ protein subunit is a Gβ3 subunit, and wherein the Gγ protein subunit is a Gγ9 subunit;

wherein the Gα subunit is a Gα(Slong) subunit, wherein the fluorescent donor or acceptor is inserted in the Gα subunit at position 137, wherein the Gβ protein subunit is a Gβ1 subunit, and wherein the Gγ protein subunit is a Gγ1 subunit;

wherein the Gα subunit is a Gα(Sshort) subunit, wherein the fluorescent donor or acceptor is inserted in the Gα subunit at position 123, wherein the Gβ protein subunit is a Gβ3 subunit, and wherein the Gγ protein subunit is a Gγ9 subunit;

wherein the Gα subunit is a Gα(Gustducin) subunit, wherein the fluorescent donor or acceptor is inserted in the Gα subunit at position 117, wherein the Gβ protein subunit is a Gβ3 subunit, and wherein the Gγ protein subunit is a Gγ1 subunit;

wherein the Gα subunit is a Gα(G12) subunit, wherein the fluorescent donor or acceptor is inserted in the Gα subunit at position 134, wherein the Gβ protein subunit is a Gβ3 subunit, and wherein the Gγ protein subunit is a Gγ9 subunit;

wherein the Gα subunit is a Gα(G13) subunit, wherein the fluorescent donor or acceptor is inserted in the Gα subunit at position 126, wherein the Gβ protein subunit is a Gβ3 subunit, and wherein the Gγ protein subunit is a Gγ9 subunit;

wherein the Gα subunit is a Gα(G11) subunit, wherein the fluorescent donor or acceptor is inserted in the Gα subunit at position 246, wherein the Gβ protein subunit is a Gβ3 subunit, and wherein the Gγ protein subunit is a Gγ13 subunit; and wherein the Gα subunit is a Gα(G15) subunit, wherein the fluorescent donor or acceptor is inserted in the Gα subunit at position 245, wherein the Gβ protein subunit is a Gβ3 subunit, and wherein the Gγ protein subunit is a Gγ13 subunit.

10. The method of claim 1, wherein the insertional site for the Gα-protein subunit encompasses a position within the Switch III region of the Gα protein.

11. The method of claim 1 wherein any combination of the GPCR-Gα fusion, Gβ protein subunit, or the Gγ protein subunit are expressed in a single plasmid under one promoter or in a bidirectional construct.

12. The method of claim 1, wherein the GPCR, the Gα protein subunit, the Gβ protein subunit, and the Gγ protein subunit are expressed in a stably-transfected cell line.

13. The method of claim 1 wherein the GPCR, Gα protein subunit, Gβ protein subunit, or the Gγ protein subunit are derived from non-human mammalian genomes.

14. The method of claim 1 wherein the GPCR, Gα protein subunit, Gβ protein subunit, or the Gγ protein subunit are derived from non-mammalian genomes.

15. The method of claim 1, wherein the fluorescent donor is a *Renilla* luciferase (Rluc) and the fluorescent acceptor is a green fluorescent protein (GFP).

16. The method of claim 12, wherein the Gβ protein subunit is a Gβ1, Gβ2, Gβ3, or Gβ4 subunit, and the Gγ protein subunit is a Gγ1, Gγ2, Gγ3, Gγ4, Gγ7, Gγ8, Gγ9, Gγ10, Gγ11, Gγ12, or Gγ13 subunit.

17. A method for measuring G protein pathway activation by an agent, comprising (a) providing a system comprising:

a G protein coupled receptor (GPCR) that is unfused or fused to a Gα protein subunit that is tagged with a fluorescent or luminescent donor or acceptor at an insertion site and incorporated into a lipid bilayer, a Gβ protein subunit and a Gγ protein subunit, wherein one of the Gβ protein subunit or the Gγ protein subunit is tagged with a fluorescent or luminescent donor or acceptor through-insertion sites, wherein the insertion site for the fluorescent or luminescent donor or acceptor in the Gα protein subunit encompasses a position within the Switch III region of the Gα protein, wherein if the Gα protein subunit is tagged with a fluorescent or luminescent donor, then either the Gβ protein subunit or the Gγ protein subunit is tagged with a fluorescent acceptor, and wherein if the Gα protein subunit is tagged with a fluorescent acceptor, then either the Gβ protein subunit or the Gγ protein subunit is tagged with a fluorescent or luminescent donor;

(b) measuring a first resonance energy transfer in the system;

(c) contacting the system with the agent;

(d) measuring a second resonance energy transfer in the system; and (e) calculating G protein pathway activation (complex dissociation or rearrangement) from the difference between the second bioluminescence resonance energy transfer and the first bioluminescence resonance energy transfer.

* * * * *

SEQUENCE LISTING

```
<160> NUMBER OF SEQ ID NOS: 5

<210> SEQ ID NO 1
<211> LENGTH: 3522
<212> TYPE: DNA
<213> ORGANISM: Artificial Sequence
<220> FEATURE:
<223> OTHER INFORMATION: Synthetic Construct

<400> SEQUENCE: 1
atgaagacga tcatcgccct gagctacatc ttctgcctgg tattcgccga ctacaaggac      60
gatgatgacg ccagcatcga tatgcacctc aacagctccg tgccgcaggg cacccctggt     120
gaacccgatg cccagcccct ttcgggacca cagtccgaaa tggaagcgac gttcctggcg     180
ctcagtttga gcaatggttc tggcaatacc tcggaatccg acacggcagg gcccaacagc     240
gacctggacg tgaacactga catttattcc aaggtgctgg tgactgctat ataccctggca    300
```

```
ctcttcgtgg tgggcactgt gggcaactcc gtgacactct tcactctagc gcggaagaag    360
tcactgcaga gcctgcagag cactgtgcat taccacctgg gcagcctggc actgtctgac    420
ctgcttatcc ttctgctggc catgcccgtg agctataca acttcatctg ggtacaccat    480
ccctgggcct tggggacgc tggctgccgt ggctactatt tcctgcgtga tgcctgcacc    540
tatgccacag ccctcaatgt agccagcctg agtgtggagc gctacttggc catctgccat    600
cccttcaagg ccaagaccct catgtcccgc agccgcacca agaaattcat cagtgccata    660
tggctagctt cggcgctgct ggctataccc atgcttttca ccatgggcct gcagaaccgc    720
agtgccgacg gcacgcaccc tggcggcctg tgtgcacac ccattgtgga cacagccact    780
gtcaaggtcg tcatccaggt taacaccttc atgtccttcc tgtttcccat gttggtcatc    840
tccatcctaa acaccgtgat tgccaacaaa ctgacagtca tggtgcacca ggccgccgag    900
cagggccgag tgtgcaccgt gggcacacac aacggtttag agcacagcac gttcaacatg    960
accatcgagc cggtcgtgt ccaggccctg cgccacggag tcctcgtctt acgtgctgtg   1020
gtcattgcct ttgtggtctg ctggctgccc taccacgtgc gacgcctgat gttctgctat   1080
atctcggatg aacagtggac tacgttcctc ttcgatttct accactattt ctacatgcta   1140
accaacgctc tcttctacgc cagctccgcc atcaatccca tcctctacaa cctggtctcc   1200
gccaacttcc gccaggtctt tctgtccacg ctggcctgcc tttgtcctgg gtggcgccac   1260
cgccggagga agcgccccgc cttctcacgg aaggccgact cagtatcctc taaccatacc   1320
ctgagttcaa acgccactcg ggaaacgctg tacatcgata ccggtggacg caccccaccc   1380
agcctgggtc cccaagatga gtcctgcacc accgccagct cctccctggc caaggacact   1440
tcatcgaccg gtgagaacct gtacttccag ctaatgactc tggagtccat catggcgtgc   1500
tgcctgagcg aggaggccaa ggaagcccgg cggatcaacg acgagatcga gcggcagctc   1560
cgcagggaca agcgggacgc ccgccgggag ctcaagctgc tgctgctcgg gacaggagag   1620
agtggcaaga gtacgtttat caagcagatg agaatcatcc atgggtcagg atactctgat   1680
gaagataaaa ggggcttcac caagctggtg tatcagaaca tcttcacggc catgcaggcc   1740
atgatcagag ccatggacac actcaagatc ccatacaagt atgagcacaa taaggctcat   1800
gcacaattag ttcgagaagt tgatgtggag aaggtgtctg cttttttctgg tggtggtgga   1860 tccatggctt ccaaggtgta cgaccccgag caacgcaaac gcatgatcac tgggcctcag   1920
tggtgggctc gctgcaagca aatgaacgtg ctggactcct tcatcaacta ctatgattcc   1980
gagaagcacg ccgagaacgc cgtgattttt ctgcatggta acgctacctc cagctacctg   2040
tggaggcacg tcgtgcctca catcgagccc gtggctagat gcatcatccc tgatctgatc   2100
ggaatgggta agtccggcaa gagcgggaat ggctcatatc gcctcctgga tcactacaag   2160
tacctcaccg cttggttcga gctgctgaac cttccaaaga aaatcatctt tgtgggccac   2220 gactggggg ctgctctggc ctttcactac gcctacgagc accaagacag gatcaaggcc   2280
atcgtccata tggagagtgt cgtggacgtg atcgagtcct gggacgagtg gcctgacatc   2340
gaggaggata tcgccctgat caagagcgaa gagggcgaga aaatggtgct tgagaataac   2400
ttcttcgtcg agaccgtgct cccaagcaag atcatgcgga aactggagcc tgaggagttc   2460
gctgcctacc tggagccatt caaggagaag gcgaggtta gcggcctac cctctcctgg   2520 cctcgcgaga tccctctcgt taagggaggc aagcccgacg tcgtccagat tgtccgcaac   2580
tacaacgcct accttcgggc cagcgacgat ctgcctaagc tgttcatcga gtccgaccct   2640
gggttctttt ccaacgctat tgtcgaggga gctaagaagt tccctaacac cgagttcgtg   2700
```

-continued

```
aaggtgaagg gcctccactt cctccaggag gacgctccag atgaaatggg taagtacatc   2760
aagagcttcg tggagcgcgt gctgaagaac gagcagagcg gaggaggcgg cagtgagaat   2820
ccatatgtag atgcaataaa gagtttatgg aatgatcctg gaatccagga atgctatgat   2880
agacgacgag aatatcaatt atctgactct accaaatact atcttaatga cttggaccgc   2940
gtagctgacc ctgcctacct gcctacgcaa caagatgtgc ttagagttcg agtccccacc   3000
acagggatca tcgaataccc ctttgactta caaagtgtca ttttcagaat ggtcgatgta   3060
gggggccaaa ggtcagagag aagaaaatgg atacactgct ttgaaaatgt cacctctatc   3120
atgtttctag tagcgcttag tgaatatgat caagttctcg tggagtcaga caatgagaac   3180
cgaatggagg aaagcaaggc tctctttaga acaattatca catacccctg gttccagaac   3240
tcctcggtta ttctgttctt aaacaagaaa gatcttctag aggagaaaat catgtattcc   3300
catctagtcg actacttccc agaatatgat ggaccccaga gagatgccca ggcagcccga   3360
gaattcattc tgaagatgtt cgtggacctg aacccagaca gtgacaaaat tatctactcc   3420
cacttcacgt gcgccacaga caccgagaat atccgctttg tctttgctgc cgtcaaggac   3480
accatcctcc agttgaacct gaaggagtac aatctggtct aa                      3522
```

<210> SEQ ID NO 2
<211> LENGTH: 39
<212> TYPE: PRT
<213> ORGANISM: Artificial Sequence
<220> FEATURE:
<223> OTHER INFORMATION: Synthetic Construct

<400> SEQUENCE: 2

Asp Thr Gly Gly Arg Thr Pro Pro Ser Leu Gly Pro Gln Asp Glu Ser
1               5                   10                  15

Cys Thr Thr Ala Ser Ser Ser Leu Ala Lys Asp Thr Ser Ser Thr Gly
            20                  25                  30

Glu Asn Leu Tyr Phe Gln Leu
        35

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Ser Gly Gly Gly Ser
1               5

<210> SEQ ID NO 4
<211> LENGTH: 18
<212> TYPE: PRT
<213> ORGANISM: Artificial Sequence
<220> FEATURE:
<223> OTHER INFORMATION: Synthetic Construct

<400> SEQUENCE: 4

Gly Gly Gly Gly Ser Ala Asp Ile Ala Ala Ala Lys Ala Gly Gly Gly
1               5                   10                  15

Gly Ser

<210> SEQ ID NO 5
<211> LENGTH: 36

-continued

```
<212> TYPE: PRT
<213> ORGANISM: Artificial Sequence
<220> FEATURE:
<223> OTHER INFORMATION: Synthetic Construct

<400> SEQUENCE: 5

Gly Gly Gly Gly Ser Ala Asp Ile Ala Ala Ala Lys Ala Gly Gly Gly
1               5                   10                  15

Gly Ser Gly Gly Gly Gly Ser Ala Asp Ile Ala Ala Ala Lys Ala Gly
            20                  25                  30

Gly Gly Gly Ser
            35
```